United States Patent
Pandey

(10) Patent No.: US 11,324,803 B2
(45) Date of Patent: May 10, 2022

(54) METHODS AND COMPOSITIONS FOR TREATMENT OF GAUCHER DISEASE VIA MODULATION OF C5A RECEPTOR

(71) Applicant: Children's Hospital Medical Center, Cincinnati, OH (US)

(72) Inventor: Manoj Kumar Pandey, New Richmond, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 16/912,756

(22) Filed: Jun. 26, 2020

(65) Prior Publication Data
US 2020/0316171 A1    Oct. 8, 2020

Related U.S. Application Data

(63) Continuation of application No. 15/758,016, filed as application No. PCT/US2016/049237 on Aug. 29, 2016, now abandoned.

(60) Provisional application No. 62/218,122, filed on Sep. 14, 2015.

(51) Int. Cl.
| | |
|---|---|
| A61K 38/17 | (2006.01) |
| A61K 38/12 | (2006.01) |
| A61K 38/08 | (2019.01) |
| C12N 9/64 | (2006.01) |
| A61K 45/06 | (2006.01) |

(52) U.S. Cl.
CPC .......... *A61K 38/1725* (2013.01); *A61K 38/08* (2013.01); *A61K 38/12* (2013.01); *A61K 45/06* (2013.01); *C12N 9/6424* (2013.01); *C12Y 304/21043* (2013.01)

(58) Field of Classification Search
CPC .......................... A61K 38/1725; C07K 14/472
See application file for complete search history.

(56) References Cited

U.S. PATENT DOCUMENTS

| | | |
|---|---|---|
| 4,987,071 A | 1/1991 | Cech et al. |
| 5,093,246 A | 3/1992 | Cech et al. |
| 5,116,742 A | 5/1992 | Cech et al. |
| 5,506,121 A | 4/1996 | Skerra et al. |
| 6,022,951 A | 2/2000 | Sano et al. |
| 6,355,245 B1 | 3/2002 | Evans et al. |
| 7,342,115 B2 * | 3/2008 | Hutchison ............... A61P 11/06 546/301 |
| 7,556,944 B2 | 7/2009 | Myers et al. |
| 7,700,758 B2 | 4/2010 | Tzertzinis et al. |
| 8,524,862 B2 | 9/2013 | Otto et al. |
| 8,617,802 B2 | 12/2013 | Kohl et al. |
| 8,834,874 B2 | 9/2014 | Pardridge et al. |
| 9,079,949 B1 | 7/2015 | Andrien, Jr. et al. |
| 9,206,251 B2 | 12/2015 | Andrien, Jr. et al. |
| 9,447,176 B2 | 9/2016 | Rother et al. |
| 10,280,197 B2 | 5/2019 | Monikis et al. |
| 10,772,939 B2 | 9/2020 | Vitalis et al. |
| 2003/0143204 A1 | 7/2003 | Lewis et al. |
| 2003/0166282 A1 | 9/2003 | Brown et al. |
| 2006/0240436 A1* | 10/2006 | Golz .................... G01N 33/564 435/6.16 |
| 2008/0113904 A1 | 5/2008 | Woodruff et al. |
| 2015/0174243 A1 | 6/2015 | Magro |
| 2018/0243370 A1 | 8/2018 | Pandey |

FOREIGN PATENT DOCUMENTS

| | | |
|---|---|---|
| WO | WO 2005/092366 A1 | 10/2005 |
| WO | WO 2014/180961 A1 | 11/2014 |
| WO | WO 2017/048495 A1 | 3/2017 |
| WO | WO 2018/175833 A1 | 9/2018 |

OTHER PUBLICATIONS

Samstad et al. ("Cholesterol Crystals Induce Complement-Dependent Inflammasome Activation and Cytokine Release", The Journal of Immunology, 2837-2845; Feb. 19, 2014 (Year: 2014).*
Stein et al. ("Evaluation of high density lipoprotein as a circulating biomarkers of Gaucher disease activity", J Inherit Metab Dis. Apr. 2011; 34(2): 429-437 Author's manuscript, pp. 1-16 (Year: 2011).*
FH Foundation "What Is Heterozygous Familial Hypercholesterolemia?", https://thefhfoundation.org, accessed on Apr. 23, 2021, 1 page (Year: 2021).*
Platt et al. "Lysosomal storage disorders: The cellular impact of lysosomal dysfunction", J. Cell Biol., pp. 723-734; 2012 (Year: 2012).*
Markiewski et al., "The Role of Complement in Inflammatory Disease From Behind the Scenes into the Spotlight", The American Journal of Pathology, 2007, pp. 715-727 (Year: 2007).*
Ames, R.S., et al., "Isolation of Neutralizing Anti-C5a Monoclonal Antibodies from a Filamentous Phage Monovalent Fab Display Library," J Immunol, 1994, 152:4572-4581, 10 pgs.
Billy, E., et al., "Specific interference with gene expression induced by long, double-stranded RNA in mouse embryonal teratocarcinoma cell lines," PNAS USA, 2001, 98(25):14428-14433, 6 pgs.
Cain, S.A., et al., "Analysis of receptor/ligand interactions using whole-molecule randomly-mutated ligand libraries," J Immnunol Methods, 2000, 245:139-145, 7 pgs.
Clemens, J.C., et al., "Use of double-stranded RNA interference in *Drosophila* cell lines to dissect signal transduction pathways," PNAS USA, 2000, 97:6499-6503, 5 pgs.
Coughlin, B., et al., "Connecting the innate and adaptive immune responses in mouse choroidal neovascularization via the anaphylatoxin C5a and γδT-cells," Sci Reports, 2016, 6:23794, 12 pgs.

(Continued)

Primary Examiner — Lianko G Garyu
(74) Attorney, Agent, or Firm — Frost Brown Todd LLC; Nicole M. Tepe

(57) ABSTRACT

Disclosed are compositions and methods for the reduction of C5a mediated immune inflammation. The methods, in various aspects, may include the step of administering a C5aR antagonist to a subject in need of such treatment. In one aspect, the subject in need may have a lysosomal acid storage disease. Therapeutic kits and articles of manufacture are also disclosed.

19 Claims, 33 Drawing Sheets

Specification includes a Sequence Listing.

(56) References Cited

OTHER PUBLICATIONS

Croker, D.E., et al., "Discovery of functionally selective C5aR2 ligands: novel modulators of C5a signalling," Immunol Cell Biol, 2016, 94:787-795, 9 pgs.
Elbashir, S.M., et al., "Duplexes of 21-nucleotide RNAs mediate RNA interference in cultured mammalian cells," Nature, 2001, 411:494-498, 5pgs.
Gennaro. A.R., (ed.). *Remington's Pharmaceutical Sciences*, 18th Ed.. Mack Publishing Company, Easton, Pennsylvania, 1990, 8 pgs. (Table of Contents only).
Gennaro. A.R., (ed.) *Remington: The Science and Practice of Pharmacy*, 19th Ed., Mack Publishing Company, Easton, Pennsylvania, 1995, 3 pgs. (Table of Contents only).
Gennaro. A.R., (ed.) *Remington: The Science and Practice of Pharmacy*, 20th Ed., The University of the Sciences in Philadelphia, Lippincott Williams & Wilkins, 2000, 5 pgs. (Table of Contents only).
Hagemann, I.S., et al., "Structure of the Complement Factor 5a Receptor-Ligand Complex Studied by Disulfide Trapping and Molecular Modeling," J Biol Chem, 2008, 283(12):7763-7775, 20 pgs.
Haseloff, J., et al., "Simple RNA enzymes with new and highly specific endoribonuclease activities," Nature, 1988, 334:585-591, 7 pgs.
Haugland, R., "Handbook of Fluorescent Probes and Research Chemicals", Chapter5, 6th Ed., Molecular Probes, Eugene, OR, 1996, pp. 96-106, 9 pgs.
Haviland, D.L., et al., "Complete cDNA Sequence of Human Complement Pro-C5. Evidence of Truncated Transcripts Derived from a Single Copy Gene," J Immunol, 1991, 146(1):362-368, 7 pgs.
Haviland, D.L., et al., "complement component C5 [*Homo sapiens*]" protein sequence, NCBI Accession No. AAA51925, Oct. 31, 1994, 3 pgs.
Hawksworth, O.A., et al., "Complement in the fundamental processes of the cell," Mol Immunol, 2017, 84:17-25, 9 pgs.
Hawksworth, O.A., et al., "New concepts on the therapeutic control of complement anaphylatoxin receptors," Mol Immunol, 2017, 89:36-43, 8 pgs.
Helene, C., et al., "Control of Gene Expression by Triple Helix-Forming Oligonucleotides," Ann NY Acad Sci, 1992, 660:27-36, 10 pgs.
Helene, C., "The anti-gene strategy: control of gene expression by triplex-forming-oligonucleotides," Anti-Cancer Drug Design, 1991, 6:569-584, 16 pgs.
Jain, U., et al., "The C5a receptor antagonist PMX205 ameliorates experimentally induces colitis associated with increased IL-4 and IL-10," Br J Pharmacol, 2013, 168:488-501, 14 pgs.
Jayne, D.R.W., et al., "Randomized Trial of C5a Receptor Inhibitor Avacopan in ANCA-Associated Vasculitis," J Am Soc Nephrol, 2017, 28:2756-2767, 12 pgs.
Kohl, J., "Drug evaluation: The C5a receptor antagonist PMX-53," Curr Opin Mol Therap, 2006, 8(6):529-538, 10 pgs.
Kumar, V., et al., "Development and validation of a LC-MS/MS assay for pharmacokinetic studies of complement C5a receptor antagonists PMX53 and PMX205 in mice," Sci Reports, 2018, 8:8101, 11 pgs.
Lee, J.D., et al., "Pharmacological inhibition of complement C5a-C5a$_1$ receptor signalling ameliorates disease pathology in the hSOD1$^{G93A}$ mouse model of amyotrophic lateral sclerosis," Br J Pharmacol, 2017, 174:689-699, 11 pgs.
Maher, III, L.J., "DNA Triple-Helix Formation: An Approach to Artificial Gene Repressors." Bioassays, 1992, 14(12):807-815, 5 pgs.
Melton, D.A., et al., "Efficient in vitro synthesis of biologically active RNA and RNA hybridization probes from plasmids containing a bacteriophage SP6 promoter," Nucleic Acids Research, 1984, 12(18):7035-7056, 22 pgs.

Melton, D.A., "Injected anti-sense RNAs specifically block messenger RNA translation in vivo,"PNAS USA, 1985, 82:144-148, 5 pgs.
Minta, J.O., et al., "Cleavage of Human C5 by Tryspin: Characterization of the Digestion Products by Gel Electrophoresis," J Immunol, 1977, 119(5):1597-1602, 7 pgs.
Mollnes, T.E., et al., "Identification of a Human C5 β-Chain Epitope Exposed in the Native Complement Component but Concealed in the SC5b-9 Complex," Scand J Immunol, 1988, 28:307-312, 6 pgs.
Moongkarndi, P., et al., "Monoclonal antibodies against the fifth component of human complement," 115, Immunobiol, 1982, 162:397, 1 pg.
Moongkarndi, P., et al., "Immunological and functional properties of two monoclonal antibodies against human C5," 143, Immunobiol, 1983, 165:323, 1 pg.
Paczkowski, N.J., et al., "Pharmacological characterization of antagonists of the C5a receptor," Br J Pharmacol, 1999, 128:1461-1466, 6 pgs.
Pellas, T.C., et al., "Novel C5a Receptor Antagonists Regulate Neutrophil Functions In Vitro and In Vivo," J Immunol, 1998, 160(11):5616-5621, 6 pgs.
Subramanian, H., et al., "PMX-53 as a Dual CD88 Antagonist and an Agonist for Mas-Related Gene 2 (MrgX2) in Human Mast Cells," Mol Pharmacol, 2011, 79(6):1005-1013, 9 pgs.
Tan, D.S., et al., "Stereoselective Synthesis of over Two Million Compounds Having Structural Features Both Reminiscent of Natural Products and Compatible with Miniaturized Cell-Based Assays," J Am Chem Soc, 1998, 120(33):8565-8566, 2 pgs.
Ulrich, H., "RNA Aptamers: From Basic Science Towards Therapy," Handb Exp Pharmacol, 2006, 173:305-326, 22 pgs.
Vogt, W., et al., "Non-Enzymic Activation of the Fifth Component of Human Complement, by Oxygen Radicals. Some Properties of the Activation Product, C5b-Like C5," Molec Immunol, 1989, 26(12):1133-1142, 10 pgs.
Wetsel, R.A., et al., "Complement-Independent Activation of the Fifth Component (C5) of Human Complement: Limited Trypsin Digestion Resulting in the Expression of Biological Activity," J Immunol, 1982, 128(5):2209-2216, 8 pgs.
Yamamoto, K-I., et al., "The Complex of C5b and C6: Isolation, Characterization, and Identification of a Modified Form of C5b Consisting of Three Polypeptide Chains," J Immunol, 1978, 120(6):2008-2015, 8 pgs.
Yang, D., et al., "Short RNA duplexes produced by hydrolysis with *Escherichia coli* RNase III mediate effective RNA interference in mammalian cells," PNAS USA, 2002, 99(15):9942-9947, 6 pgs.
Zhang, T., et al., "The Controversial C5a Receptor C5aR2: Its Role in Health and Disease," J Immunol Res, 2017, vol. 2017, Article ID 8193932, 16 pgs.
Zuiderweg. E.R.P., et al., "Tertiary Structure of Human Complement Component C5a in Solution from Nuclear Magnetic Resonance Data," Biochem, 1989, 28(1):172-185, 14 pgs.
International Search Report and Written Opinion dated May 9, 2019 for Application No. PCT/US2019/013925, 12 pgs.
International Search Report and Written Opinion dated Sep. 9, 2020 for Application No. PCT/US2020/036235, 13 pgs.
Aflaki, E., et al., "Lysosomal storage and impaired autophagy lead to inflammasome activation in Gaucher macrophages," Aging Cell, 2016, 15:77-88, 12 pgs.
Airo, R., et al., "Gaucher's Disease Associated with Monoclonal Gammapatin of Undetermined Significance: A Case Report," Haematologica, 1993, 78:129-131, 3 pgs.
Alonzo, M.T., et al., "Platelet Apoptosis and Apoptotic Platelet Clearance by Macrophages in Secondary Dengue Virus Infections," J Infect Dis, 2012, 205:1321-1329, 9 pgs.
Arikan-Ayyildiz, MD, Z., et al., "Hyperimmunoglobulinemia in Pediatric Patients With Gaucher Disease in Southern Brazil," Pediatr Blood Cancer, 2012, 59:340, 1 pg.
Arikan-Ayyildiz, MD, Z., et al "Immunoglobulin Abnormalities and Effects of Enzyme Replacement Therapy in Children with Gaucher Disease," Pediatr Blood Cancer, 2011, 56:664-666, 3 pgs.
Atamas, S.P., et al., "Pulmonary and Activation-Regulated Chemokine Stimulates Collagen Production in Lung Fibroblasts," Am J Respir Cell Mol Biol, 2003, 29:743-749, 7 pgs.

(56) References Cited

OTHER PUBLICATIONS

Balreira, A., et al., "Uncoupling between CD1d upregulation induced by retinoic acid and conduritol-B-epoxide and iNKT cell responsiveness," Immunobiology, 2010, 215:505-513, 9 pgs.
Baron, D.N., et al., "Glucose is dextrose is glucose," Letter to the editor; Br Med J, 1976, pp. 41-42, 2 pgs.
Basu, S., et al., "Enzymatic Synthesis of Ceramide-Glucose and Ceramidelactose by Glycosyltransferases from Embryonic Chicken Brain," The Journal of Biological Chemistry, 1968, 243(21):5802-5804, 3 pgs.
Baumann, U., et al. , "A Codominant Role of FcγRI/III and C5aR in the Reverse Arthus Reaction," J Immunol, 2000, 164:1065-1070, 6 pgs.
Biburger, M., et al., "Monocyte Subsets Responsible for Immunoglobulin G-Dependent Effector Functions In Vivo," Immunity, 2011, 35:932-944, 13 pgs.
Boot, R.G., et al., "Marked elevation of the chemokine CCL18/PARC in Gaucher disease: a novel surrogate marker for assessing therapeutic intervention," Blood, 2004, 103(1):33-39, 7 pgs.
Boven, PhD., L.A., et al., "Gaucher Cells Demonstrate a Distinct Macrophage Phenotype and Resemble Alternatively Activated Mactophages," Am J Clin Pathol, 2004, 122:359-369, 11 pgs.
Bratosin, D., al., "A Cytometric Study of the Red Blood Cells in Gaucher Disease Reveals their Abnormal Shape that May Be Involved in Increased Erythrophagocytosis," Cytometry Part B (Clinical Cytometry), 2011, 80B:28-37, 10 pgs.
Braun, A., et al., "STIM1 is essential for Fcγ receptor activation and autoimmune inflammation," Blood, 2009, 113:1097-1104, 8pgs.
Brautbar, A., et al., "Effect of enzyme replacement therapy on gammopathies in Gaucher disease," Blood Cells Mol Dis, 2004, 32:214-217, 4 pgs.
Brisca, G., et al., "Coxarthritis as die Presenting Symptom of Gaucher Disease Type 1," Arthritis, Mar. 2011, 2011:361279, 4 pgs.
Bultron, G., et al., "The risk of Parkinson's disease in type 1 Gaucher disease," J Inherit Metab Dis, 2010, 33:167-173, 7 pgs.
Camou, F., et al., "Extended remission of B-cell lymphoma with monoclonal gammopathy in a patient with type 1 Gaucher disease treated with enzyme replacement therapy," Blood Cells Mol Dis, 2012, 48:51-52, 2 pgs.
Castaneda, J.A., et al., "Immune system irregularities in lysosomal storage disorders," Acta Neuropathol, 2008, 115:159-174, 16 pgs.
Connock, M., et al., "The clinical effectiveness and cost effectiveness of enzyme replacement therapy for Gaucher's disease: a systematic review," Health Technol Assess, 2006, vol. 10, No. 24, 6 pgs.
Daito, J., et al., "Neutrophil Phagocytosis of Platelets in the Early Phase of 2,4,6-trinitro-1-chlorobenzene (TNCB)-induced Dermatitis in Mice," Acta Histochem Cytochem, 2014, 47(2):67-74, 8 pgs.
Davignon, I., et al., "Normal Hematopoiesis and inflammatory Responses Despite Discrete Signaling Defects in Gα5 Knockout Mice," Molecular and Cellular Biology, 2000, 20(3):797-804, 8 pgs.
De Fost, M., et al., "Immunoglobulin and free light chain abnormalities in Gaucher disease type I: data from an adult cohort of 63 patients and review of the literature," Ann Hematol, 2008, 87:439-449, 11 pgs.
De Francesco, P.N., et al., "Fabry disease peripheral blood immune cells release inflammatory cytokines: Role of globotriaosylceramide," Mol Genet Metab, 2013, 109:93-99, 7 pgs.
De Vries, B., et al., "Complement Factor C5a Mediates Renal Ischemia-Reperfusion Injury Independent from Neutrophils," The Journal of Immunology, 2003, 170:3883-3889, 7 pgs.
Dhillon, S., "Eculizumab: A Review in Generalized Myasthenia Gravis," Drugs, 2018, 78:367-376, 10 pgs.
Florence, et al., "Physiochemical properties of drugs in solution," Chapter 3: Physiochemical Principles of Pharmacy, 4th Ed., 2006, pp. 55-92, 38 pgs.
Fonseca, M.I., et al., "Treatment with a C5aR Antagonist Decreases Pathology and Enhances Behavioral Performance in Murine Models of Alzheimer's Disease," J Immunol, 2009, 183(2): 1375-1383, 24 pgs.

Fujita, T., et al., "Impact of splenectomy on circulating immunoglobulin levels and the development of postoperative infection following total gastrectomy for gastric cancer," Br J Surg, 1996, 83:1776-1778, 3 pgs.
Furrer, P., "The central role of excipients in drug formulation," European Pharmaceutical Review, 2013, pp. 1-11, 23 pgs.
Gekko, K., et al., "Mechanism of Protein Stabilization by Glycerol: Preferential Hydration in Glycerol-Water Mixtures," Biochemistry, 1981, 20:4667-4676, 10 pgs.
Gerard, C., et al., "C5a Anaphylatoxin and Its Seven Transmembrane-Segment Receptor," Annu Rev Inummol, 1994, 12:775-808, 34 pgs.
Gervas-Arruga, J., et al., 'The Influence of Genetic Variability and Proinflammatory Status on the Development of Bone Disease in Patients with Gaucher Disease,' PLoS ONE, 2015, 10(5):e0126153, 15 pgs.
Ghazizadeh, S., et al., "Physical and Functional Association of Src-related Protein Tyrosine Kinases with FcγRII in Monocytic THP-1 Cells, "The Journal of Biological Chemistry, 1994, 269(12):8878-8884, 7 pgs.
Gillis, S., et al., "Platelet Function Abnormalities in Gaucher Disease Patients," Am J Hematol, 1999, 61:103-106, 4 pgs.
Giona, F., et al., "Platelet function and coagulation abnormalities in type 1 Gaucher disease patients: effects of enzyme replacement therapy (ERT)," J Thromb Haemost, 2006, 4:1831-1833, 3 pgs.
Givol, N., et al., "Thrombocytopenia and bleeding in dental procedures of patients with Gaucher disease," Haemophiha, 2012, 18:117-121, 5 pgs.
Godau, J., et al., "C5a initiates the Inflammatory Cascade in immune Complex Peritonitis," J Immunol, 2004, 173:3437-3445, 9 pgs.
Goldstein, I., et al., "Mechanisms of Lysosomal Enzyme Release From Human Leukocytes: Microtubule Assembly and Membrane Fusion Induced by a Component of Complement," PNAS USA, Oct. 1973, 70(10):2916-2920, 5 pgs.
Grabowski, G.A., et al., "Part 16: Lysosomal Disorders; Chapter 146: Gaucher Disease," *The Online Metabolic and Molecular Bases of Inherited Disease* (Valle, D., et al. Eds), 2010, New York: McGraw Hill, 141 pgs.
Guo, R-F., et al., "Role of C5a in Inflammatory Responses," Annual Review of Immunology, 2005, 23:821-852, 32 pgs.
Haas, P. J., et al., "Anaphylatoxins: Their Role in Bacterial Infection and Inflammation." Immunol Res. 2007, 37(3):161-175, 15 pgs.
Hara, T., et al., "Platelets Control Leukocvte Recruitment in a Murine Model of Cutaneous Arthus Reaction." Am J Pathol, 2010, 176(1):259-269, 11 pgs.
Hayase, T., et al., "Unilaterally and rapidly progressing white matter lesion and elevated cytokines in a patient with Tay-Sachs disease," Brain Dev, 2010, 32:244-247, 4 pgs.
Heller, T., et al., "Selection of a C5a Receptor Antagonist from Phage Libraries Attenuating the Inflammatory Response in Immune Complex Disease and Ischemia/Reperfusion Injury," J Immunol, 1999, 163:985-994, 10 pgs.
Hong, Y.B., et al., "Upregulation of Proinflammatory Cytokines in the Fetal Brain of the Gaucher Mouse " J Korean Med Sci. 2006, 21:733-738, 6 pgs.
Hosler, G.A., et al., "Thrombotic Thrombocytopenic Purpura and Hemolytic Uremic Syndrome Are Distinct Pathologic Entities: A Review of 56 Autopsy Cases," Arch Pathol Lab Med, 2003, 127:834-839, 6 pgs.
Jongerius, I., et al., "Staphylococcal complement evasion by various convertase-blocking molecules," J Exp Med, 2007, 204(10):2461-2471, 11 pgs.
Kaloterakis, A., et al., "Systemic AL amyloidosis in Gaucher disease. A case report and review of the literature," J Intern Med, 1999, 246:587-590, 4 pgs.
Kanfer, J.N., et al., "The Gaucher Mouse," Biochem Biophys Res Commun, 1975, 67(1):85-90, 6 pgs.
Karp, C.L., et al.,"Identification of complement factor 5 as a susceptibility locus for experimental allergic asthma," Nature Immunology, Sep. 2000, 1(3):221-226, 6 pgs.
Karsten, C.M., et al., "Anti-inflammatory activity of IgG1 mediated by Fc galactosylation and association of FcγRIIB and dectin-I," Nat Med, 2012, 18(9):1401-1406, 9 pgs.

(56) References Cited

OTHER PUBLICATIONS

Karsten, C.M., et al., "Monitoring and Cell-Specific Deletion of C5aR1 Using a Novel Floxed GFP-C5aR1 Reporter Knock-in Mouse," J Immunol, 2015, 194:1841-1855, 15 pgs.
Karsten, C.M., et al., "The immunoglobulin, IgG Fc receptor and complement triangle in autoimmune diseases," Immunobiology, 2012, 217:1067-1079, 13 pgs.
Kawashita, E., et al., "Prostaglandin E2 Reverses Aberrant Production of an Inflammatory Chemokine by Microglia from Sandhoff Disease Model Mice through the cAMP-PKA Pathway,"PLoS One, 2011, 6(1):e16269, 8 pgs.
Keating, G.M., "Eculizumab: A Review of Its Use in Atypical Haemolytic Uraemic Syndrome," Drugs, 2013, 73:2053-2066, 14 pgs.
Klos, A., et al., "International Union of Basic and Clinical Pharmacology, [corrected]. LXXXVII. Complement Peptide C5a, C4a, and C3a Receptors," Pharmacol Rev, 2013, 65:500-543, 45 pgs.
Kohl, J., et al., "A regulatory role for the C5a anaphylatoxin in type 2 immunity in asthma," J Clin Invest, 2006, 116(3):783-796, 14 pgs.
Kolev, M., et al., "Complement—tapping into new sites and effector systems," Nat Rev Immunol, 2014, 14:811-820, 10 pgs.
Koyasu, S., "The role of PI3K in immune cells," Nature Immunology, 2003, 4(4):313-319, 7 pgs.
Kumar, V., et al., "Cell-derived anaphylatoxins as key mediators of antibody-dependent type II autoimmunty in mice," The Journal of Clinical Investigation, 2006, 116(2):512-520, 9 pgs.
Lajoie, S., et al., "Complement-mediated regulation of the IL-17A axis is a central genetic determinant of the severity of experimental allergic asthma," Nat Immunol, 2010, 11(10):928-935, 9 pgs.
Lewis, A.G., et al., "Pharmacological targeting of C5a receptors during organ preservation impioves kidney graft survival," Clinical and Experimental Immunology, 2008, 153:117-126, 10 pgs.
Liszewski, M.K., et al., "Intracellular Complement Activation Sustains T Cell Homeostasis and Mediates Effector Differentiation," Immunity, 2013, 39:1143-1157, 15 pgs.
Liu, J., et al., "Gaucher disease gene GBA functions in immune regulation," Proc Natl Acad Sci USA, 2012, 109(25):10018-10023, 6 pgs.
Loirat, C., et al., "Complement and the atypical hemolytic uremic syndrome in children." Pediatr Nephrol, 2008, 23:1957-1972, 16 pgs.
Lukacs, N.W., et al., "Complement-dependent immune complex-induced bronchial inflammation and hyperreactivity," Am J Physiol Lung Cell Mol Physiol, 2001, 280:L512-L518, 7 pgs.
Luzzatto, L., "PNH from mutations of another PIG gene,"Blood, 2013, 122(7):1099-1100, 2 pgs.
Machaczka, M., et al., "Gaucher disease with foamy transformed macrophages and erythrophagocytic activity," J Inherit Metab Dis, 2011, 34:233-235, 3 pgs.
March, D.R., et al., "Potent Cyclic Antagonists of the Complement C5a Receptor on Human Polymorphonuclear Leukocytes. Relationships between Structures and Activity," Mol Pharm, Apr. 2004, 65(4):868-879, 12 pgs.
Marie, J.P., et al., "Gaucher's Disease with Monoclonal Gammopathy: Significance of Splenic Plasmacytosis," Scand J Haematol, 1982, 28:54-58, 5 pgs.
Marti, G.E., et al., "Polyclonal B-Cell Lymphocytosis and Hypergammaglobulinemia in Patients with Gaucher Disease," Am J Hematol, 1988, 29:189-194, 6 pgs.
Matsubara, S., et al., "Syk Activation in Dendritic Cells is Essential for Airway Hyperresponsiveness and Inflammation," American Journal of Respiratory Cell and Molecular Biology, 2006, 34:426-433, 8 pgs.
McAlarney, MD, T., et al., "Antisulfatide antibody and neuropathy in a patient with Gaucher's disease," Neurology, 1995, 45:1622-1623, 2 pgs.
Merad, M., et al., "The Dendritic Cell Lineage: Ontogeny and Function of Dendritic Cells and Their Subsets in the Steady State and the Inflamed Setting," Annu Rev Immunol, 2013, 31:563-604, 42 pgs.

Mistry, P.K., et al., "Gaucher Disease and Malignancy: a Model for Cancer Pathogenesis in an Inborn Error of Metabolism," Crit Rev Oncog, 2013, 18(3):235-246, 16 pgs.
Mistry, P.K., et al., "Glucocerebrosidase gene-deficient mouse recapitulates Gaucher disease displaying cellular and molecular dysregulation beyond the macrophage," Proc Natl Acad Sci USA, 2010, 107(45):19473-19478, 7 pgs.
Nakashima, H., et al., "Activation of CD1 lb$^+$ Kupffer Cells/ Macrophages as a Common Cause for Exacerbation of TNF/Fas-Ligand-Dependent Hepatitis in Hypercholesterolemic Mice," PLoS One, 2013, 8(1):e49339, 9 pgs.
Nakashima, K., et al., "A novel Syk kinase-selective inhibitor blocks antigen presentation of immune complexes in dendritic cells," European Journal of Pharmacology, 2004, 505:223-228, 6 pgs.
Nalysnyk, MD, MPH, L., et al., "Budget Impact Analysis of Eliglustat for the Treatment of Gaucher Disease Type 1 in the United States," Journal of Managed Care & Specialty Pharmacy, 2018, 24(10): 1002-1008, 7 pgs.
Nimmerjahn, F. et al., "Fc$\gamma$ receptors as regulators of immune responses," Nat Rev Immunol, 2008, 8:34-47, 14 pgs.
Nimmerjahn, F., et al., "Fc$\gamma$ Receptors: Old Friends and New Family Members," Immunity, 2006, 24:19-28, 10 pgs.
Nimmerjahn, F., et al., "Fc$\gamma$RIV: A Novel FcR with Distinct IgG Subclass Specificity," Immunity, 2005, 23:41-51,11 pgs.
Noris, M., et al., "Relative Role of Genetic Complement Abnormalities in Sporadic and Familial aHUS and Their Impact on Clinical Phenotype," Clin J Am Soc Nephrol, 2010, 5:1844-1859, 16 pgs.
Otto, M., et al., "C5a Mutants Are Potent Antagonists of the C5a Receptor (CD88) 1 and of C5L2: Position 69 is the Locus That Determines Agonism or Antagonism," J. Biol Chem., Jan. 2004, 279(1):142-51, 10 pgs.
Pandey, M.K., "Molecular Basis for Downregulation of C5a-Mediated Inflammation by IgG1 Immune Complexes in Allergy and Asthma," Curr Allergy Asthma Rep, 2013, 13:596-606, 11 pgs.
Pandey, M.K., et al., "Complement drives glucosylceramide accumulation and tissue inflammation in Gaucher disease," Nature, 2017, 543:108-112, 19 pgs.
Pandey, M.K., et al., "Cytology of Gaucher disease," *Advances in Gaucher Disease: Basic and Clinical Perspectives*, Future Medicine Ltd, 2013, pp. 78-93, 15 pgs.
Pandey, M.K., et al., "Gaucher disease: Chemotactic factors and immunological cell invasion in a mouse model," Mol Genet Metab, 2014, 111:163-171, 9 pgs.
Pandey, M.K., et al., "Immunological cell type characterization and Th1-Th17 cytokine production in a mouse model of Gaucher disease," Mol Genet Metab, 2012, 106(3):310-322, 22 pgs.
Pandey, M.K., et al., "Immunological Cells and Functions in Gaucher Disease," Crit Rev Oncog, 2013, 18(3):197-220, 30 pgs.
Parenti, G., et al., "New strategies for the treatment of lysosomal storage diseases (Review)," International Journal of Molecular Medicine, 2013, 31:11-20, 10 pgs.
Parker, C.J., "Paroxysmal nocturnal hemoglobinuria," Curr Opin Hematol, 2012, 19:141-148, 8 pgs.
Pavlova, E.V., et al., "B cell lymphoma and myeloma in murine Gaucher's disease," J Pathol, 2013, 231:88-97, 10 pgs.
Pittock, S.J., et al., "Eculizumab in AQP4-IgG-positive relapsing neuromyelitis optica spectrum disorders: an open-label pilot study," Lancet Neurol, 2013, 12L554-562, 9 pgs.
Pratt, P.W., et al., "Immunoglobulin Abnormalities in Gaucher's Disease: Report of 16 Cases," Blood, 1968, 31(5):633-640, 8 pgs.
Rafiq, K., et al., "Immune complex-mediated antigen presentation induces tumor immunity," The Journal of Clinical Investigation, 2002, 110:71-79, 9 pgs.
Ricklin, D., et al., "Complement: a key system for immune surveillance and homeostasis," Nat Immunol, 2010, 11(9):785-797, 13 pgs.
Rimkunas, V. M., et al., "TNF-$\alpha$ plays a role in hepatocyte apoptosis in Niemann-Pick type C liver disease," J Lipid Res, 2009, 50:327-333, 7 pgs.
Rittirsch, D., et al., "Functional roles for C5a receptors in sepsis," Nature Medicine, 2008, 14(5):551-557, 7 pgs.

(56) References Cited

OTHER PUBLICATIONS

Rodic, P., et al., "Gammopathy and B lymphocyte clonality in patients with Gaucher type I disease," Blood Cells Mol Dis, 2013, 50:222-225, 4 pgs.
Rosenbloom, B.E., et al., "Gaucher Disease: A Comprehensive Review," Critical Reviews in Oncogenesis, 2013, 18(3):163-175, 13 pgs.
Saitoh, S., et al.. "LAT is Essential for FcεRI-Mediated Mast Cell Activation," Immunity, 2000, 12:525-535, 11 pgs
Saroha, V., et al., "Pseudogaucher cells obscuring multiple myeloma: a case report," Cases Journal, 2009, 2:9147, 3 pgs.
Seino, J., et al., "Activation of human complement by mouse and mouse/human chimeric monoclonal antibodies," Clinical and Experimental Immunology, 1993, 94:291-296, 6 pgs.
Semple, J.W., et al., "Platelets and the immune continuum," Nat Rev Immunol, 2011, 11:264-274, 11 pgs.
Shantsila, E., et al., "The role of monocytes in thrombotic disorders: Insights from tissue factor, monocyte-platelet aggregates and novel mechanisms," Thromb Haemost, 2009, 102:916-924, 9 pgs.
Shoenfeld, Y., et al., "Gaucher's disease: a disease with chronic stimulation of the immune system," Arch Pathol Lab Med, 1982, 106(8):388-391, 1 pg. Abstract only.
Shoenfeld, Y., et al., "Natural Autoantibodies in Sera of Patients with Gaucher's Disease," J Clin Immunol, 1995, 15(6):363-372, 10 pgs.
Simonaro, C.M., et al., "Involvement of the Toll-like receptor 4 pathway and use of TNF-α antagonists for treatment of the mucopolysaccharidoses," Proc Natl Acad Sci USA, 2010, 107(1):222-227, 6 pgs.
Skokowa, J., et al., "Macrophages Induce the Inflammatory Response in the Pulmonary Arthus Reaction through $G\alpha_{i2}$ Activation That Controls C5aR and Fc Receptor Cooperation," J Immunol, 2005, 174:3041-3050, 10 pgs.
Snook, E.R., et al., "Innate Immune Activation in the Pathogenesis of a Murine Model of Globoid Cell Leukodystrophy," Am J Pathol, 2014, 184(2):382-396, 15 pgs.
Stemerding, A.M., et al., "*Staphylococcus aureus* Formyl Peptide Receptor-like Inhibitor (FLIPr) and Its Homologue FLIPr-like are Potent FcγR Antagonists that Inhibit IgG-Mediated Effector Functions," J Immunol, 2013, 191:353-362, 10 pgs.
Strainic, M.G., et al., "Locally Produced Complement Fragments C5a and C3a Provide Both Costimulatory and Survival Signals to Naive CD4+ T Cells," Immunity, 2008, 28:425-435, 11 pgs.
Sun, Y., et al., "Gaucher disease mouse models: point mutations at the acid β-glucosidase locus combined with low-level prosaposin expression lead to disease variants" J Lipid Res, 2005, 46:2102-2113, 12 pgs.
Syed, S.N., et al., "Both FcγRIV and FcγRIII are essential receptors mediating type II and type III autoimmune responses via FcRγ-LAT-dependent generation of C5a,"Eur J Immunol, 2009, 39, 3343-3356, 14 pgs.
Tridandapani, S., et al., "The Adapter Protein LAT Enhances Fcγ Receptor-Mediated Signal Transduction in Myeloid Cells," The Journal of Biological Chemistry, 2000, 275(27):20480-20487, 8 pgs.
Vairo, MD, F., et al., "Hyperimmunoglobulinemia in Pediatric Gaucher Patients in Southern Brazil," Pediatr Blood Cancer, 2012, 59:339, 1 pg.
Van Dussen, L., et al., "Cost-effectiveness of enzyme replacement therapy for type 1 Gaucher disease," Orphanet J Rare Dis, 2014, 9:51, 12 pgs.
Van Lookeren Campagne, M., et al., "Macrophage complement receptors and pathogen clearance," Cell Microbiol, 2007, 9(9):2095-2102, 8 pgs.

Vincent, M., et al., "Evaluation of an Anti-Tumor Necrosis Factor Therapeutic in a Mouse Model of Niemann-Pick C Liver Disease," PLoS One, 2010, 5(9):e12941, 6 pgs.
Wang, A.V.T., et al., "Physical and Functional Association of the High Affinity Immunoglobulin G Receptor (FcγRI) with the Kinases Hck and Lyn," J Exp Med, 1994, 1180:1165-1170, 6 pgs.
Weaver, Jr., D.J., et al., "C5a receptor-deficient dendritic cells promote induction of Treg and Th17 cells," Eur J Immunol, 2010, 40:710-721, 12 pgs.
Weber, C., et al., "Atherosclerosis: current pathogenesis and therapeutic options," Nat Med, 2011, 17(11):1410-1422, 13 pgs.
Weinreb, MD, N.J., et al., "Effectiveness of Enzyme Replacement Therapy in 1028 Patients with Type 1 Gaucher Disease after 2 to 5 Years of Treatment: A Report from the Gaucher Registry," The American Journal of Medicine, 2002, 113:112-119, 8 pgs.
Weyrich, A.S., et al., "Activated Platelets Signal Chemokine Synthesis by Human Monocytes," J Clin Invest, 1996, 97(6):1525-1534, 10 pgs.
Williams, J.W., et al., "The Contribution of Allergen-Specific IgG to the Development of Th2-Mediated Airway Inflammation," Journal of Allergy, 2012, 236075, 9 pgs.
Wine, MD, E., et al., "Hyperimmunoglubinemia in Pediatric-onset Type 1 Gaucher Disease and Effects of Enzyme Replacement Therapy," J Pediatr Hematol Oncol, 2007, 29:451-457, 7 pgs.
Woodruff, T.M., et al., "Increased Potency of a Novel Complement Factor 5a Receptor Antagonist in a Rat Model of Inflanunatory Bowel Disease," the Journal of Pharmacology and Experimental Therapeutics, 2005, 314(2):811-817, 7 pgs.
Woodruff, T.M., et al., "The Complement Factor C5a Contributes to Pathology in a Rat Model of Amyotrophic Lateral Sclerosis," The Journal of Immunology, 2008, 181:8727-8734, 8 pgs.
Woodruff, T.M., et al., "Therapeutic activity of C5a receptor antagonists in a rat model of neurodegeneration," The FASEB Journal, 2006, 20:1407-1417, 11 pgs.
Wyatt, K., et al., *The effectiveness and cost-effectiveness of enzyme and substrate replacement therapies: a longitudinal cohort study of people with lysosomal storage disorders*, Health Technol Assess, 2012, 16(39):1-543, 9 pgs.
Xu, Y-H., et al., "Comparative Therapeutic Effects of Velaglucerase Alfa and Imiglucerase in a Gaucher Disease Mouse Model," PloS One, 2010, 5(5):e10750, 15 pgs.
Xu, Y-H., et al., "Dependence of reversibility and progression of mouse neuronopathic Gaucher disease on acid β-glucosidase residual activity levels," Mol Genet Metab, 2008, 94:190-203, 14 pgs.
Xu, Y-H., et al., "Global gene expression profile progression in Gaucher disease mouse models," BMC Genomics, 2011, 12:20, 23 pgs.
Xu, Y-H., et al., "Viable Mouse Models of Acid β-glucosidase Deficiency: The Defect in Gaucher Disease," Am J Pathol, 2003, 163(5):2093-2101, 9 pgs.
Yan, C., et al., "New insights for C5a and C5a receptors in sepsis," Front Immunol, 2012, 3(Article 368):1-15, 15 pgs.
Zhang, W., et al. "Essential Role of LAT in T Cell Development," Immunity, 1999, 10:323-332, 10 pgs.
Zhang, X., et al., "A complex role for complement in allergic asthma," Expert Review of Clinical Immunology, 2010, 6(2):269-277, 17 pgs.
Zimran, A., "How I treat Gaucher disease," Blood, Jun. 2011, 118(6):1463-1471, 9 pgs.
European Search Report, Supplementary, and Written Opinion dated Apr. 2, 2019 for Application No. EP 16847046.6, 8 pgs.
International Search Report and Written Opinion dated Nov. 28, 2016 for Application No. PCT/US2016/049237, 12 pgs.

\* cited by examiner

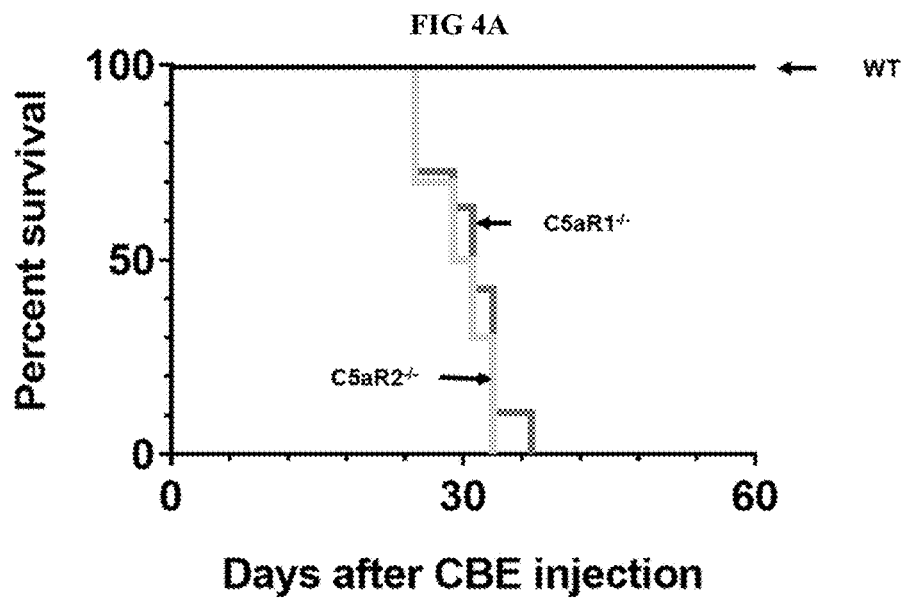
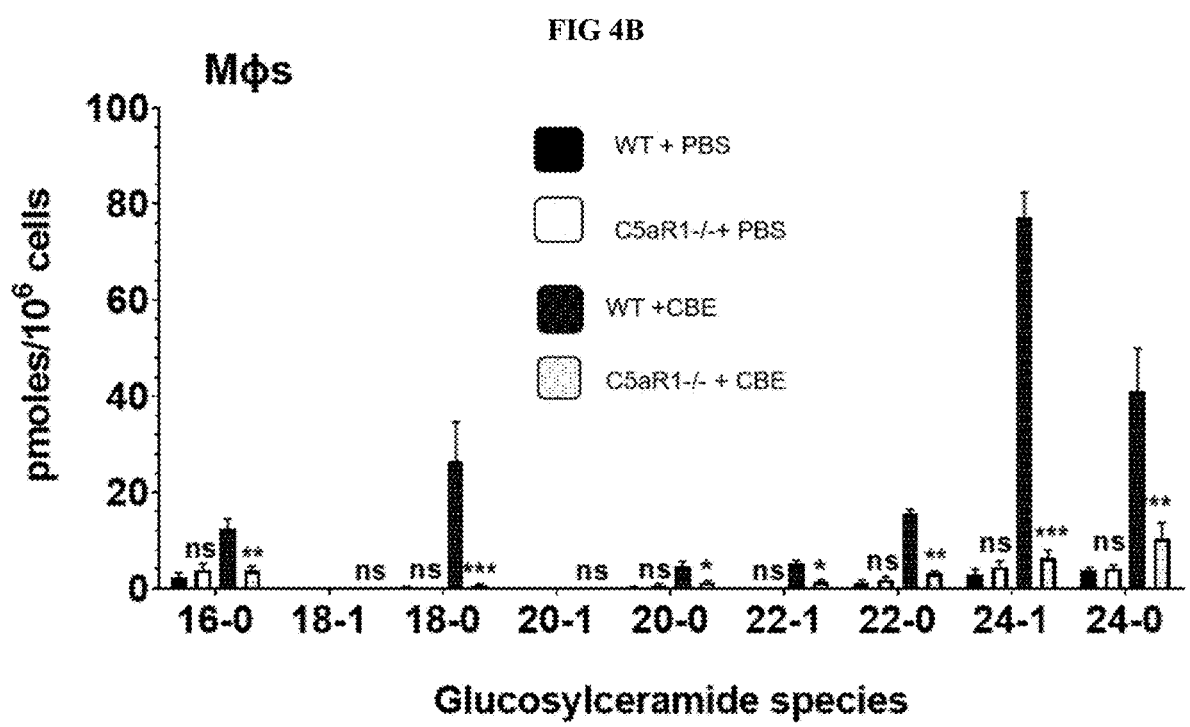

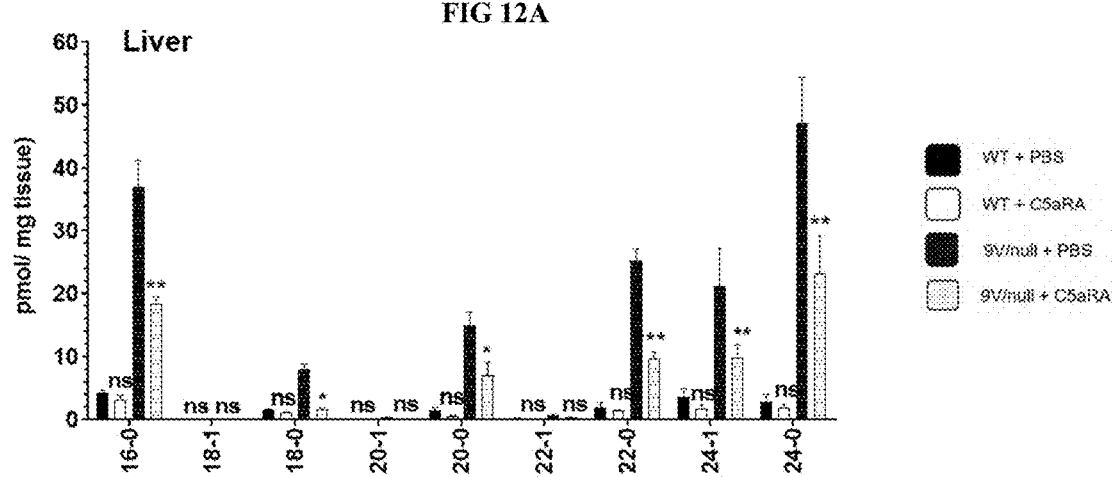
FIG 12A
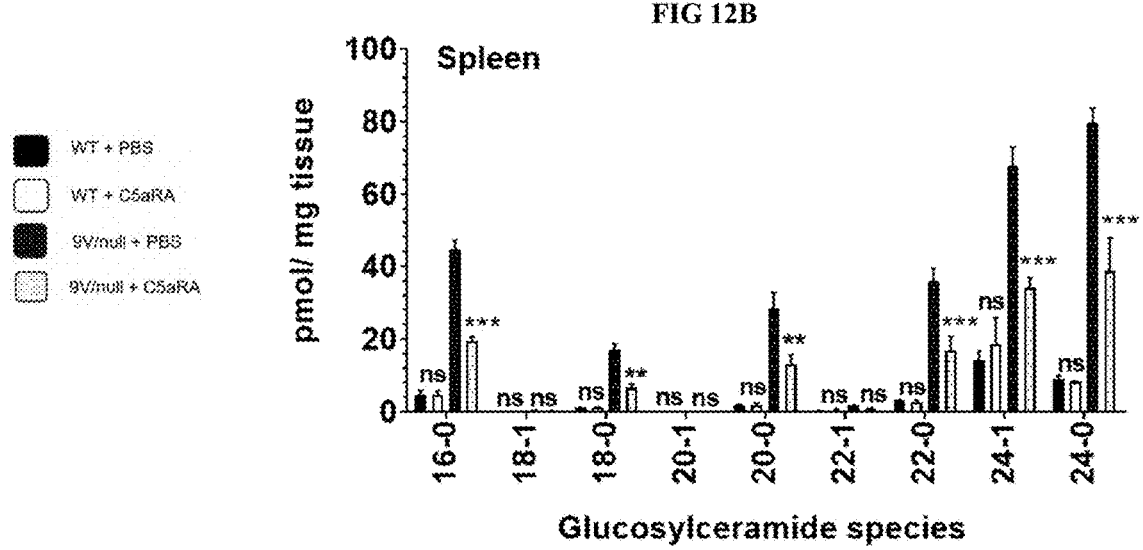
FIG 12B
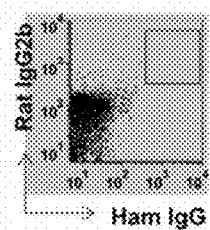 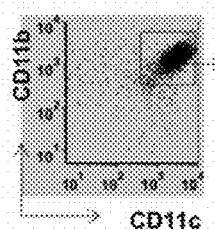 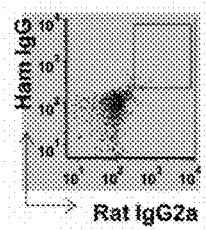 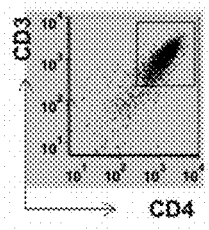
FIG 12C  FIG 12D

```
                        SEQUENCE LISTING

<160> NUMBER OF SEQ ID NOS: 1

<210> SEQ ID NO 1
<211> LENGTH: 70
<212> TYPE: PRT
<213> ORGANISM: Artificial Sequence
<220> FEATURE:
<223> OTHER INFORMATION: mutant C5a-(1-66, Cys27Ala) -A8B-Del. 71-73 of
      human C5a

<400> SEQUENCE: 1

Thr Leu Gln Lys Lys Ile Glu Glu Ile Ala Ala Lys Tyr Lys His Ser
1               5                   10                  15

Val Val Lys Lys Cys Cys Tyr Asp Gly Ala Ala Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser Phe Lys Arg Ser
65                  70
```

METHODS AND COMPOSITIONS FOR TREATMENT OF GAUCHER DISEASE VIA MODULATION OF C5A RECEPTOR

CROSS-REFERENCE TO RELATED APPLICATIONS

This application is a continuation of U.S. application Ser. No. 15/758,016, entitled "Methods and Compositions for Treatment of Gaucher Disease Via Modulation of C5A Receptor," filed Mar. 7, 2018, which claims the benefit of and priority to International Application No. PCT/US2016/049237, entitled "Methods and Compositions for Treatment of Gaucher Disease Via Modulation of C5A Receptor," filed Aug. 29, 2016, which claims the benefit of and priority to U.S. Ser. No. 62/218,122, entitled "Methods and Compositions for Treatment of Gaucher Disease via Modulation of C5A Receptor," filed Sep. 14, 2015, the contents of each are incorporated herein in their entirety and for all purposes.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is MethodsAndCompositions ST25.txt, the date of the creation of the ASCII text file is Jun. 24, 2020, and the size of the ASCII text file is 1.11 KB.

BACKGROUND

Lysosomal storage diseases such as Globoid cell leukodystrophy, GM2 gangliosidosis, Niemann-Pick C, Mucopolysaccharidoses, Fabry, Tay-Sachs, Sandhoff and Hypercholesterolemia and Gaucher's Disease are associated with increased cellular immune inflammation and have limited treatment options. Gaucher disease ("GD"), in particular, is a rare disease with an incidence of about 1 in 60,000 in the general population and 1 in 850 among Ashkenazi Jewish populations. Worldwide there are about 121,522 Gaucher disease patients and here in the US, approximately 5000 Americans are suffering from this disease.

GD results from mutations in the glucocerebrosidase gene GBA1 causing functional disruption of the encoded lysosomal enzyme, acid beta-glucosidase, leading to excess accumulation of glucosylceramide (GC) mainly in macrophages (Mbs) and elevated plasma level of cytokines and chemokines in human GD patients. lysosomal enzyme glucocerebrosidase (EC 3.2.1.45, GCase)[5]. Acid beta-glucosidase is crucial for the degradation of GC into glucose and ceramide. The excess accumulation of GC in innate and adaptive immune cells within several visceral organs, bone and brain sparks a pro-inflammatory environment resulting in tissue recruitment of several inflammatory immune cells. This pro-inflammatory environment causes tissue damage and promotes clinical GC manifestation. However, the mechanisms underlying GC-mediated chronic tissue inflammation remain elusive, making effective and targeted treatment challenging.

Improved treatments are needed. Currently, the cost to treat an individual with enzyme replacement therapy is significant, in the range of approximately $100,000 to $300,000 per year. Similarly, substrate reduction therapy (e.g., eligustat and miglustat) is equally expensive. While alternative treatments have potential, such as gene therapy, substrate reduction therapy, and alternative enzyme replacement products, such treatments have been hampered by limitations in the understanding of disease pathogenesis and toxicity concerns due to the blood brain barrier and procedural risks (particularly with respect to gene therapy methods).

Thus, there is an urgent need for alternative therapeutic options for the above-noted disease states and disease states of similar etiology. Further alternative treatments are needed for the management of disease complications in GD and other lysosomal storage diseases associated with increased cellular immune inflammation. The instant disclosure satisfies one or more of these needs in the art.

BRIEF SUMMARY

Disclosed are compositions and methods for treatment of lysosomal storage diseases via reduction of C5a mediated immune inflammation. The methods, in various aspects, may include the step of administering a composition comprising a C5aR antagonist to a subject in need of such treatment.

Without limiting the disclosure, a number of embodiments of the disclosure are described below for purpose of illustration.

Item 1: A composition comprising a C5aR antagonist for the treatment of a lysosomal storage disease, wherein the lysosomal storage disease is selected from globoid cell leukodystrophy, GM2 gangliosidosis, Niemann-Pick C, mucopolysaccharidoses, Fabry, Tay-Sachs, Sandhoff, Hypercholesterolemia, Gaucher's Disease, and combinations thereof, or wherein the lysosomal storage disease is Gaucher's Disease, or wherein the lysosomal storage disease is manifested by one or more clinical signs selected from hepatosplenomegaly, anemia, thrombocytopenia, bone defects, or a combination thereof.

Item 2: The composition according to Item 1, wherein said C5aR antagonist is an $A8^{\Delta 71-73}$ peptide.

Item 3: The composition according to either of Items 1 or 2, wherein said composition decreases C5a mediated immune inflammation.

Item 4: The composition of any of the above Items wherein said treatment results in reduced inflammation, preferably wherein said inflammation is in a sequestered site, more preferably wherein said sequestered site is in the blood and/or brain.

Item 5: A method of reducing C5a mediated immune inflammation, comprising the step of administering the composition of any one of Items 1 to 4, in an amount sufficient to reduce inflammation in a tissue of interest.

Item 6: The method of Item 5, wherein said reduction of C5a mediated immune inflammation is in a patient having a lysosomal storage disease.

Item 7: The method according to either one of Items 5 or 6, wherein said reduction of C5a mediated immune inflammation is in a patient having a lysosomal storage disease selected from globoid cell leukodystrophy, GM2 gangliosidosis, Niemann-Pick C, mucopolysaccharidoses, Fabry, Tay-Sachs, Sandhoff, Hypercholesterolemia, Gaucher's Disease, and combinations thereof, preferably wherein said reduction of C5a mediated immune inflammation is in a patient having Gaucher's Disease.

Item 8: The method according to any one of Items 5 through 7, wherein said subject has one or more signs of clinical Gaucher disease manifestation selected from hepatosplenomegaly, anemia, thrombocytopenia, bone defects, or a combination thereof.

Item 9: The method according to any one of Items 5 through 8, wherein said C5aR antagonist is administered in an amount sufficient to reduce inflammation in a tissue of interest, preferably wherein said tissue of interest is selected from brain and lung or both.

Item 10: The method according to any one of Items 5 through 9, wherein said C5aR antagonist is administered in an amount sufficient to reduce complement activation.

Item 11: The method according to any one of Items 5 through 10, wherein said C5aR antagonist is administered in an amount sufficient to reduce circulating levels of inflammatory cytokines and chemokines.

Item 12: The method according to any one of Items 5 through 11, wherein said administration step is carried out before, after, or during a second treatment, wherein said treatment is selected from substrate reduction therapy, gene therapy, substrate reduction therapy, enzyme replacement products, or a combination thereof, preferably wherein said second treatment is administration of eligustat, miglustat, or a combination thereof.

Item 13: A therapeutic kit comprising: (i) the composition according to any one of Items 1 to 4; and (ii) means for delivery of the composition to a human.

Item 14: An article of manufacture comprising: a container comprising a label; and a composition comprising: (i) the composition according to any one of Items 1 to 4, wherein the label indicates that the composition is to be administered to a human having, suspected of having, or at risk for developing, a lysosomal storage disease.

Item 15: The composition according to any of Items 1 through 4, for use in a method for treating a patient afflicted with a lysosomal storage disease.

BRIEF DESCRIPTION OF THE DRAWINGS

In FIG. 3A FIG. 3D, groups were compared using student's t-tests. In FIG. 3E-FIG. 3G, WT were compared to 9V/null mice at the indicated C5a concentrations using ANOVA. In FIG. 3E and FIG. 3F, 4 separate a priori comparisons were performed for each experimental condition, thus Bonferroni corrected significance threshold is 0.0125 (0.05/4). In FIG. 3G, Applicant compared the mice using two C5a concentrations (0 and 32 nM), thus the Bonferroni corrected significance threshold is 0.025.

FIG. 4A-4E. C5aR1-deficient mice are protected from the development of pharmacologically-induced Gaucher disease. FIG. 4A shows survival curves of WT, C5aR1$^{-/-}$ and C5aR2$^{-/-}$ (n=10 in each group) mice injected i.p. with 100 mg CBE/kg body weight or vehicle (PBS)/day for 60 days. FIG. 4B depicts distribution of GC species extracted from FACS-sorted pulmonary MΦs of vehicle-treated WT (light gray) or C5aR1$^{-/-}$ mice (carbon black) as well as CBE-treated WT (dark gray) or C5aR1$^{-/-}$ mice (black). GC species were quantified by ESI-LC-MS/MS. Five animals were used in each group. FIG. 4C and FIG. 4D depict CD40, CD80, and CD86 expression in pulmonary DCs (c) and CD40L and CD69 expression in pulmonary CD4+T cells (FIG. 4D) of vehicle-treated WT (light gray) and C5aR1$^{-/-}$ mice (carbon black) as well as CBE-treated WT (dark gray) or C5aR1$^{-/-}$ mice (carbon black). FIG. 4E depicts pulmonary DCs and CD4+T cells purified from the indicated groups were co-cultured for 48 h. Cytokine concentrations were determined by ELISA. Values are the means±s.d. Statistical difference between groups were determined by ANOVA with the a priori comparison being WT to C5aR1$^{-/-}$ mice. For each experiment, two conditions were evaluated (PBS and CBE), thus the Bonferroni corrected significance threshold is 0.025 (*$p<0.01$, ***$p<0.001$). ns=not significant.

FIG. 5A: Distribution of GC species extracted from FACS-sorted pulmonary MΦs of WT (light gray) or C5aR1$^{-/-}$ mice (carbon black) as well as 9V/null (dark gray) or C5aR1$^{-/-}$9V/null mice (black). GC species were quantified by ESI-LC-MS/MS. Fifteen animals were used in each group. FIG. 5B and FIG. 5C: CD40, CD80, and CD86 expression in pulmonary DCs (b) and CD40L and CD69 expression in pulmonary CD4+T cells (c) from WT (light gray), C5aR1$^{-/-}$ (carbon black) as well as 9V/null (dark gray) and C5aR1$^{-/-}$ 9V/null mice (black). FIG. 5D: Pulmonary DCs and CD4+T cells purified from the indicated groups were co-cultured for 48 h and cytokine concentrations were determined by ELISA. FIG. 5E: Immuno-histochemical analysis of CD68+(carbon black) tissue MΦs in liver, spleen and lung in response to vehicle (PBS) or C5aRA treatment of WT or 9V/null mice (n=15 each group). 5F: GCs extracted from the lung of vehicle (light gray, n=15) or C5aRA treated WT mice (carbon black, n=15) as well as vehicle (dark gray, n=15) or C5aRA-treated 9V/null mice (black, n=15). GC species were quantified as in (5A). FIG. 5G-FIG. 5I: FACS-sorted pulmonary CD11b+CD11c+ DCs and CD3+CD4+ T cells prepared from vehicle (PBS; light gray) and C5aRA-treated WT (carbon black column) as well as PBS (dark gray column) and C5aRA-treated 9V/null mice (black) were co-cultured for 48 h. Cells and their supernatants were used to determine the expression of the indicated co-stimulatory molecules on DCs (FIG. 5B) and T cells (FIG. 5C) and pro-inflammatory cytokines (FIG. 5I). Group sizes in (FIG. 5B-FIG. 5D) and (FIG. 5G-FIG. 5I were 15 mice/group. Values are the means s.d. Statistical difference between groups were determined by ANOVA with the a priori comparison being C5aR1-deficient to non-deficient (FIG. 5A-FIG. 5D) mice or treatment with C5aRA (FIG. 5F-FIG. 5I). For each experiment, two mouse strains were evaluated (WT or 9V/null), thus the Bonferroni corrected significance threshold is 0.025 (p<0.01, *p<0.001). ns=not significant.

FIG. 6A: Determination of GC-specific IgG1, IgG2a, IgG2b and IgG3 antibodies in the serum of WT and 9V/null mice (n=15/group) by ELISA. FIG. 6B: Quantification of GC bound to purified IgG2a of WT or 9V/null mice (n=15/group). GCs were extracted from purified IgG2a and quantified by ESI-LC-MS/MS. c GG-IC-mediated C5a production from lung-derived MΦs of 9V/null mice (n=15). C5a concentrations was measured by ELISA. FIG. 6D: GC-IC-induced phosphorylation of LAT in F4/80+ CD11b+ MΦs purified from lung of WT and 9V/null mice. FIG. 6E and FIG. 6F: C5a production in peritoneal fluid (FIG. 6E) and serum (FIG. 6F) of WT and 9V/null mice (n=5 in each group) that were injected i.p. with vehicle (ethanol) or the indicated concentrations of GC, anti-GC IgG or GC-ICs. After 2 h, peritoneal lavage fluid and sera were collected for determination of C5a by ELISA. FIG. 6G, FIG. 6H: Determination of GC-specific IgG1, IgG2a, IgG2b and IgG3 antibodies (FIG. 6G) and C5a (FIG. 6H) concentrations in the serum of healthy human individuals (n=15, filled column) and Gaucher disease patients (n=10, open column) by ELISA. FIG. 6I: Impact of GCase targeting by CBE on GC-IC-induced production of C5a by the human MΦ-like cell line U937. Cells were treated in the presence and absence of CBE for 72 hrs followed with in vitro stimulation with vehicle, GC, anti-GCIgG and GC+anti-GCIgG and C5a concentration was determined by ELISA. 6J Impact of C5aR-targeting on CCL18 production from CBE-treated M cell line U937. CBE treated and untreated human MΦ-like cell with indicated stimulation were used for measurement of CCL18, TNFα, IL10, IL6, and IL23 concentrations by ELISA. WT mice/healthy human controls/human M-like cell without CBE treatment (black columns); 9V/null mice/Gaucher disease patients/human MΦ-like cell with CBE treatment (white columns). Values are the means s.d. Statistical differences between groups were determined by student's t-test (b, h) or ANOVA. For the ANOVA, in some experiments (FIG. 6A, FIG. 6E, FIG. 6F, FIG. 6G) the a priori comparison was WT to 9V/null mice. For each of these experiment, four conditions were evaluated, thus the Bonferroni corrected significance threshold is 0.0125 (*p<0.05; p<0.01; * p<0.001). For the other experiments (FIG. 6C, 6I, 6J), the vehicle-treated was compared to other conditions (c conditions=7, p≤0.007; 6I conditions=3, p≤0.017, 6J conditions=4, p≤0.0125). In addition, for the comparison of CCL18 with C5aR1-targeting (6J), Applicant also considered post hoc comparisons. As there would be 10 different pairwise comparisons, significance for conditions other than to vehicle would require a p value ≤0.005.

FIG. 9E: Serum cytokines and chemokines from the indicated CBE-treated and untreated mice were assessed by proteome array. Values are mean±s.d. Group comparisons were done by ANOVA with the a priori comparison being WT to $C5aR1^{-/-}$ mice. For each experiment, two conditions were evaluated (PBS and CBE), thus the Bonferroni corrected significance threshold is 0.025 (, p<0.01 *, p<0.001).

(FIG. 10A) H&E preparations were made for liver, spleen, and bone marrow of CBE-treated and -untreated WT (n=15, each group) and $C5aR1^{-/-}$ mice (n=15, each group). Additionally, total cell numbers in liver, spleen and lung (FIG. 10B) of vehicle-treated WT (light gray, n=15) and $C5aR1^{-/-}$ mice (carbon black, n=15) as well as CBE-treated WT (dark gray, n=15) and $C5aR1^{-/-}$ mice (black, n=15) were determined as well as MΦs, DCs, and $CD4^+$ T cell numbers in liver (FIG. 10C), spleen (FIG. 10D) and lung (FIG. 10E). Values are the means±s.d. Group comparisons were done by ANOVA with the a priori comparison being WT to $C5aR1^{-/-}$ mice. For each experiment, two conditions were evaluated (PBS and CBE), thus the Bonferroni corrected significance threshold is 0.025 (***p<0.001).

FIG. 12A-12H. C5aRA-treated 9V/null mice show marked reduction in GCs, costimulatory expression in DCs and CD4$^+$ T cells and pro-inflammatory cytokine production. GCs were extracted and quantified from liver (FIG. 12A) and spleen (FIG. 12B) of vehicle (PBS; light gray, n=15) and C5aRA-treated (carbon black, n=15) WT as well as vehicle (PBS; dark gray, n=15) and C5aRA-treated (black, n=15) 9V/null mice.

FIG. 12C-12H: FACS-sorted DCs and CD4$^+$ T cells prepared from lung of vehicle (PBS; light gray column, n=15) and C5aRA-treated WT (carbon black column, n=15) as well as PBS (dark gray column, n=15) and C5aRA 9V/null mice (black column, n=15) were co-cultured. Cells and supernatants were used to determine the expression of the indicated co-stimulatory molecules (FIG. 12C-FIG. 12G) and pro-inflammatory cytokines (FIG. 12H) by flow cytometry and ELISA. Values shown in FIG. 12E-FIG. 12G are AMFI (see FIG. 7). Values are the means ±s.d. Group comparisons were done by ANOVA with the a priori comparison being treatment with C5aRA. For each experiment, two different mouse strains were evaluated (WT or 9V null), thus the Bonferroni corrected significance threshold is 0.025. (p<0.01, *p<0.001).

DETAILED DESCRIPTION

Figure 1:
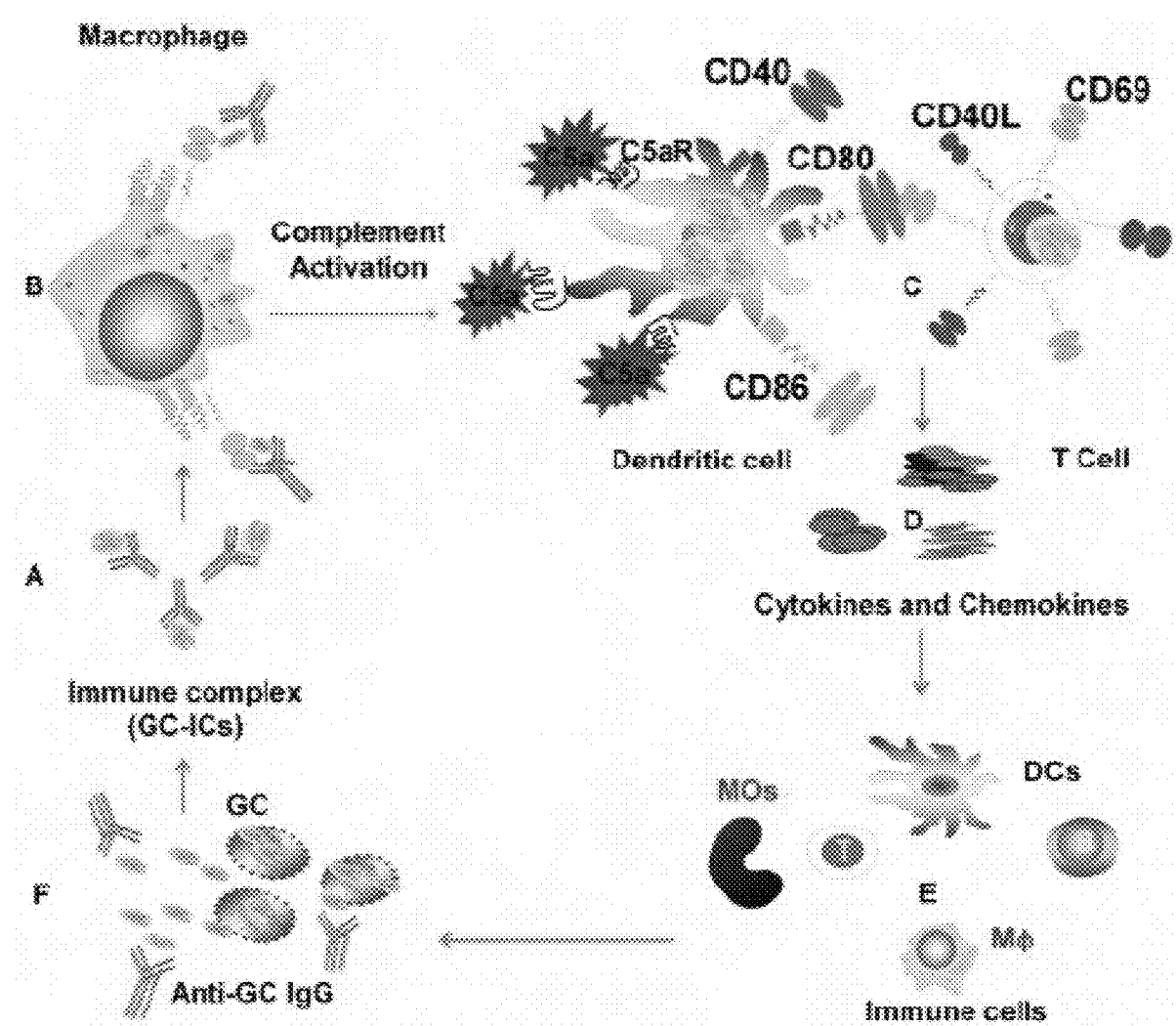
FIG. 1 is a schematic showing the GC-ICs pathway in triggering C5a-mediated inflammation in GD. It is hypothesized that formation of GC-anti-GC IgG immune complexes (A) induces APC-based production and activation of complement factors resulting in C5a generation in GD (B). C5a recognition by C5aR1 on immune cells triggers upregulation of co-stimulatory molecules (C) and the enhanced secretion of pro-inflammatory cytokines and chemokines (D). These pro-inflammatory mediators cause tissue recruitment of immune cells (E). Upon cell death, such cells release large amounts of GC (F), which is recognized by GC-specific IgG Abs, eventually resulting in GC-IC formation and amplification of inflammation in GD in a vicious cycle.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

Gaucher disease, a frequent lysosomal storage disease (LSD), is caused by mutations in GBA1 that encodes the lysosomal enzyme glucocerebrosidase (EC 3.2.1.45, GCase). The autosomal recessive inheritance of GBA1 mutations results in massive glucosylceramide (GC) accumulation in multiple innate and adaptive immune cells in spleen, liver, lung and bone marrow, thereby sparking chronic inflammation. 2

Several immune cells including macrophages (MΦs), dendritic cells (DCs), and T cells experience excess accumulation of glucosylceramide (GC), and up-regulation of co-stimulatory molecules and overproduction of pro inflammatory cytokines and chemokines in mouse model and human patients with GD. This pro-inflammatory environment drives the tissue recruitment of innate and adaptive immune cells and causes the chronic tissue inflammation in GD. However, the mechanisms by which GC causes such tissue inflammation has not been previously determined.

Disclosed herein are mechanisms by which GC-induced generation of complement C5-a (C5a) is believed to cause increased secretion of cytokines, chemokines, and enhanced tissue recruitment of inflammatory immune cells in GD. This inflammatory environment is believed to trigger clinical GD manifestation, including signs of hepatosplenomegaly, anemia, thrombocytopenia, lung, and bone defects.

Applicant has identified elevated serum and cell levels of complement 5a (C5a) and the receptor (C5aR) in a Gba1 mouse model (D409V/null; 9V/null) of Gaucher disease. C5a stimulated 9V/null DCs and T cells showed increases in co-stimulatory molecules and production of pro-inflammatory cytokines. To determine the importance of GC-induced C5a function for immune inflammation in Gaucher disease, Applicant developed conduritol B epoxide (CBE) induced Gaucher disease in WT and C5aR$^{-/-}$ mice and performed pharmacological targeting of C5aR in 9V/null mice and a chemically-induced in vitro model of human GD. Data obtained from these two mice models suggest that the GC-mediated over production of C5a as the main driver of DCs and CD4$^+$ T cells activation and their role for increased production of pro-inflammatory cytokines and chemokines, and tissue recruitment of innate and adaptive immune cells ultimately leading to tissue destruction in GD.

Applicant observed elevated level of immunoglobulin G (IgG) antibodies specific for GC in both mouse model and human GD patients. Applicant found that purified IgG from 9V/null mice was complexed with GC and GC-specific IgG stimulated MΦs of 9V/null mice, and chemically induced an in vitro human GD model, eventually driving over production of C5a. Applicant posits that GC-induced, excessive C5a generation and C5a-C5aR axis activation drive inflammation in GD. Without intending to be limited by theory, it is believed that GC-mediated complement activation and the generation of C5a are one of the primary drivers of tissue inflammation in GD. Accordingly, Applicant has identified the C5a/C5aR axis as a novel therapeutic target in GD, which could be promising for other lysosomal storage diseases.

Applicant has found that complement C5a and C5a receptor 1 (C5aR1) activation controls GC accumulation and the inflammatory response in in vivo and in vitro models of Gaucher disease. Marked local and systemic complement activation in GCase-deficient mice or after pharmacological inhibition of GCase were associated with massive GC storage, tissue inflammation and pro-inflammatory cytokine production. In studies performed by Applicant, all GCase-inhibited mice died within 4-5 weeks. In contrast, GCase and C5aR1 genetically deficient (9V/null; C5aR1$^{-/-}$) mice and wildtype mice in which GCase and C5aR were pharmacologically inhibited were protected from cellular GC storage, tissue inflammation and pro-inflammatory cytokine production, and survived. Mechanistically, in mice and humans, GCase-deficiency was associated with strong formation of complement-activating, GC-specific IgG2a/b autoantibodies, leading to massive complement activation and C5a generation. Thus, massive GC storage induces complement-activating IgG autoantibodies driving C5a generation and C5aR1 activation as a novel pathway that fuels a vicious cycle of cellular GC accumulation, innate and adaptive immune cell recruitment and activation, and clinical signs of GD. As enzyme replacement and substrate reduction therapies are expensive,[4] and still associated with inflammation[5,6], increased risk for cancer[7] and Parkinson's disease, C5aR1-targeting is believed to be a novel treatment option for GD and other lysosomal storage diseases.

In certain aspects, the disclosed therapeutic approaches may be useful for certain areas, such as "sequestered sites," e.g., the lung and brain, where existing therapies are expensive and demonstrated diminished or no response to treatment. Using the Gba1 mouse model (D409V/null; 9V/null)[9], Applicant has shown that dendritic cells (DCs) and T cells experience excess storage of GC, which is associated with up-regulation of co-stimulatory molecules, production of large amounts of pro-inflammatory cytokines, and chemokines in such cells. This inflammatory environment is believed to drive the recruitment of inflammatory monocytes (MOs), MΦs, DCs and T cells, all of which are crucial for inducing immune inflammation in human patients with GD.

Applicant has identified increased expression levels of C5a receptor 1 (C5aR1) on DCs, and CD4$^+$ T cells from 9V/null mice and high serum levels of C5a and immunoglobulin G (IgG) antibodies specific for GC in both 9V/null mouse and human GD patients. Applicant found that purified IgG from 9V/null mice is complexed with GC, suggesting that GC and GC-specific IgG form immune complexes (ICs) that activate the complement system eventually driving C5a generation in GD. To determine the importance of GC-mediated C5a generation for the development of GD, Applicant induced GD in WT and C5aR1$^{-/-}$ mice by the injection of conduritol B epoxide (CBE), which is an irreversible inhibitor of acid 6-glucosidase. Applicant found that C5aR1-deficient mice were protected from CBE-induced GD development, which was associated with reduced expression of co stimulatory molecules on DCs and CD4$^+$ T cells, pro-inflammatory cytokine and chemokine production, markedly decreased tissue recruitment of inflammatory immune cells and GC accumulation as compared with WT mice.

Pharmacological targeting of C5aR1 in 9V/null mice and a chemically-induced in vitro model of human GD also showed marked reduction in several of these GD manifestations. Without intending to be limited by theory, it is believed by Applicant that the C5a/C5aR1 axis plays a critical role for development of the pro-inflammatory environment in GD, ultimately leading to tissue destruction. It is believed that the formation of GC-specific IgG-ICs drives excessive complement activation resulting in increased C5a secretion in GD. Such C5a activates antigen presenting cells (APCs) and T cells resulting in undesired production of pro-inflammatory cytokines and chemokines eventually causing increased tissue recruitment of activated immune cells that lead to GD complications (FIG. 1). It is believed that GC-IC-induced C5a is critical for cellular inflammation and tissue damage in GD. The targeting of activating FcγR and/or C5aR1 is believed to result in reduced inflammation in GD, such that targeting of this pathway may be used in GD and other lysosomal storage diseases.

Figure 2:
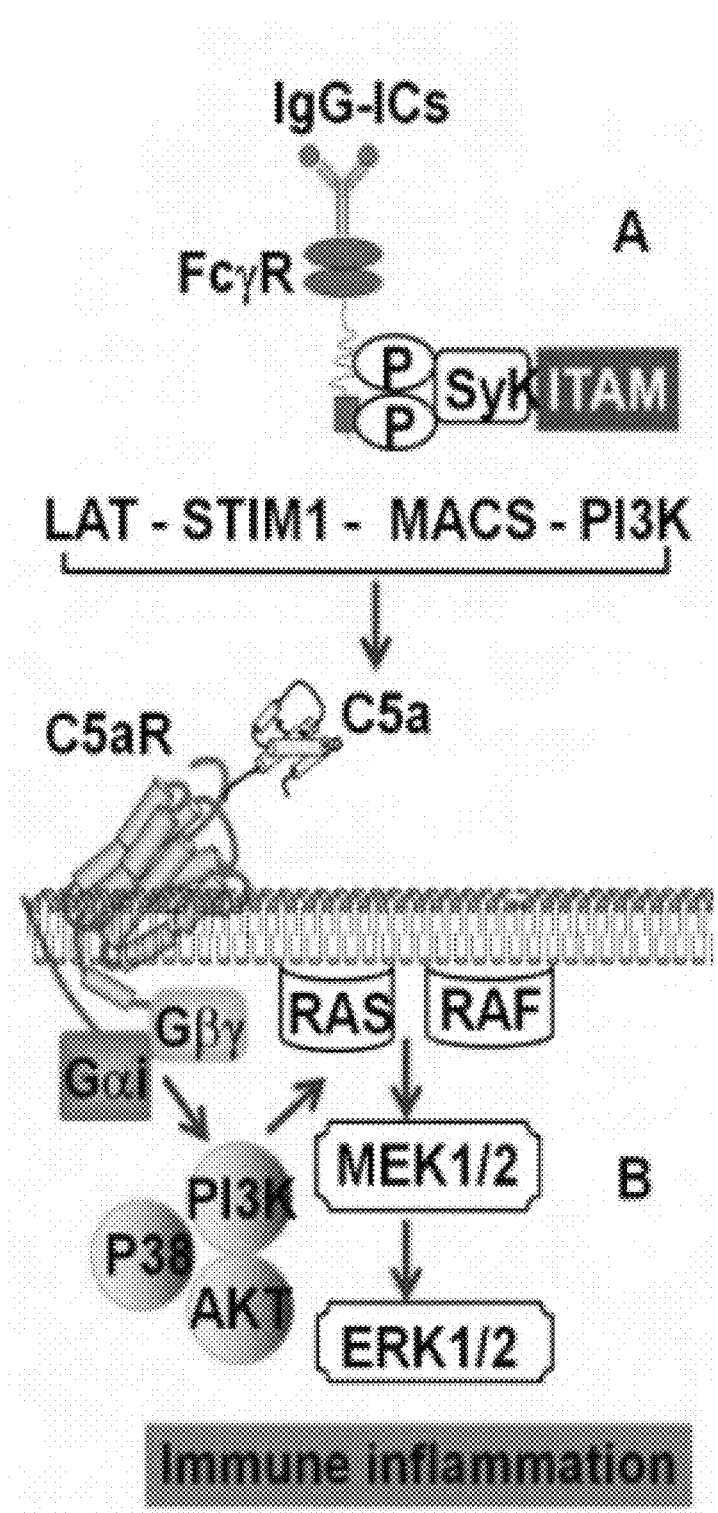
FIG. 2 is a schematic showing the pathway for IgG-ICs induced C5a signaling for immune inflammation. IgG-ICs ligation with activating FcγR causes tyrosine phosphorylation of immunoreceptor tyrosine-based motifs (ITAM) by SRC kinases in its cytoplasmic region. This leads to the recruitment of SyK kinase followed by the activation of various downstream targets, i.e., LAT, STIM-1, MACS, and PI3K. These molecules cause complement activation and subsequent generation of C5a (A). C5a ligation with C5aR cascades signaling event through Gαi and Gβγ to activate the PI3K, AKT, P38, Ras, Raf, MEK 1/2, and ERK1/2 for generation of pro-inflammatory cytokines, chemokines and tissue recruitment of inflammatory immune cells.

Increased plasma levels of IgG and the presence of auto-antigens including pyruvate-dehydrogenase, DNA, sulfatide, and rheumatoid factor have been observed in human GD patients. Applicant has observed increased production of IgG2a antibodies to GC associated with high C5a plasma levels in experimental GD, and has also observed increased production of IgG1 antibodies to GC and enhanced C5a generation in human GD patients. IgG2a/IgG2b-ICs in mice and IgG1-1Cs in humans activate the classical and alternative pathways of the complement system leading to the generation of C5a. IgG-ICs interaction with activating FcγRs causes tyrosine phosphorylation of ITAM by SRC family kinases. The latter molecule causes recruitment of SyK family kinases, followed by the activation of various downstream targets, i.e., LAT, MACs, STIM1, and P13K (FIG. 2) which cause C5a generation. Applicant has further found that GC-IC stimulated M4s from 9V/null mice and CBE-induced human GD generated high levels of C5a. Based on these findings, it is believed that GC-specific IgG antibodies, which form in response to auto-antigens, react with GC and form GC-ICs that cause up regulation of complement factors (including C5) and proteases in APCs, eventually leading to C5a generation from local C5 in GD.

Applicant and others have observed elevated level of several cytokines and chemokines, which cause tissue recruitment of inflammatory immune cells and tissue destruction in GD. Using 9V/null mice, Applicant has shown that DCs and CD4+−1− cells express high levels of co stimulatory molecules and pro-inflammatory cytokines. The molecular mechanisms that cause activation of these cells to promote the production of pro-inflammatory cytokines and chemokines critical for immune cell trafficking in GD, however, remain unclear. It is well appreciated that excessive generation of C5a and the activation of C5aR1 trigger a cascade of intracellular signaling events (FIG. 2) that lead to increased secretion of inflammatory cytokines and chemokines eventually guiding immune cells toward sites of complement activation. Applicant has observed elevated level of C5a and C5aR1 in several APCs of 9V/null mice. Further, 9V/null DC and T cell stimulation with C5a resulted in elevated levels of co-stimulatory molecules and increased production of pro-inflammatory cytokines. In CBE-induced GD Applicant has observed significantly decreased levels of such immune inflammation and prolonged survival in CBE treated C5aR1$^{-/-}$ as compared with WT. Further, DCs and T cells expressed decreased levels of co-stimulatory molecules, and produced less pro-inflammatory cytokines and chemokines in response to injection of the C5aR antagonist A8$^{\Delta 71-73}$ into 9V/null mice. C5aR antagonist A8$^{\Delta 71-73}$ treated in vitro chemical model (MO) of human GD showed marked reduction in GC-ICs induced CCL18 production, which causes T cell infiltration and act as surrogate marker of GD. Based on Applicant's findings, it is believed that GC-ICs induced signaling drives C5 production and its cleavage into C5a, and that blocking pathways that drive C5a generation will stop the vicious circle of pro-inflammatory events, providing a novel treatment option in GD and other lysosomal storage diseases, particularly for the reduction of associated inflammation.

Applicant further hypothesizes that GC-IC-induced C5a signaling will be critical for immune inflammation in GD, and that inhibition of C5aR signaling will reduce the phosphorylation of the identified signaling effectors, eventually driving cellular activation in lung and brain.

Elevated levels of APCs, (e.g., MΦs and DCs), increase erythrophagocytosis, and platelet deficiency has been observed in GD. C5a-mediated activated APCs interact with RBCs and platelets and cause their destruction. Applicant has found that C5aR antagonist A8$^{\Delta 71-73}$ treated 9V/null mice M4s showed marked reduction in GC accumulation which was associated with decreased loss of Ter119+ RBCs and CD41+ platelets. It is therefore believed that GC-IC induced C5a and the activation of C5aR1 is critical for increased phagocytosis of RBCs and platelets resulting in increased GC storage.

It is hypothesized that GC-IC-induced C5a generation promotes increased phagocytosis and damage of RBCs and platelets resulting in excess storage of GC, and that systemic C5aR1 targeting will lower the GC content in lung and brain. Thus, C5aR1 targeting may prove useful as novel therapeutic approach for GD. The available C5aR antagonist A8 $A^{\Delta71-73}$, is one such antagonist that could be used for such treatment. It is possible that the GC-IC-05a-induced GC synthase activity, which causes GC production, is more important than the RBC and platelet phagocytosis-meditated increases of GC in GD.

In one aspect, a composition comprising a C5aR antagonist for the treatment of a lysosomal storage disease is disclosed. The lysosomal storage disease may be globoid cell leukodystrophy, GM2 gangliosidosis, Niemann-Pick C, mucopolysaccharidoses, Fabry, Tay-Sachs, Sandhoff, Hypercholesterolemia, Gaucher's Disease, and combinations thereof. In one aspect, the lysosomal storage disease may be Gaucher's Disease. The lysosomal storage disease may be manifested by one or more clinical signs selected from hepatosplenomegaly, anemia, thrombocytopenia, bone defects, or a combination thereof.

In one aspect, a method of reducing C5a mediated immune inflammation is disclosed. The method may comprise the step of administering a C5aR antagonist to a subject in need thereof. In one aspect, the subject may have a lysosomal storage disease. In yet further aspects, the subject may have a lysosomal storage disease selected from globoid cell leukodystrophy, GM2 gangliosidosis, Niemann-Pick C, mucopolysaccharidoses, Fabry, Tay-Sachs, Sandhoff, Hypercholesterolemia, and combinations thereof. In a yet further aspect, the subject may have Gaucher's Disease, or one or more signs of clinical Gaucher disease manifestation selected from hepatosplenomegaly, anemia, thrombocytopenia, bone defects, or a combination thereof.

In one aspect, the C5aR antagonist may be administered in an amount sufficient to reduce inflammation in a tissue of interest. In further aspects, the tissue of interest may be one or both of brain and lung. In one aspect, the inflammation is in a sequestered site. In a further aspect, the sequestered site may be in the blood and/or brain. In one aspect, the C5aR antagonist may be administered in an amount sufficient to reduce complement activation. In other aspects, the C5aR antagonist may be administered in an amount sufficient to reduce circulating levels of inflammatory cytokines and chemokines.

In one aspect, an administration step may be carried out before, after, or during a second treatment, wherein the second treatment is selected from one or more of substrate reduction therapy, gene therapy, substrate reduction therapy, enzyme replacement products, or a combination thereof. In certain aspects, the second treatment may be administration of eliglustat, miglustat, or combinations thereof.

In one aspect, a therapeutic kit comprising: (i) a composition as disclosed herein comprising a C5aR antagonist; and (ii) means for delivery of the composition to a human is disclosed. In a further aspect, an article of manufacture is disclosed, wherein the article of manufacture may comprise a container comprising a label; and a composition as disclosed herein comprising a C5aR antagonist, wherein the label indicates that the composition is to be administered to a human having, suspected of having, or at risk for developing, a lysosomal storage disease.

Item 15: The composition according to any of Items 1 through 4, for use in a method for treating a patient afflicted with a lysosomal storage disease.

C5aR Antagonists

In one aspect, the C5aR antagonist may be selected from a C5aR antagonists as known in the art, for example, PMX205, a cyclic heptapeptide, (See Fonseca et al., J. Immunology 2009; 183:1375-1383 June 2009), hexapeptide MeFKPdChaWr, cyclic molecule AcF-[OPdChaWR] (See March et al, Mol Pharm April 2004 vol 65 no. 4, 868-879), NDT 9513727 sold by tocris.com, and others. Several of the C5a receptor 1 antagonists, i.e., PMX53, PMX20 5, HC-[OP(D-Cha)WR] and AcF-[OP(D-Cha)WR] have been introduced orally and shown to be beneficial in rat models of acute inflammation and some in human PMN-mediated effector functions under in vitro conditions (Sewell et al., 2004; Woodruff et al., 2008; Woodruff et al., 2006; Woodruff et al., 2005).

In one aspect, the C5aR antagonist is the peptide $A8^{\Delta71-73}$, as described in "Muteins of the C5a anaphylatoxin, nucleic acid molecules encoding such muteins, and pharmaceutical uses of muteins of the C5a anaphylatoxin" (U.S. Pat. No. 8,524,862 issued on Sep. 13, 2013); and "Organ transplantation solutions and methods for transplanting organs" (U.S. Pat. No. 8,617,802; issued on Dec. 31, 2013). C5aR antagonist $A8^{\Delta71-73}$ (A8B-Del.71-73), having the sequence Thr Leu Gln Lys Lys Ile Glu Glu Ile Ala Ala Lys Tyr Lys His Ser Val Val Lys Lys Cys Cys Tyr Asp Gly Ala Ala Val Asn Asn Asp Glu Thr Cys Glu Gln Arg Ala Ala Arg Ile Ser Leu Gly Pro Arg Cys Ile Lys Ala Phe Thr Glu Cys Cys Val Val Ala Ser Gln Leu Arg Ala Asn Ile Ser Phe Lys Arg Ser (SEQ ID NO: 1). In this sequence of C5aR antagonist $A8^{\Delta71-73}$, positions 27 and 68-71 of human C5a have been mutated and positions 72-74 have been deleted. This C5a mutein has been found by Applicant to reduce immune inflammation in Gaucher disease when given through i.p. routes and significantly reduces MΦs, DC and T cells mediated immune inflammation in both mouse and human model of Gaucher diseases. In contrast to the C5aR1 antagonists detailed above, the C5aR antagonist $A8^{\Delta71-73}$ has a high affinity to bind with human and mouse C5aR1 and C5aR2 (C5L2) (Otto et al., 2004) and inhibit C5a-induced effector functions (Heller et al., 1999; Otto et al., 2004). Several studies have demonstrated the efficacy of such C5aRA to block C5aR signaling in vivo in murine models of intestinal, and renal IRI, autoimmune diseases, experimental allergic asthma, kidney graft survival, severe sepsis (Baumann et al., 2000; de Vries et al., 2003; Godau et al., 2004; Heller et al., 1999; Karp et al., 2000; Lewis et al., 2008; Rittirsch et al., 2008).

Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, disorders and/or associated symptoms with the conditions, diseases or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations may contain at least 0.1% of active agent. The percentage of the compositions and preparations can, of course, be varied, and can contain between about 2% and 60% of the weight of the amount administered. The percentage of the compositions and preparations may contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The disclosed active agents may form salts. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

Pharmaceutically acceptable salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Formulations

The compounds can be formulated in various forms, including solid and liquid forms, such as tablets, capsules, pills, injections, solutions, emulsions, suspensions, gel, syrup, powder, aerosol, etc. The proportion of the active ingredient to be contained in the disclosed compositions may be determined by one of ordinary skill in the art using art recognized methods.

The compositions may contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

The composition may further comprise a pharmaceutically acceptable carrier. The resulting preparation may incorporate, if necessary, one or more solubilizing agent, buffers, preservatives, colorants, perfumes, flavorings and the like that are widely used in the field of pharmaceutical preparation.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

Preparation of Formulations

The disclosed compositions may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example *arachis* oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions may also be in the form of oil-in-water emulsions. The oil phase can be a vegetable oil, for example olive oil or *arachis* oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

Dose

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The dose administered to a subject, particularly a human, may be sufficient to effect a therapeutic response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds may be therapeutically effective at low doses. The generally useful dose range may be from about 0.001 mM, or less, to about 100 mM, or more. The effective dose range may be from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds may be generally administered in low doses.

The compounds can be used in a substantially similar manner to other known antibiotic agents for treating subjects both preventively and therapeutically. For the effective dose to be administered, whether a single dose, multiple dose, or a daily dose, will of course vary with the particular compound employed because of the varying potency of the compound, the chosen route of administration, the size of the recipient, the type of infection, and the nature of the patient's condition. One of ordinary skill in the art will be able to ascertain, without undue experimentation, appropriate protocols for the effective administration of the compounds related to the desired therapy.

Routes of Administration

The C5aR antagonist may be administered systemically. In one aspect, the C5aR antagonist may be administered in an amount sufficient to reduce GC content in lung and/or brain. The administration step may be carried out before, after, or during a second treatment, wherein the treatment may be selected from substrate reduction therapy, gene therapy, substrate reduction therapy, enzyme replacement products, or a combination thereof. In other aspects, the administration step may be carried out before, after, or during a second treatment, wherein the treatment may be administration of eligustat, miglustat, or a combination thereof.

The active compounds and/or pharmaceutical compositions of the embodiments disclosed herein can be administered according to various routes. The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. Furthermore, repeated injections can be performed, if needed, although it is believed that limited injections will be needed in view of the efficacy of the compounds.

The compounds may also be used enterally. Orally, the compounds may be administered at the rate of 100 µg to 100 mg per day per kg of body weight. Orally, the compounds may be suitably administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

The compounds may also be administered parenterally in the form of solutions or suspensions for intravenous or intramuscular perfusions or injections. In that case, the compounds may be administered at the rate of about 10 µg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 g to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) maybe administered intravenously either singly or in combination with a conventional replenisher containing glucose, amino acid and/or the like, or may be singly administered intramuscularly, intracutaneously, subcutaneously and/or intraperitoneally.

Compounds may also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

EXAMPLES

Materials and Methods
Reagents.
The following antibodies and reagents were from BD Biosciences (San Jose, Calif.) or eBiosciences (San Diego, Calif.): Monoclonal antibodies (mAb) to CD11b-pacific blue (M1/70), CD11c APC, F4/80-FITC, CD3 pacific blue, CD4 FITC, CD40 PE, CD80PE, CD86PE, CD40LPE, CD69PE, C5aR1PE, and their corresponding isotypes antibodies rat IgG2b pacific blue, Armenian hamster IgG APC, rat IgG2a PE, rat TgG2b PE). Fc blocking antibodies and anti-phospho-LAT (Tyr191), and anti-LAT clone 11B.12 were from Upstate cell signaling solutions (Lake Placid, N.Y.). The C5aR antagonist $A8^{\Delta 71-73}$ (C5aRA) was generated as described[17]. ELISA kits for the detection of human and mouse C5a and cytokines (IFN-γ, TNF-α, IL-1Q, IL-6, IL-12p40, IL-12p70, IL-17A/F, IL-23, and CCL18) were from R&D System (Minneapolis, Minn.) or eBiosciences (San Diego, Calif.). Proteome Profiler A was from R&D System (Minneapolis, Minn.), anti-Profiler A, Bio-Rad Molecular Imager@ Gel Doc™. Liberase Cl was from Roche (Indianapolis, Ind.). Deoxyribonuclease (DNase), glucosylceramide (GC), DEA, P-npp, $MgCl_2$, goat anti-mouse IgG2a, poly-l-lysine solution, and DNase-I kit were from Sigma (St. Louis, Mo.). Alkaline phosphatase-conjugated antibodies to mouse and human IgG isotypes were from Southern Biotech (Birmingham, Ala.). Tween 20, Nunc plates, Dynabeads protein G immunoprecipitation kits, and protein cross-linker resin, and BCA protein assay reagents were from Thermo Scientific (Waltham, Mass.), RIPA buffer containing Vanedate and protease inhibitors were from Roche Diagnostics (Indianapolis, Ind.). GMCSF and MCSF were from Peprotech (Rocky Hill, N.J.). Conduritol B epoxide (CBE, Calbiochem, San Diego, La Jolla, Calif.). Anti-CD11c, anti-CD11b, and anti-CD4 microbeads were from Miltenyi Biotec (Auburn, Calif.). HRP conjugated Anti-rabbit and anti-mouse IgG were from Cell Signaling Technology Inc. (Danvers, Mass.). C12-GC standards were from Matreya, LLC (Pleasant Gap, Pa.) or Avanti Polar lipids, Inc. (Alabaster, Ala.). 4-12% BisTris gel, sample loading, reducing, running buffer, standard protein molecular weight marker, iBlot 2 dry blotting system, iBind western system, and ECL chemiluminescent substrate reagent kit were from Novex, Life Technology (Carlsbad, Calif.) and Thermo Fisher Scientific Inc. (NYSE: TMO). The Gel apparatus, Xcell SureLock, and TRIzol reagent were from Invitrogen, Life Technology (Carlsbad, Calif.). OCT freezing medium was from Sakura Finetek (Torrance, Calif.) and Vectashield was from Vector Laboratories (Burlingame, Calif.). The automated hematology system (Hemavet 850) was from Drew Scientific (Oxford, Conn.). The Fortessa-I, Fortessa-II, and LSRII flow cytometers were from BD Biosciences (San Jose, Calif.). FCS Express software was from DeNovo Software (Los Angeles, Calif.). The plate reader was from Molecular Devices (Silicon Valley, Calif.).

Mice.

The D409V/null mice (9V/null) and WT controls were both on the mixed FVB/C57BL 6J/129SvEvBrd (50:25:25) backgrounds. They were used at 20-24 weeks of age[9]. To directly assess the role of C5aR1-mediated effects, 9V/null mice were backcrossed to C5aR1-deficient mice for at least 10 generations. Out of these backcrosses, Applicant generated double mutant mice ($C5aR1^{-/-}$, 9V/null) and 9V/null, WT and $C5aR1^{-/-}$ background-matched littermates. To assess the role of C5aR1, C5aR2, and FcγRs in pharmacologically-induced Gaucher disease, WT mice and those lacking C5aR1, C5aR2, and activating FcγRs ($Fcer1g^{-/-}$) or the inhibitory FcγRIIB ($Fcgr2b^{-/-}$) were used at ~12 weeks of age. Mice were maintained under pathogen-free conditions. Animal care was provided in accordance with National Institute of Health guidelines and was approved by Cincinnati Children's Hospital Medical Center IACUC.

Analysis of Sera of Control Subjects and Human Patients with Gaucher Disease Patients.

Sera from human patients with Gaucher disease (n=10) and healthy volunteers (n=15) were from the freezer and de-identified. Human patients with Gaucher disease were diagnosed at Cincinnati Children's Hospital Medical Center (CCHMC). They did not receive any specific enzyme therapy or substrate reduction therapy for Gaucher disease and are designated as untreated. The study was approved by the ethics committee at CCHMC. In vivo C5aR1 deficiency or blockade in 9V/null mice and in a CBE-induced mouse model of Gaucher disease. To assess the impact of genetic or pharmacological targeting of C5aR1 on the inflammatory response in Gaucher disease, WT (n=10) and $C5aR1^{-/-}$ mice (n=10) were treated with conduritol B epoxide (CBE), which is an irreversible inhibitor of acid β-glucosidase[24]. More specifically, both mouse strains were injected intraperitoneally (i.p.) with 100 mg CBE/kg body weight or vehicle (PBS)/day for up to 60 days, which was the termination point of these experiments. After 60 days of the indicated treatment with CBE, immune cells (MΦs, DCs, and T cells) were purified from lung of these mouse strains and used for measurement of GC, costimulatory molecules, and several of the pro-inflammatory cytokines. In additional experiments, WT (n=15) or 9V/null mice (n=15) were injected with 100 μl of the C5aR antagonist $A8^{\Delta 71-73}$ (i.p. 0.5 mg/kg) or vehicle (100 μl, PBS) on five consecutive days. Five days after the final C5aRA treatment, liver, spleen and lung were separated and measured for GC accumulation. Further, DCs and $CD4^+$ T cells were purified from the lung of the indicated mouse strains and measured for costimulatory molecule expression and the production of pro-inflammatory cytokines. Preparation of tissue cells. Liver, spleen, lung and BM were harvested aseptically. Single cell suspensions from liver and lung were obtained from minced pieces that were treated with Liberase Cl (0.5 mg/mL) and DNase (0.5 mg/mL) in RPMI (45 min, 37° C.). Single cell suspensions from spleen were obtained by grinding and then filtration through a 70-micron cell strainer. Similar suspensions of liver and lung were obtained from minced pieces that were treated with Liberase Cl (0.5 mg/mL) and DNase (0.5 mg/mL) in RPMI (45 min, 37° C.). For BM cells, femurs, tibias and humeri were flushed with sterile phosphate buffered saline (PBS), followed by RBC lysis (155 mM $NH_4Cl$, 10 mM $NaHCO_3$, 0.1 mM EDTA), passage through a strainer. Cells were then pelleted by centrifugation at 350×g. Viable cells were counted using a Neubauer chamber and trypan blue exclusion. DCs, MΦs, and $CD4^+$ T lymphocytes were purified from single cell suspensions of liver, spleen, and lung using CD11c, CD11b, and CD4 (L3T4) microbeads according to the manufacturer's protocol. The purity of the cells was ~90%-95%.

MΦ Generation from Bone Marrow Cells.

BM cells were used to differentiate MΦ as described 25. Briefly, fresh BM cells were stimulated with MCSF (10 ng/ml) in complete DMEM (FBS 10%+100 U/ml penicillin, 100 μg/ml streptomycin, 10 mM HEPES and 1 mM sodium pyruvate). Cells were seeded in six-well tissue culture plates and incubated at 37° C. in a 5% $CO_2$ atmosphere. Five days after cell seeding, supernatants were discarded and the attached cells were washed with 10 ml of sterile PBS. Ten mls of ice-cold PBS were added to each plate and incubated at 4° C. for 10 minutes. The MΦs were detached by gently pipetting the PBS across the dish. The cells were centrifuged at 200×g for 5 minutes and resuspended in 10 ml of complete DMEM. The cells were counted, seeded and cultured for 12 hours before they were used for further experiments.

Generation of BM-Derived Dendritic Cells.

DCs were differentiated from BM cells as described 25. Briefly, BM was flushed from the long bones of the limbs and depleted of red cells with ammonium chloride. Such BM cells were plated in six-well plates ($10^6$ cells/ml, 3 ml/well) in RPMI 1640 medium supplemented with FBS 10%+100 U/ml penicillin, 100 µg/ml streptomycin, 10 mM HEPES and 1 mM sodium pyruvate and 10 ng/ml recombinant murine GM-CSF at day 0,2,4, and 6. Floating cells were gently removed and fresh medium was added. At day 7, non-adherent cells and loosely adherent proliferating DC aggregates were collected, counted, seeded and cultured in for 12 hours before they were used further for further experiments.

Identification of Tissue DCs, MΦs and T Cells.

Tissue cells were suspended in PBS containing 1% BSA. After incubation (15 min, 4° C.) with Fc©R-blocking antibody 2.4G2, cells were stained (45 min, 4° C.) with the following antibodies to identify APCs and T cell: CD4 for T cells; CD11b and F4/80 for Ms; and CD11b and CD11c for DCs. Cells were also stained with the respective isotype antibodies as controls. MΦs were first identified by their typical FSC/SSC pattern, F4/80 and CD11 expression. DCs were identified as $CD11c^+CD11b^+$ cells. Further, CD40, CD80 CD86 and C5aR1 expression was determined in tissue DCs. T cells were first characterized by their FSC/SSC pattern and CD3 staining. $CD3^+T$ cells were further stained for CD4, CD40L and CD69 expression. A total of 106 events were acquired for each cell type isolated from the different organs. Specific surface expression was assessed relative to the expression of the corresponding isotype control antibody. Fortessa-I, Fortessa-II, and LSRII flow cytometers were used to characterize the cells. FCS express (version 4; DeNovo Software) was used to analyze the data.

Quantification of GC Species.

Lipids were extracted from tissues (5 mg; liver, spleen, and lung), purified immune cells, (e.g., MΦ, DCs, and $CD4^+T$) and GC-specific IgG2a by chloroform and methanol[2, 25, 26]. GCs were quantified by ESI-LC-MS/MS using a Waters Quattro Micro API triple quadrupole mass spectrometer (Milford, Mass.) interfaced with Acquity UPLC system[9]. Calibration curves were built for the GC species (C16:0, C18:0, C24:1) using C12-GC as standard. Quantification of GCs with various fatty acid chain lengths were realized by using the curve of each GC species with closest number of chain length. The total GCs in the tissues and purified IgG2a were normalized to one mg of tissue and protein and immune cells to $1\times10^6$ cells.

Determination of C5a Production and C5aR1 Expression.

C5a concentrations were determined in sera or culture supernatants from BM-derived MΦs and DCs (each of $10^6$/cells/200 µl of complete RPMI media) of WT (n=15) and 9V/null (n=15) mice, CBE-treated and -untreated WT and $C5aR1^{-/-}$ mice (n=10/group) as well as in sera obtained from human patients with untreated Gaucher disease (n=10) and healthy control humans (n=15) by commercial ELISA kits according to the manufacturer's instructions. C5aR1 expression in MΦs and DCs purified from liver, spleen and lung of WT or 9 V/null mice was evaluated by flow cytometry using a C5aR1-specific antibody.

Serum Cytokine Quantification.

For detection of cytokines and chemokines, blood from CBE-treated and -untreated WT and $C5aR1^{-/-}$ mice (n=10/group) was obtained by cardiac puncture. Sera were isolated after one-hour incubation at RT. Sera were diluted 1:10 with sterile PBS (1×) and used for detection of cytokines and chemokines with Proteome Profiler A Densitometry, which was performed with a Bio-Rad Molecular Imager® Gel Doc™ system.

Impact of C5a on GC-Induced Expression of Costimulatory Molecules and Pro-Inflammatory Cytokine Production.

To assess the GC-induced C5a influence on alteration in costimulatory molecules, DCs and $CD4^+$ T cells purified from lung of 9V/null and background matched WT mice (n=15, each group) were stimulated ex vivo in the presence and absence of different concentration of C5a (0,8,16, and 32 nM) for 24 hours at 37° C. DCs and $CD4^+$ T cells were purified liver, spleen, and lung of CBE-induced chemical model of Gaucher disease in $C5aR1^{-/-}$ (n=10) and background-matched WT mice (n=10). These DCs were used to perform FACS staining with antibodies to CD40, CD80, and CD86, whereas $CD4^+T$ cells were used to perform FACS staining with antibodies to CD40L and CD69. To assess the GC induced C5a impact on cytokines and chemokines production, DCs and $CD4^+T$ cells (1:2.5 ratio) purified from lung of 9V/null (n=15) and background-matched WT mice (n=15) were co cultured in the presence and absence of C5a (32 nM) for 48 hours in complete medium. In additional experiments, indicated ratios (1:25) of DCs and $CD4^+T$ cells purified from lung of CBE treated and untreated WT and $C5aR1^{-/-}$ mice (n=10/each group) were co-cultured for 48 hrs in complete medium. Supernatant of these experiments were used to measure IFN-©, TNF-α, IL-1β, IL-6, IL-12p40, IL-12p70, IL-23, IL-17A/F and IL-23 by ELISA.

Determination of GC-Specific IgG Antibody Concentrations.

To determine levels of IgG antibodies to GC or GS in mice and human Gaucher patients, 10 µg of GC or GS were dissolved in 1 ml of methanol and water to a final concentration of 10 µg/ml. One hundred microliters of this GC solution (1 µg/well) were used to coat a 96 well ELISA plate. In case of GS, plates were first filled with 300µ1 of poly L lysine solution (0.1 mg/ml). After 10 minutes, excess solution was removed and plates were thoroughly rinsed with sterile water and allowed to dry for several hours. Such plates were then coated with 100 µl of indicated GS solution (1 µg/well). Both of these GC and GS coated plates were kept overnight at room temperature followed by three washings with PBS containing 1% Tween-20 (PBST). Test sera (100 µl; 1:100) isolated from WT (n=15) and 9V/null mice (n=15), CBE-treated (n=10) and untreated WT mice (n=10), as well as healthy humans (n=15) and untreated Gaucher disease patients (n=10), and control antibodies to GC were loaded into the lipid-coated wells followed by incubation for 1.5 hours at RT. These plates were then washed three times with PBST and subsequently incubated with alkaline phosphatase-conjugated rat anti-mouse IgG1 (1:500 in PBS), IgG2a (1:1000 in PBS), IgG2b (1:1000 in PBS) or IgG3 (1:1000 in PBS) or alkaline phosphatase-conjugated mouse anti-human IgG1 (1:1000 in PBS), IgG2 (1:1000 in PBS), IgG3, and IgG4 (each 1:500 in PBS) in triplicates. Then, the plates were incubated for 1.5 hours at RT followed by two washing steps with PBST and one with 10 mM DEA. One hundred microliter of 1 mg/ml p-nitrophenyl phosphate in 10 nM DEA containing 5 mM MgCl2 was added into each well and incubated for 30 minutes at RT in the dark. Finally, plates were read at 405 nm to detect the GC-specific IgG antibodies.

IgG2a Purification and their Electrophoretic Separation.

To determine GC and GC-specific IgG IC formation, IgG2a was purified from pooled sera that were prepared from WT (n=15) and 9V/null mice (n=15) using an anti-mouse IgG2a immunoprecipitation kit according to the manufacturer's instruction. Briefly, pooled mouse sera (5-10 ml) were incubated with goat anti-mouse IgG2a (25-50 µg) overnight at 40° C. These samples were further incubated with 2 ml of amino link plus coupling resin overnight at 40° C. Each fraction (4-8 ml) was applied to the column followed by several washing steps with working buffer (20 mM PBS, pH 7.4). IgG2a fractions were finally eluted using 3 ml of elution buffer (0.1 Gly-HCl, pH 2.5). The IgG2a protein concentration was determined by the Lowry protein assay. Purified IgG2a was used to quantify bound GC with an ESI-LC-MS/MS system as above. Protein separation of purified IgG2a and its corresponding molecular weight markers were performed by using 12% NuPAGE Bis-Tris Mini gel and reducing SDS-PAGE system according to the manufacturer's instruction. Briefly, 4 µl of IgG2a (2.5 mg/ml) was mixed with 16 µl of reducing buffer, (e.g., 51 of NuPAGE® LDS Sample Buffer-4×, 2 µl of NuPAGE® Reducing Agent-10×, and 13 µl of deionized water) and then boiled for 5 min in boiling water bath. Approximately 10 µg of protein was applied to each lane of 12% NuPAGE Bis-Tris Mini Gels. The lower chamber of electrophoresis apparatus was filled with approximately 600 ml and upper with 200 ml of 1× NuPAGE antioxidant SDS running buffer. All PAGES were performed for 1 h at 130-180 mA at room temperature. The gel was stained with Coomassie Brilliant Blue R 250 using the standard technique.

Histological Studies:

CBE-treated and untreated WT and C5aR1$^{-/-}$ mice (n=10 each group) as well as C5aRA and vehicle treated WT and 9V/null mouse strains (n=15 each group) and minimum of two sections were examined from each tissue. Liver, spleen, and bone were harvested after the mice had been perfused with PBS and the tissues fixed in 10% formalin or 4% paraformaldehyde, and processed for paraffin or frozen blocks, respectively. Paraffin sections of indicated tissues were stained with hematoxylin and eosin (H&E) whereas frozen sections were stained with rat anti-mouse CD68 (1:100) followed by biotinylated goat anti-rat and streptavidin conjugated antibodies as described earlier[9, 27]. To determine whether GC induces the complement activation in Gaucher disease, Applicant used fresh tissues, (e.g., liver, spleen and lung) of CBE treated and untreated WT and C5aR$^{-/-}$ mice (n=10, each group). These tissues were embedded in OCT freezing medium and frozen in liquid nitrogen, transported into dry ice, and stored at −80C until use.

Tissues were then sectioned at 5-7 µm and fixed with cold acetone and permeablized with 0.2% Triton x-100 in 1× phosphate buffered saline (PBS). Tissue sections were blocked with 2% BSA and counter stained with FTC conjugated antibodies to mouse C3/C3b (2 µg/ml) and their isotype control for overnight at 40 C. Tissues were washed and cover slipped with Vectashield. Immunofluorescence images were captured with a Zeiss Apotome microscope (AxioV200) at excitation of 506 nm.

GC-IC-Induced Ex Vivo and In Vivo Production of C5a in the 9V/Null Mouse Model of Gaucher Disease.

To investigate the direct impact of GC-ICs on C5a releases in Gaucher disease, MΦs ($10^6$ cells/200 µl of complete RPMI media) purified from lung tissues of 9V/null mice (n=15) were ex vivo stimulated in the presence or absence of GC (0.25, 0.5, and 1.0 µg), anti-GC IgG (25 µg), or each indicated concentrations of GCs (0.25, 0.5, and 1.0 µg) with anti-GC IgG (25 µg of anti-GC IgG) for 2 hrs. Supernatants were used to determine C5a concentrations by ELISA. To evaluate the impact of GC-ICs impact on C5a secretion in vivo, WT and 9V/null mice were injected i.p. with vehicle (ethanol, n=15), GC (n=15), anti-GC IgG (n=15) or GC ICs (n=15). After 2 hrs, serum and peritoneal lavage fluid were collected and C5a was measured according to the manufacturer's instructions.

Detection of Linker of Activated T Cells (LAT) Phosphorylation.

After incubation of lung derived F4/80$^+$CD11b$^+$ MΦs ($5\times10^6$) from lung of WT (n=15) and 9V/null mice (n=15) with GCs (1.0 µg) and anti-GC IgG (25 µg of anti-GC IgG) or vehicle (1 µl methanol)/1000 ul of media for 5 min at 37° C., cells were collected and pellets were lysed with 1×RIPA buffer containing Vane date and protein inhibitors. Protein concentrations were determined in cell lysates using BCA protein assay. Each 10 µg of cell lysates were loaded on an 10% SDS-PAGE and transferred onto a PVDF membrane and probed with antibodies to phosphorylated LAT (pLAT; 1:200) and non-phosphorylated LAT (LAT, 1:1000) using the iBlot™ 2 Gel transfer device and iBind western system according to the manufacturer's instruction. pLAT (~36/38 kDa) and LAT (~36/38 kDa) proteins were visualized using anti-rabbit and anti-mouse secondary antibodies conjugated to HRP (1:1000) and the Novex® ECL chemiluminescent substrate reagent kit. In additional experiments, purified MΦs ($1\times10^6$) from the lung of WT (n=15) or 9V/null (n=15) mice were stimulated in the presence or absence of the indicated concentration of GC-ICs, vehicle (methanol) for 5 min at 37° C. and subsequently analyzed for pLAT and LAT by intracellular staining with anti-rabbit and anti-mouse secondary antibodies to PE as described before.

GC-IC-Mediated C5a Production in Gaucher Disease Patients.

To conclude whether GC-ICs causes C5a generation in human Gaucher disease patients, sera prepared from healthy human (n=15) and Gaucher disease patients (n=10) were diluted 1:10.000 with normal saline and used to identify C5a by commercial ELISA kits according to the manufacturer's instructions. To determine the direct impact of GC-ICs on C5a release in human Gaucher disease, the human MΦ cell line U937 ($10^6$ cells/200 µl of complete RPMI media) was treated with CBE at 370 C and 5% C02 for 72 hrs. These cells were then stimulated in the presence or absence of GC (1 µg), anti-GC IgG (25 g/ml) or GC (1 µg), +anti-GC Ig (25 µg). Supernatants were used to determine C5a concentrations by ELISA.

Statistical Analysis.

All quantitative experiments (for example western blot, GC content) were repeated at least three times. The sample sizes in all animal studies were estimated based on effect sizes present in pilot studies to ensure sufficient power. The number of animals used in each experiment is outlined in the relevant sections in the Methods. An unpaired Student's t-test (for two groups) or one-way analysis of variance (ANOVA) (for more than two groups) were used to determine significant differences between groups (Graph Pad Prism). For the Anova, rather than considering all possible pairs of comparisons, Applicant focused on a restricted set of a priori comparisons. Specifically, Applicant performed analysis to determine the impact of 1) genotype, 2) C5aRA treatment, and 3) GCase targeting. Within each of these specific tests, Applicant applied Bonferroni correction based on the number of a priori comparisons made. For analyses which were not pre-specified, the Bonferonni comparison was make on the number of possible comparisons. All data in the bar graphs are reported as mean±s.d. *P<0.05, P<0.01, P*<0.001 were considered statistically significant, for t-tests, and significance thresholds for the ANOVAs are dependent on the number of comparisons.

In Vivo C5aR Deficiency or Blockade in 9V/Null and Chemical Mouse Model of Gaucher Disease.

To assess the impact of C5aR deficiency or blockade on immunological inflammation in Gaucher disease, conduritol B epoxide (CBE) were used to induce chemical mice model of Gaucher disease in both C5aR$^{-/-}$ (n=10) and their background matched WT mice (n=10) strains. These mice strains were injected intraperitoneal with 100 mg CBE/kg body weight or vehicle (PBS)/day for 30 days. In additional experiments, WT (n=10) and 9V/null mice (n=10) were injected with 100l of C5aR antagonist A$^{8A71-73}$ (i.p, 0.5 mg/kg) on days-1, 2, 3, 4, and 5. Animals (n=10/group) treated with their vehicle (100 µl, PBS) served as controls.

Cell Preparation.

Livers, spleens, lung, and bone marrows from different mice strains were removed aseptically. Single cell suspensions from liver and lung were obtained from minced pieces that were treated with Liberase Cl (0.5 mg/mL) and DNase (0.5 mg/mL) in RPMI (45 min, 37° C.). Single cell suspensions from spleen were obtained by grinding and filtration through a 70-micron cell strainer. Similar suspensions of other tissues, (e.g., liver and lung) were obtained from minced pieces that were treated with Liberase Cl (0.5 mg/mL) and DNase (0.5 mg/mL) in RPMI (45 min, 37° C.). For bone marrow cells, the femurs, tibias, and humeri were flushed with sterile phosphate buffered saline (PBS), followed by RBC lysis (155 mM $NH_4Cl$, 10 mM $NaHCO_3$, 0.1 mM EDTA), passage through a strainer, and pelleted by centrifugation at 350 g. Viable cells were counted using a Neubauer chamber and trypan blue exclusion. DCs, M*s, and CD4$^+$ T lymphocytes were purified from single cell suspensions of liver, spleen, and lung using CD11c, CD11b, and CD4 (L3T4) microbeads according to the manufacturer's protocol. Purity of these cells was ~90%-95%.

MΦ Generation from Bone Marrow Cells.

Bone marrow cells were used to generate MΦ as previously described (Pandey et al., 2012). Briefly, fresh bone marrow cells were stimulated with MCSF (10 ng/ml) in complete Dulbecco modified Eagle medium (FBS 10%+100 U/ml penicillin, 100 µg/ml streptomycin, 10 mM HEPES and 1 mM sodium pyruvate). Cells were seeded in 6 well tissue culture plates and incubated at 37° C. in a 5% $CO_2$ atmosphere. Five days after seeding the cells, supernatants were discarded and the attached cells were washed with 10 ml of sterile PBS. Ten ml of ice-cold PBS were added to each plate and incubated at 4° C. for 10 minutes. The MΦs were detached by gently pipetting the PBS across the dish. The cells were centrifuged at 200× g for 5 minutes and resuspended in 10 ml of above media. The cells were counted, seeded and cultivated in tissue culture plates 12 hours before any further experimental procedure.

DC generation from bone marrow cells.

DC was generated from mice bone marrow cells as discussed (Pandey et al., 2012). Briefly, bone marrow was flushed from the long bones of the limbs and depleted of red cells with ammonium chloride. These bone marrow cells were plated in six-well culture plates ($10^6$ cells/nil, 3 ml/well) in RPMI 1640 medium supplemented with FBS 10%+100 U/ml penicillin, 100 µg/ml streptomycin, 10 mM HEPES and 1 mM sodium pyruvate and 10 ng/ml recombinant murine GM-CSF at day 0,2,4, and 6 of culture, floating cells were gently removed and fresh medium was added. at day 7 of culture, nonadherent cells and loosely adherent proliferating DC aggregates were collected, counted, seeded and cultivated in tissue culture plates 12 hours before any further experimental procedure.

Flow Cytometry.

For identification of cellular phenotypes in organs, cells were suspended in PBS containing 1% bovine serum albumin. After incubation (15 min, 4° C.) with the blocking antibody 2.4G2 (FcγRIII/I), cells were stained (45 min, 4° C.) with antibodies for different cell types including 1) CD4 for T cells, 2) CD11b and F480 for MΦs, 3) CD11b and CD11c for DCs. Cells were also stained with the respective isotype antibodies as controls. Flow cytometric analyses were performed where MΦs were gated first by their typical FSC/SSC pattern based on F4/80 positivity and double stained for F4/80 and CD11b. Similarly, DCs were gated for CD11c positivity and double stained for CD11c and CD11b. DCs were also characterized for their positivity of CD40, CD80, and CD86. Additionally, these APCs were also characterized for their positivity of CD88. Flow cytometer analyses of T lymphocytes were generated after gating lymphocytes from forward and side scatter and then identifying the CD3$^+$ T lymphocytes. CD3$^+$ T cells were double stained for CD4$^+$ and several inflammatory markers, (e.g., CD40L, CD69). A total of $10^6$ events were acquired for each cells types of each organ. Fortessa-I, Fortessa-II, and LSRII flow cytometer and FCS DeNovo Software were used to analyze these data.

Quantification of GCs.

Lipids were extracted from purified immune cells, (e.g., MΦ, DCs, and CD4$^+$T) from lung tissues of CBE treated and untreated WT and C5aR$^{-/-}$, C5aR antagonist A8$^{A71-73}$, treated and untreated WT and 9V/null mice and IgG2a purified from WT and 9V/null mice sera (n=10/group) as discussed in Applicant's earlier publications (Pandey et al., 2014; Pandey et al., 2012). GCs were quantified by ESI-LC-MS/MS using a Waters Quattro Micro API triple quadrupole mass spectrometer (Milford, Mass.) interfaced with Acquity UPLC system. Calibration curves were built for the GC species (C16:0, C18:0, C24:1) using C12-GC as standard. Quantification of GCs with various fatty acid chain lengths were realized by using the curve of each GC species with closest number of chain length. The total GCs in the tissues and purified IgG2a were normalized to per mg of tissue and protein and immune cells to 1×$10^6$ cells.

C5a and C5aR Measurement.

To determine whether GC causes up regulation of C5a and C5aR in Gaucher disease, sera and culture supernatant obtained from bone marrow generated MΦs and DCs (each of $10^6$/cells/200 µl of complete RPMI media) of WT (n=10) and 9V/null (n=10) mice were used to identify C5a by commercial ELISA kits according to the manufacturer's instructions. CD4 T cells, MΦs, and DCs purified from different organs, (e.g., liver, spleen, and lung) of WT (n=10, filled column) and 9V/null mice (n=10, open column) were used to measured C5aR by FACS staining with antibodies to CD88 as discussed (flow cytometry section).

Serum Cytokines Quantification.

For detection of cytokines and chemokines, Applicant drew blood from CBE treated and untreated WT and C5aR$^{-/-}$ mice (n=10/group) by cardiac puncture. Sera were isolated after one hour incubation at RT. Sera were diluted 1:10 with sterile PBS(1×) and used for detection of cytokines and chemokines with Proteome profiler A Densitometry, which was performed with a Bio-Rad Molecular Imager® Gel Doc™ system.

GC Induced C5a Impact on Co Stimulatory Molecules and Pro-Inflammatory Cytokines Production.

To assess the GC induced C5a influence for alteration in costimulatory molecules, DCs purified from lung and CD4$^+$ T cells purified from spleen of 9V/null and background matched WT mice (n=5, each group) were stimulated ex vivo in the presence and absence of different concentration of C5a (0,8,16,32 nM) for 24 hrs at 37°C. Furthermore, DCs, and CD4$^+$ T cells were purified from different organs, (e.g., liver. Spleen, and lung) of CBE induced chemical model of Gaucher disease in C5aR$^{-/-}$ (n=10) and background matched WT mice (n=10). These DCs were used to perform FACS staining with antibodies to CD40, CD80, and CD86, whereas CD4$^+$ T cells were used to perform FACS staining with antibodies to CD40L and CD69 as discussed (flow cytometry section). To assess the GC induced C5a impact on cytokines and chemokines production, a 1: 2.5 ratio of DCs (CD11c$^+$ CD11b$^+$) purified from lung and CD4$^+$ T cells purified from spleen of 9V/null (n=5) and background matched WT mice (n=5) were co cultured in the presence and absence of C5a (32 nM) for 48 hrs in complete medium. In additional experiments, indicated ration (1:25) of DCs and CD4$^+$ T cells purified from lung and spleen of CBE treated and untreated WT (n=10/group) and C5aR$^{-/-}$ mice (n=10/group) strains were co cultured for 48 hrs in complete medium. Supernatant of these experiments were used to measure several cytokines, (e.g., IFNγ, TNFα, I1β, IL6, IL12p40, IL12p70, IL23, IL17A/F, and IL23) by ELISA.

GC Specific IgG Antibodies Measurement.

To determine whether both mouse model and human patients with Gaucher disease have increased level of IgG antibodies to GC, 10 μg of GC were dissolved in 1 ml of methanol making the final concentration 10 μg/ml. This solution was used to coat a 96 well plate (Nunc) with 100 μl of each lipid separately (1 μg/well). These plates were kept at room temperature overnight for complete evaporation of methanol followed by three washings with PBS containing 1% Tween-20 (PBST). 100 μl of test sera (1:100) isolated from WT (n=10) and 9 V/null mice (n=10), and CBE treated (n=10) and un treated WT mice (n=10), as well as healthy human (n=15) and Gaucher disease patients (n=5) were loaded into the lipid coated wells followed by the incubation at RT for 1.5 hours. The serum coated wells were washed three times with PBST and then incubated with alkaline phosphatase conjugated rat anti mouse IgG1 (1:500 in PBS), IgG2a (1:1000 in PBS), IgG2b (1:1000 in PBS), IgG3 (1:1000 in PBS), and IgM (1:2000) as well as alkaline phosphatase conjugated mouse anti human IgG1 (1:1000 in PBS), IgG2 (1:1000 in PBS), and IgG3 (1:500 in PBS) in triplicates. These plates were incubating at room temperature for 1.5 hours followed by two washing with PBST and once with 10 mM DEA. 100 μl of 1 mg/ml p-nitrophenyl phosphate (p-npp) in 10 mM DEA containing 5 mM MgCl2 will be added into each well of the plate and incubate at room temperature for 30 minutes in the dark. Plates were read at 405 nm wavelength to detect the GC specific IgG antibodies.

IgG2a Purification and their Electrophoretic Separation.

To determine, whether GC and GC-specific IgG form GC specific immune complexes, IgG2a was purified from pooled sera prepared from WT (n=10) and 9V/null mice (n=10) using with anti-mouse IgG2a and immunoprecipitation kit according to the manufacturer's instruction. Briefly, pooled mice sera (5-10 ml) were incubated with goat anti mouse IgG2a (25-50 μg) for overnight at 4° C. These samples were further incubated with 2 ml of amino link plus coupling resin for overnight at 4° C. Each fraction (4-8 ml) was applied to the column followed by several washing with working buffer (20 mM PBS, pH7.4). IgG2a fractions were finally eluted with using the 3 ml of elution buffer (0.1 Gly-HCl, pH 2.5) and protein concentration was measured at 750 nm by Lowery et al method. Purified IgG2a was used to analyze the GC by using ESI-LC-MS/MS system as discussed (Quantification of GCs).

Protein separation of purified IgG2a and its corresponding molecular weight markers were performed by using 12% NuPAGE Bis-Tris Mini gel and reducing SDS-PAGE system according to the manufacturer's instruction. Briefly, 4 μl of IgG2a (2.5 mg/ml) was mixed with 16 μl of reducing buffer, (e.g., 5 μl of NuPAGE® LDS Sample Buffer-4×, 2p4 of NuPAGE® Reducing Agent-10×, and 13 μl of deionized water) and then boiled for 5 min in boiling water bath. Approximately 10 μg of protein was applied to each lane of 12% NuPAGE Bis-Tris Mini Gels. The lower chamber of electrophoresis apparatus was filled with approximately 600 ml and upper with 200 ml of 1× NuPAGE antioxidant SDS running buffer. All PAGES were performed for 1 h at 130-180 mA at room temperature. The gel was stained with Coomassie Brilliant Blue R 250 using the standard technique.

Histological Studies:

For histological studies, 5 mice from each group of CBE treated and untreated WT and C5aR$^{-/-}$ mice strains and minimum of two sections were examined from each tissue. For light microscopic studies organs (spleen, lung, and bone) were dissected after the mice had been perfused with PBS and the tissues fixed in 10% buffered formalin and embedded in paraffin for H&E staining. To determine whether GC induces the complement activation in Gaucher disease, Applicant used fresh tissues, (e.g., liver, spleen and lung) of CBE treated and untreated WT and C5aR$^{-/-}$ mice (n=5, each group). These tissues were embedded in OCT freezing medium and frozen in liquid nitrogen, transported into dry ice, and stored at −80 C until use. Tissues were then sectioned at 5-7 μm and fixed with cold acetone and permeablized with 0.2% Triton X-100 in 1× phosphate buffered saline (PBS). Tissue sections were blocked with 2% BSA and counter stained with FITC conjugated antibodies to mouse C3 (2 μg/ml) and their isotype control for overnight at 4 C. Tissues were washed and cover slipped with Vectashield. Immunofluorescence images were captured with a Zeiss Apotome microscope (AxioV200) at excitation of 506 nm.

GC-ICs—Induced Ex Vivo and In Vivo Production of C5a in 9V/Null Mouse Model of Gaucher Disease.

To investigate direct impact of GC-ICs on C5a releases in Gaucher disease, MΦs (each of 10$^6$/cells/200 μl of complete RPMI media) purified from lung tissues of 9V/null mice (n=5) were ex vivo stimulated in the presence and absence of GC (0.25, 0.5, and 1.0 μg), anti-GC IgG (25 μg), or each indicated concentrations of GCs (0.25, 0.5, and 1.0 μg) with anti-GC IgG (25 μg of anti-GCIgG) for 2 hrs and supernatants were used to measure C5a by ELISA. To evaluate the in vivo GC-ICs impact on C5a secretion, WT and 9V/null mice were injected (i.p.) with vehicle (ethanol, n=5), GC (n=5), anti-GC IgG (n=5) or GC ICs (n=5). After 2 hours, serum and peritoneal lavage fluid were collected and C5a was measured according to the manufacturer's instructions.

GC-ICs Mediated C5a Production in Human Gaucher Disease.

To conclude whether GC-ICs causes C5a generation in human Gaucher disease patients, sera prepared from healthy human (n=15) and Gaucher disease patients (n=5) were diluted 1:10000 with normal saline and used to identify C5a by commercial ELISA kits according to the manufacturer's instructions. To investigate direct impact of GC-ICs on C5a releases in human Gaucher disease, human MΦs cell line (U937, each of $10^6$/cells/200 μl of complete RPMI media) were treated with CBE at 37° C. and 5% $CO_2$ for 72 hrs. These cells were stimulated in the presence and absence of GC (1 μg), anti-GC IgG (25 μg/ml), and GC (1 μg), +anti-GC IgG (25 μg) and supernatants were used to measure C5a concentrations by ELISA.

EXAMPLES

Figure 3A:
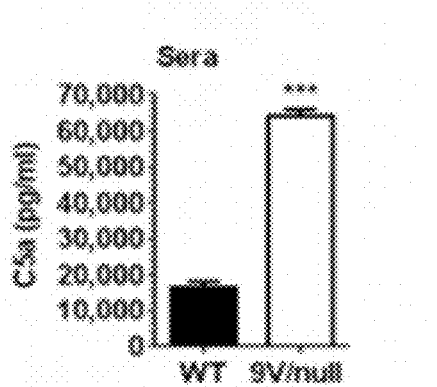
FIG. 3A-G. Strong local and systemic generation of C5a in 9V/null mice drives activation of APCs and T cells resulting in massive production of pro-inflammatory cytokines. C5a concentrations in serum (FIG. 3A) and supernatants of FACS-sorted MΦs and DCs (FIG. 3B) from lungs of WT (n=15) and 9 V/null mice (n=15). Expression of C5aR1 in dendritic cells (DCs) (FIG. 3C) and MΦs (FIG. 3D) from liver, spleen and lung of WT (black column) and 9V/null mice (white column); ΔMFI: C5aR1 MFI—isotype MFI. DCs (FIG. 3E) and CD4+T cells (FIG. 3F) purified from WT (n=15) and 9V/null mice (n=15) were stimulated with the indicated concentrations of C5a. After 24 hrs, CD40, CD80, and CD86 (DCs) and CD40L and CD69 (CD4+T cells) expression was determined by flow cytometry. Pulmonary DCs and CD4+T cells purified from WT (black columns) and 9V/null mice (white columns; n=15, each group) were co-cultured in the presence or absence of the indicated concentrations of C5a for 48 h. Cytokine concentrations were determined by ELISA. Values are the means±s.d. Asterisks show significant differences between WT and 9V/null mice (*$p<0.05$; $p<0.01$; *$p<0.001$).
Figure 3B:
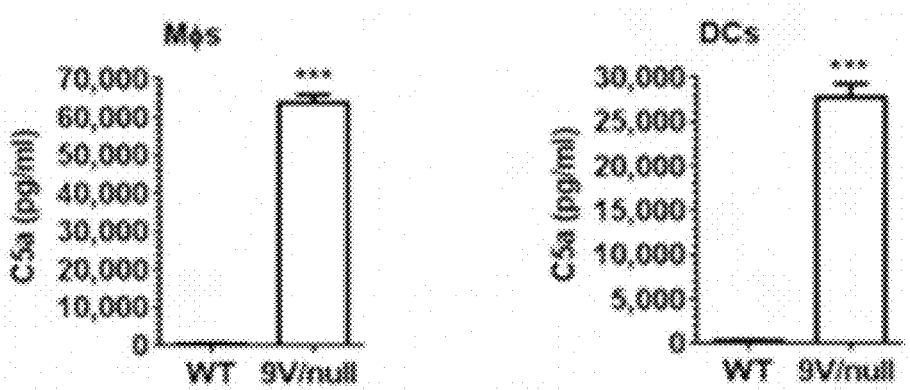
Figure 3C:
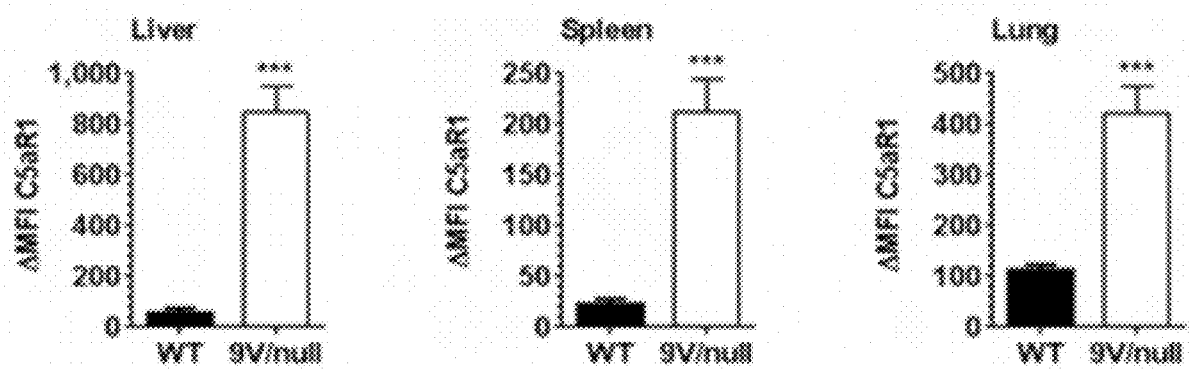
Figure 3D:
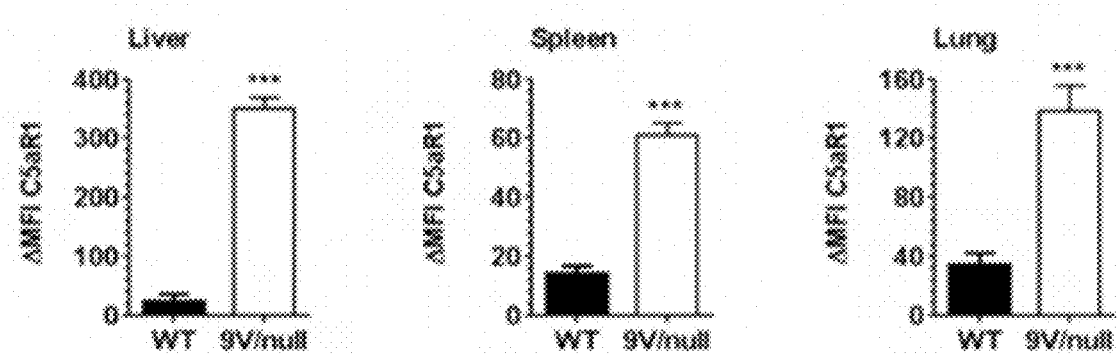
Figure 7A:
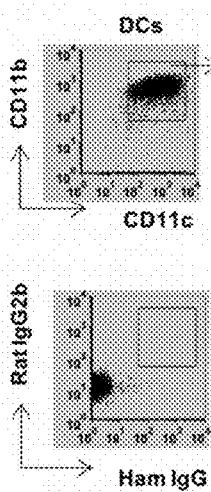
FIG. 7A-7D. Increased C5aR1 surface expression of tissue DCs and MΦs from 9V/null mice. FACS-sorted DCs and MΦs from liver, spleen and lung of strain-matched 9V/null and WT mice (n=15/each group) were analyzed for C5aR1 expression using C5aR1-specific antibodies. DCs were identified as $CD11c^+CD11b^+$ cells (FIG. 7A) and MΦs as $CD11b^+F4/80^+$ cells (FIG. 7C). Histograms showing C5aR1 expression in WT DCs (FIG. 7B) and MΦs (FIG. 7D) from WT (gray lines) and 9V/null (black lines) tissues. Light gray and carbon black-lined histograms depict corresponding isotype controls.
Figure 7B:
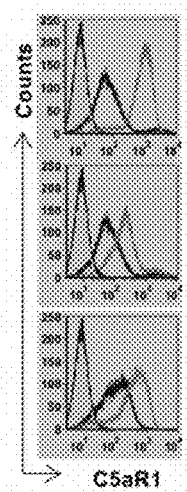
Figure 7C:
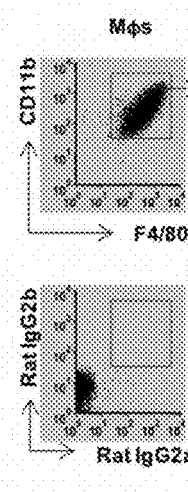
Figure 7D:
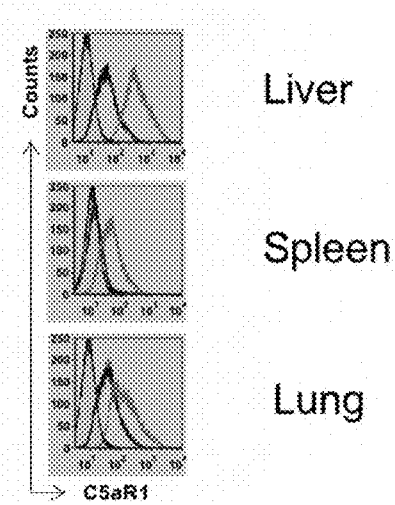

Given the pro-inflammatory environment in Gaucher disease, Applicant first determined whether this is associated with systemic and/or local complement activation in a mouse model of Gaucher disease (9V/null) continuing heteroallelic mutations in Gba1, a point mutation and a knockout (Asp409Val/knockout, i.e., 9V/null). Markedly elevated C5a levels were found in 9V/null sera compared with wildtype (WT) mice (FIG. 3A). Strikingly, purified $CD11b^+$ F4/80+ macrophages (MΦs) and $CD11c^+CD11b^+$ dendritic cells (DCs) (FIG. 3B) only from 9V/null produced C5a suggesting local C5 production and its proteolytic cleavage to C5a. This complement activation was associated with an increased C5aR1 expression on DCs (FIG. 3C, FIGS. 7A, 7B) and MΦs (FIG. 3D, FIG. 7C, 7D) of liver, spleen, and lung only from 9V/null mice. C5a is a small peptide of the complement anaphylatoxin family, which is cleaved from C5 upon canonical complement activation or non-canonical C5 cleavage by cell-derived proteases[10]. C5a exerts its pro-inflammatory effector function by binding to its two receptors C5aR1 and C5aR2, which both belong to large superfamily of seven transmembrane domain receptors.[11] Both receptors are widely distributed on immune cells including MOs, MΦs, neutrophils and DCs[12]. Locally produced C5a and the activation of the C5aR1 on DCs upregulates the expression of co-stimulatory molecules and drives the differentiation of and activation of $CD4^+$ T cells.[13].

Figure 3E:
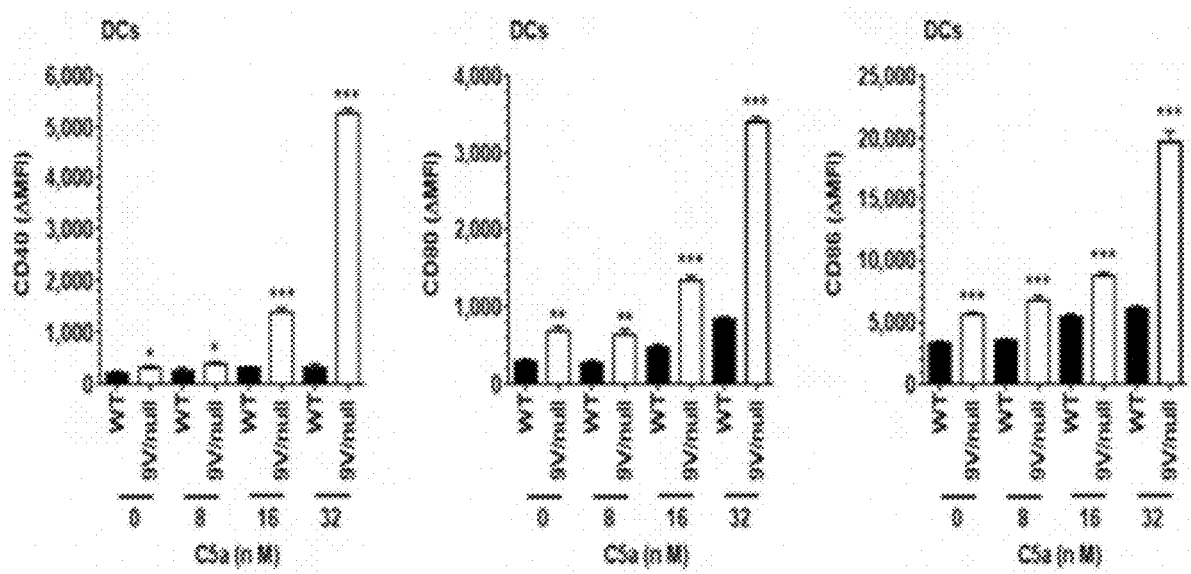
Figure 3F:
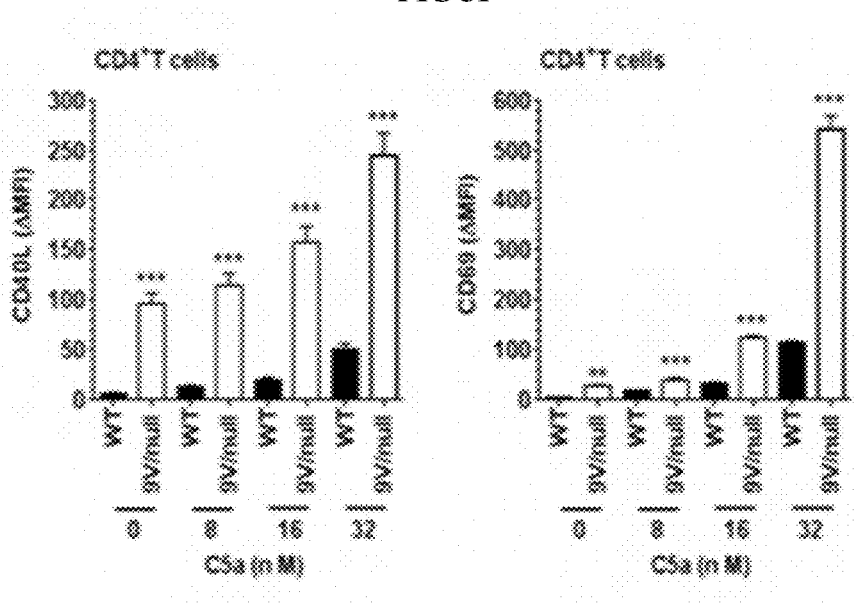
Figure 3G:
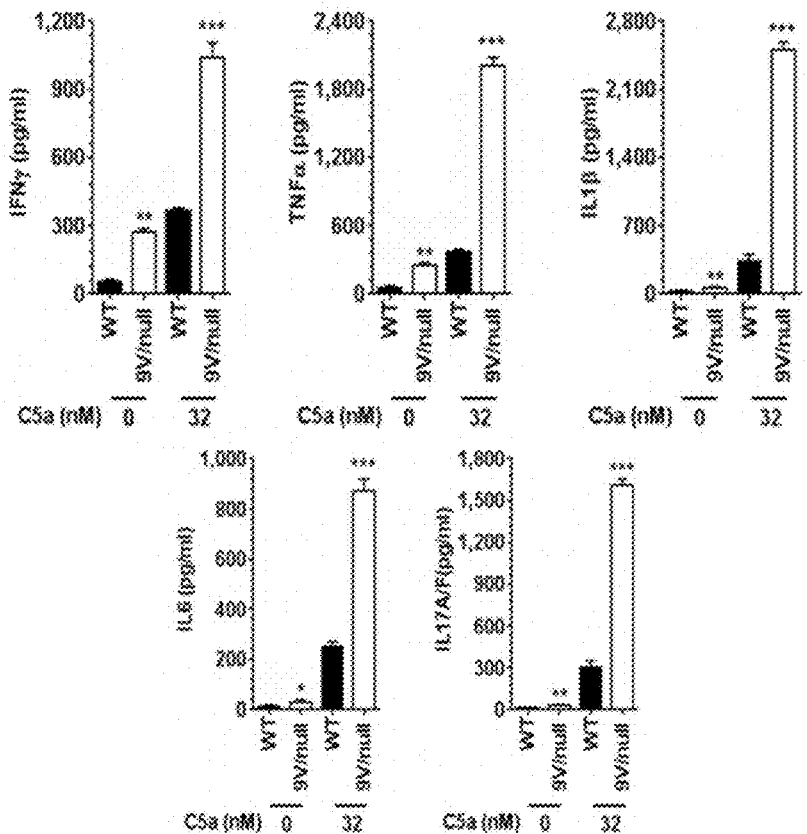
Figure 8A:
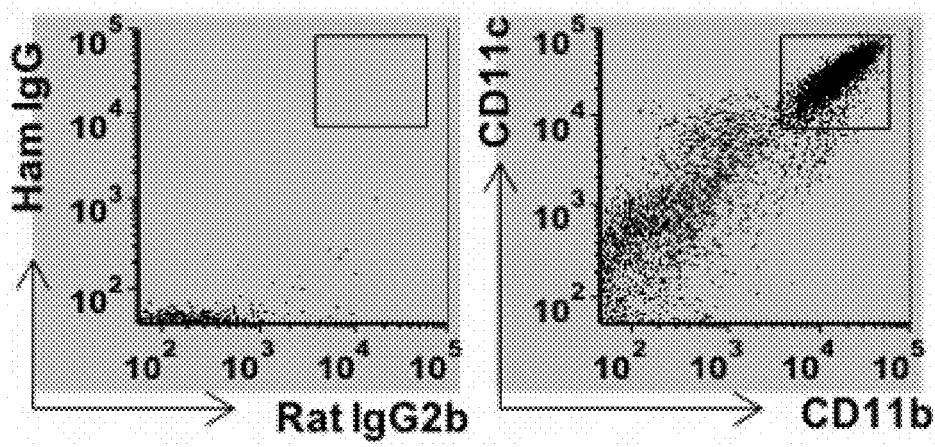
FIG. 8A-8D. C5a drives dose-dependent increases of co-stimulatory molecule expression in DCs and $CD4^+$ T cells from 9V/null mice. DCs and $CD4^+$T cells purified from WT and 9V/null mice (n=15/each group) were stimulated with increasing concentrations of C5a. After 24 hours, DCs (FIG. 8A) or $CD4^+$T cells (FIG. 8B) were identified as $CD11c^+CD11b^+$ or CD3+ $CD4^+$ cells. In the histograms (FIG. 8B, FIG. 8D), the light gray and carbon black lines correspond to WT and 9V/null cells, respectively. The light gray lines and carbon black fill are the corresponding isotypes. The results for DCs or $CD4^+$ T cells are shown in (FIG. 8B) and (FIG. 8D), respectively. $CD11c^+CD11b^+$ cells were stained with CD40, CD80, and CD86 specific antibodies (FIG. 8B). Similarly, $CD4^+$ T cells were stained with CD40L and CD69 specific antibodies (FIG. 8D).
Figure 8B:
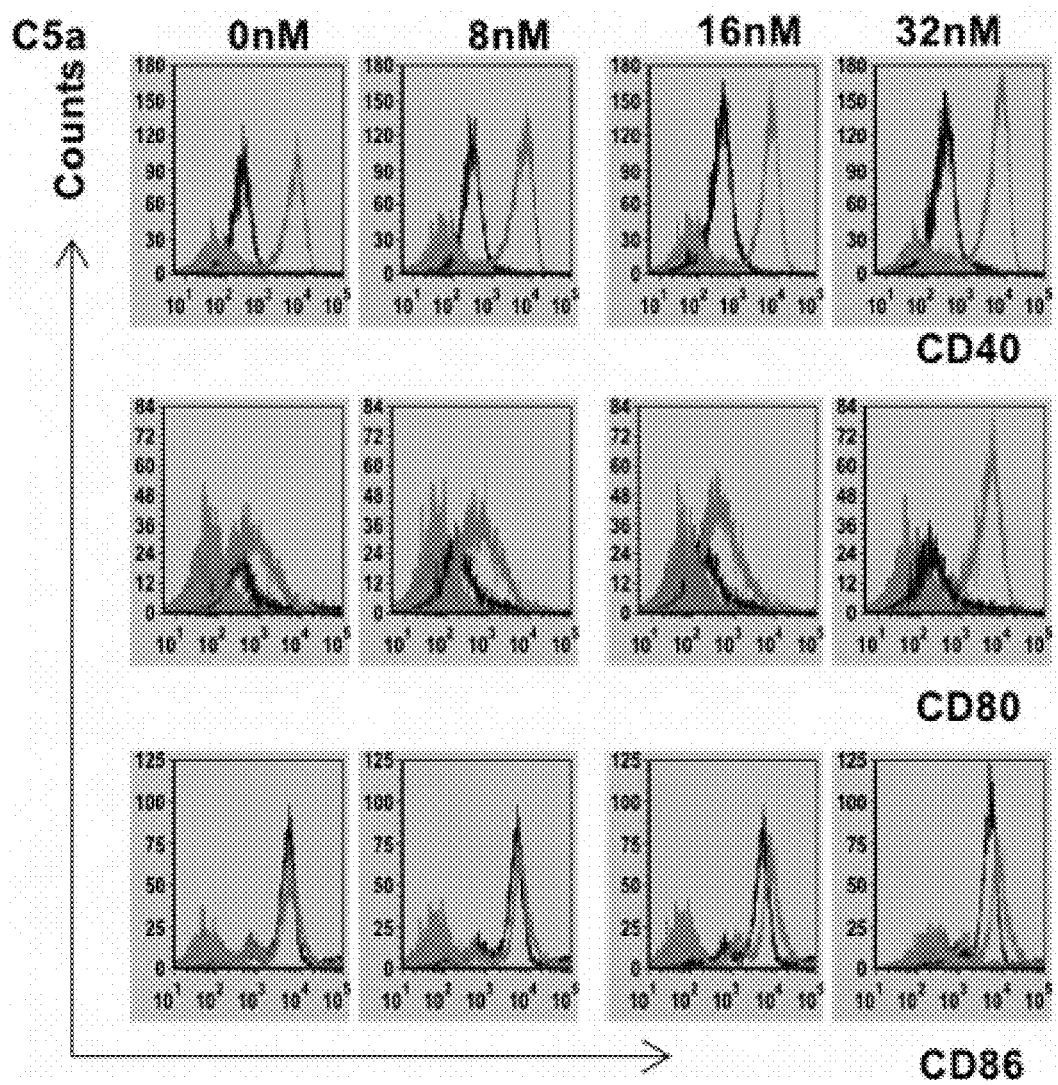
Figure 8C:
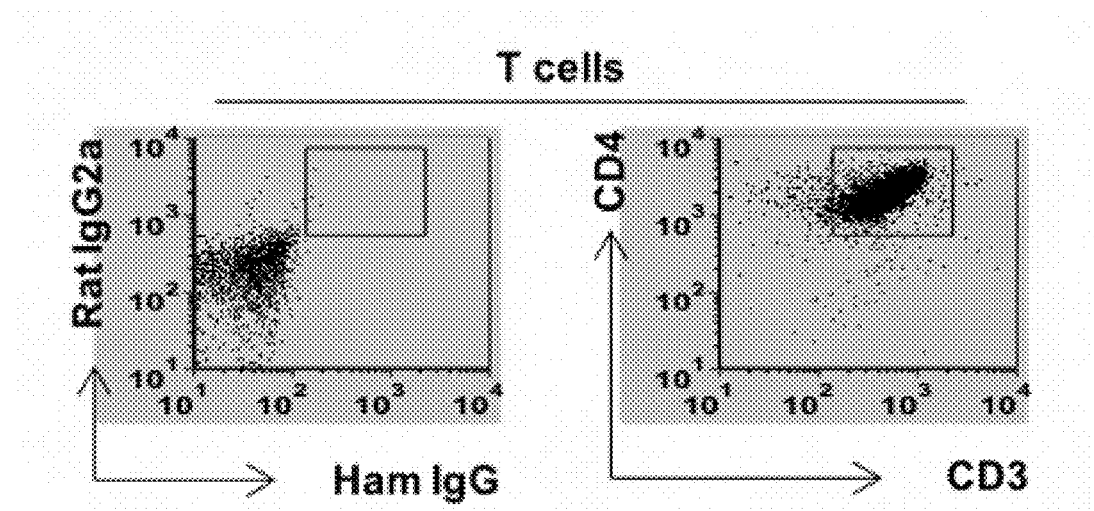
Figure 8D:
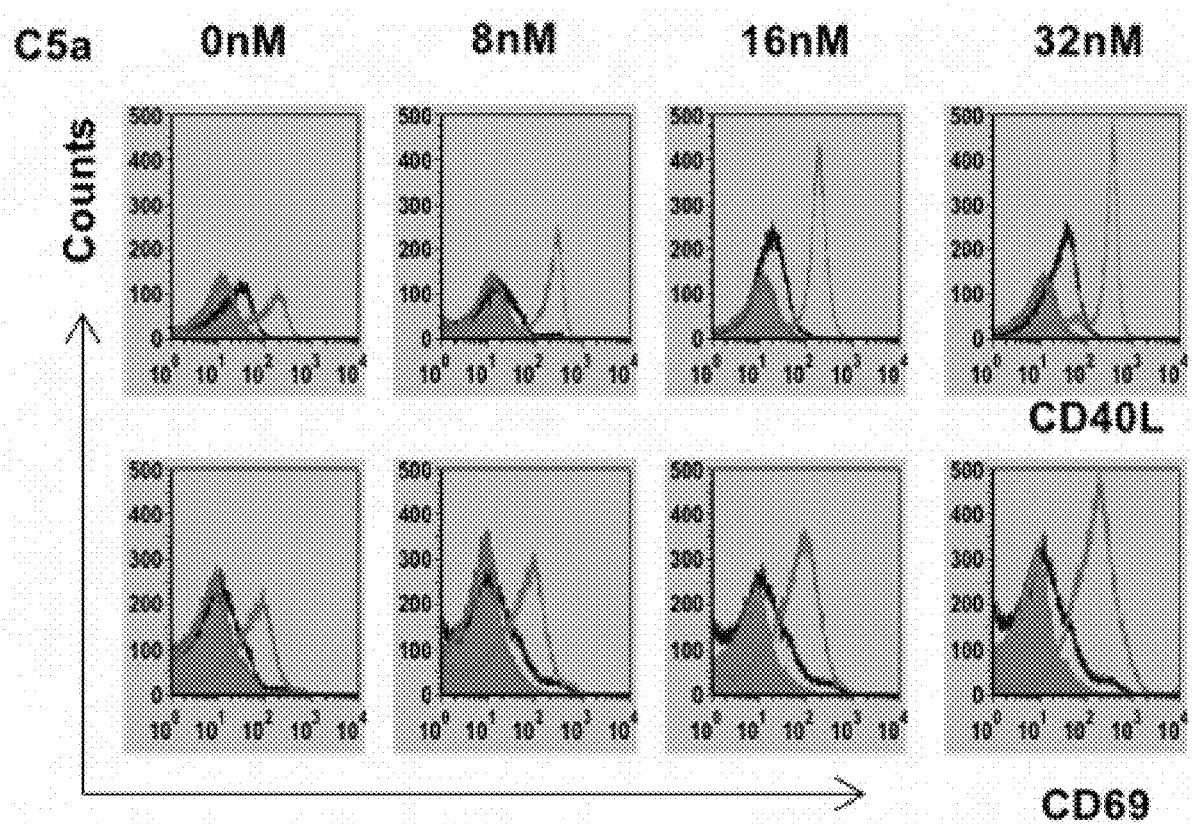

This strong complement activation led Applicant to determine the impact of C5a on the expression of the co-stimulatory molecules CD40, CD80, CD86 on pulmonary DCs and CD40 ligand (CD40L) and CD69 on spleen-derived $CD4^+$ T cells as C5a can modulate $DC^{14,15}$ and T cell responses[13]. C5a increased the expression levels of CD40, CD80, CD86 and CD40L and CD69 molecules in WT and 9V/null cells dose-dependently. However, compared with WT cells, the increases in 9V/null cells were significantly higher (FIG. 3E, 3F; FIG. 8A, 8D). These co-stimulatory molecules are critical for the activation and differentiation of T cells.[16] Co-cultures of purified pulmonary DCs and splenic $CD4^+$ T cells from WT and 9V/null mice in the presence or absence of C5a (32 nM) were used to evaluate the production of Th1/Th17 signature pro-inflammatory cytokines. C5a dramatically increased the production of IFN-γ, TNF-α, IL-1β, IL-6, and IL-17 of cells from 9V/null mice as compared with the WT counterparts (FIG. 3G). Taken together, these findings suggest that GC-induced C5a is critical for the development of tissue inflammation in response to the 9V/null GCase deficiency.

Figure 4C:
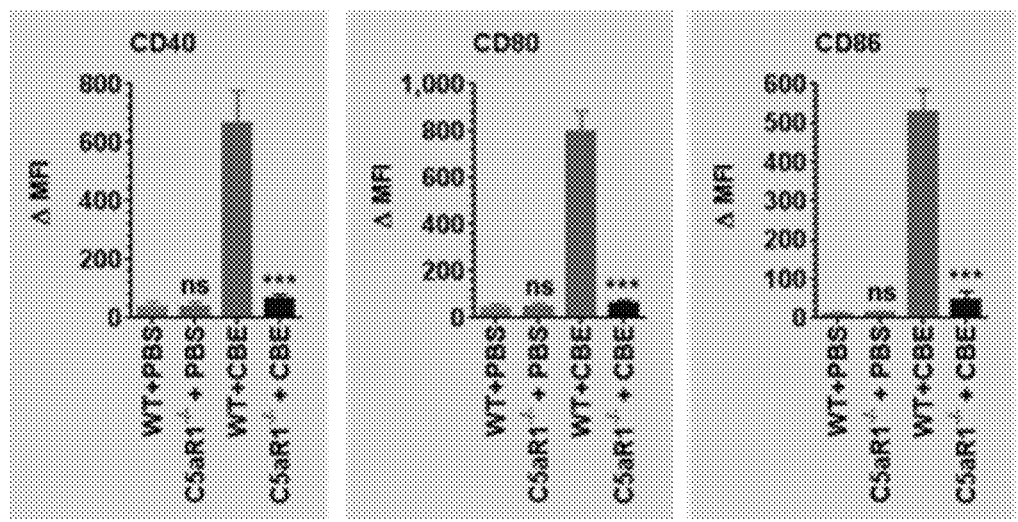
Figure 4D:
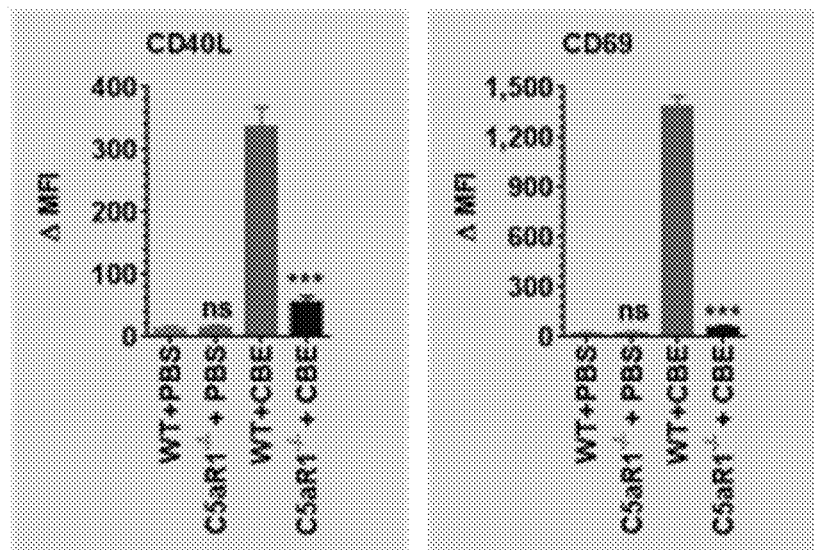
Figure 4E:
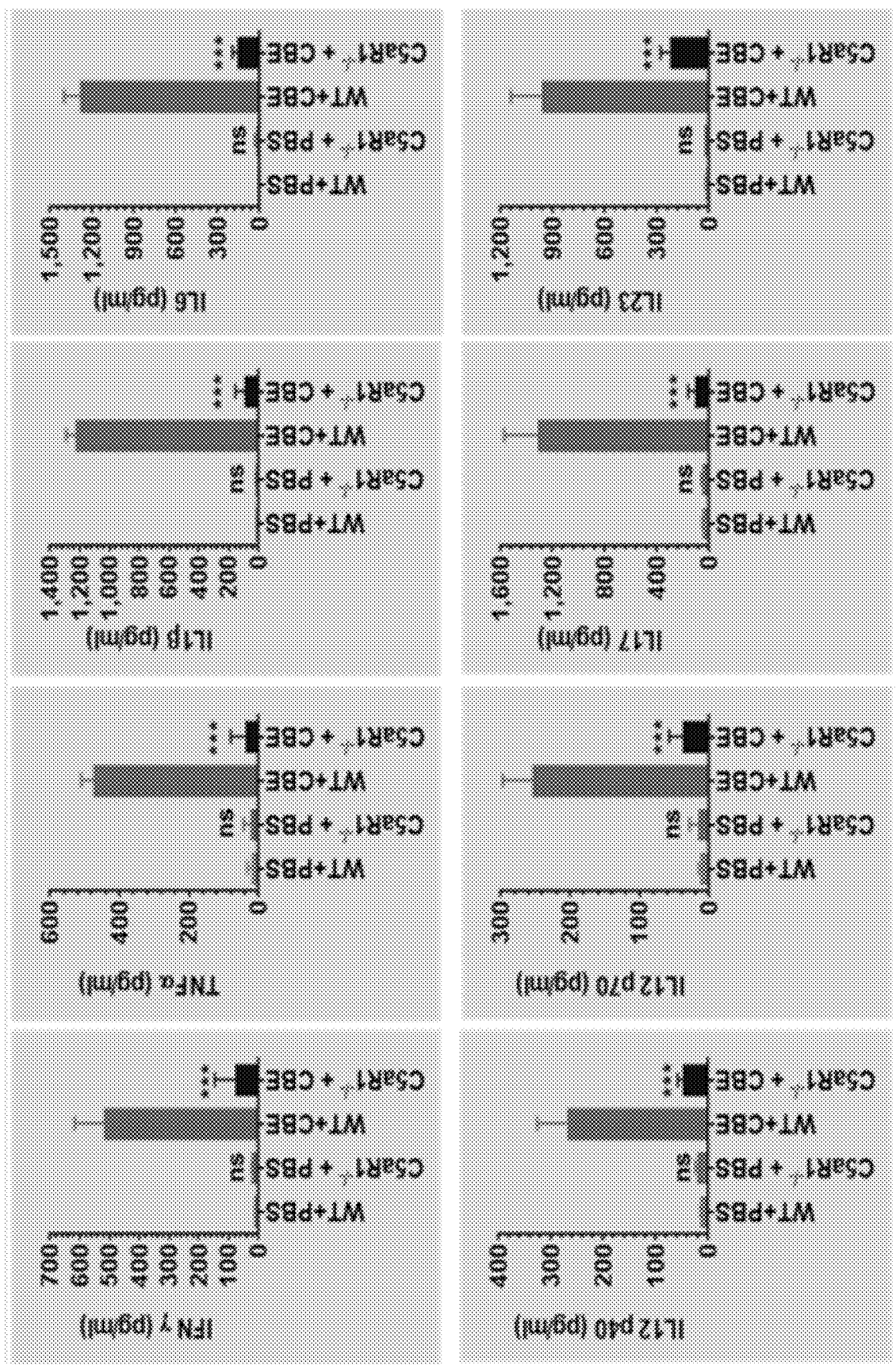
Figure 9A:
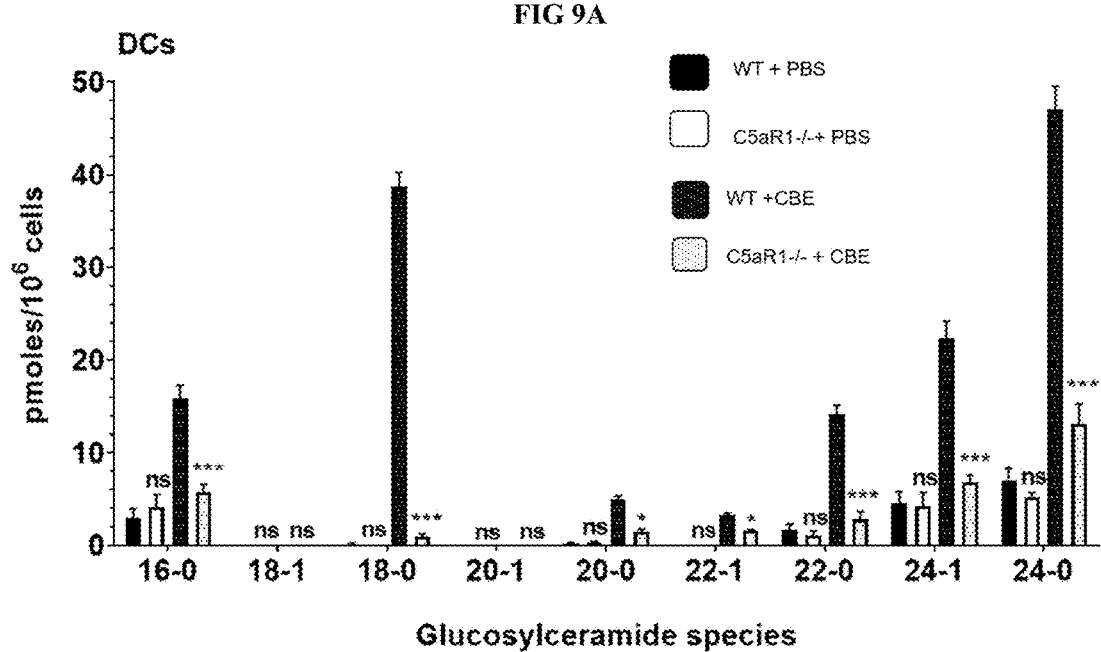
FIG. 9A-9E. CBE-treated C5aR1 mice showed decreases of cellular GC, reduced costimulatory molecules expression in DCs and $CD4^+$ T cells and low serum levels of cytokines and chemokines. GCs were extracted and quantified (see Materials and Methods) from FACS-sorted DCs (FIG. 9A) and $CD4^+$ T cells (FIG. 9B) isolated from mouse lungs of vehicle treated WT (light gray, n=10) and $C5aR1^{-/-}$ (carbon black, n=10) as well as CBE-treated WT (dark gray, n=10) and CBE-treated $C5aR1^{-/-}$ mice (black, n=10). The total GCs were normalized to $1×10^6$ of each cell type. $CD11c^+CD11b^+$ DCs (FIG. 9C) were assessed for CD40, CD80 and CD86 expression; $CD4^+$ T cells were stained for CD40L and CD69 (FIG. 9D). Histogram colors for each cell type correspond to those indicated for GC analyses.
Figure 9B:
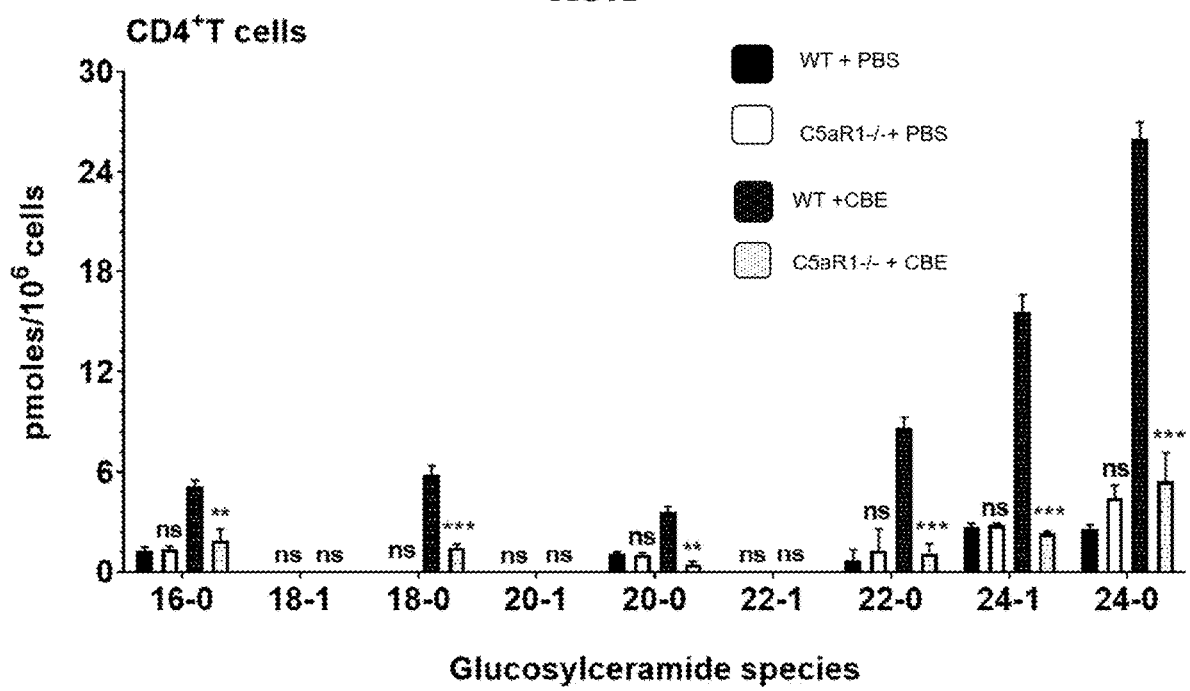
Figure 9D:
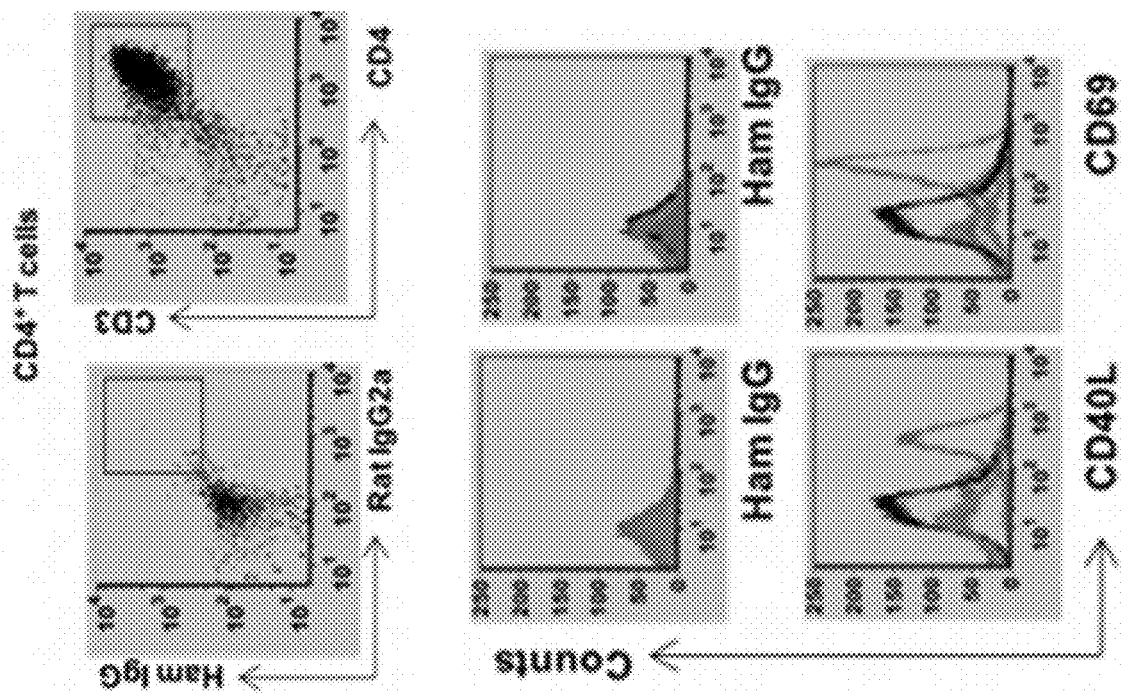
Figure 9C:
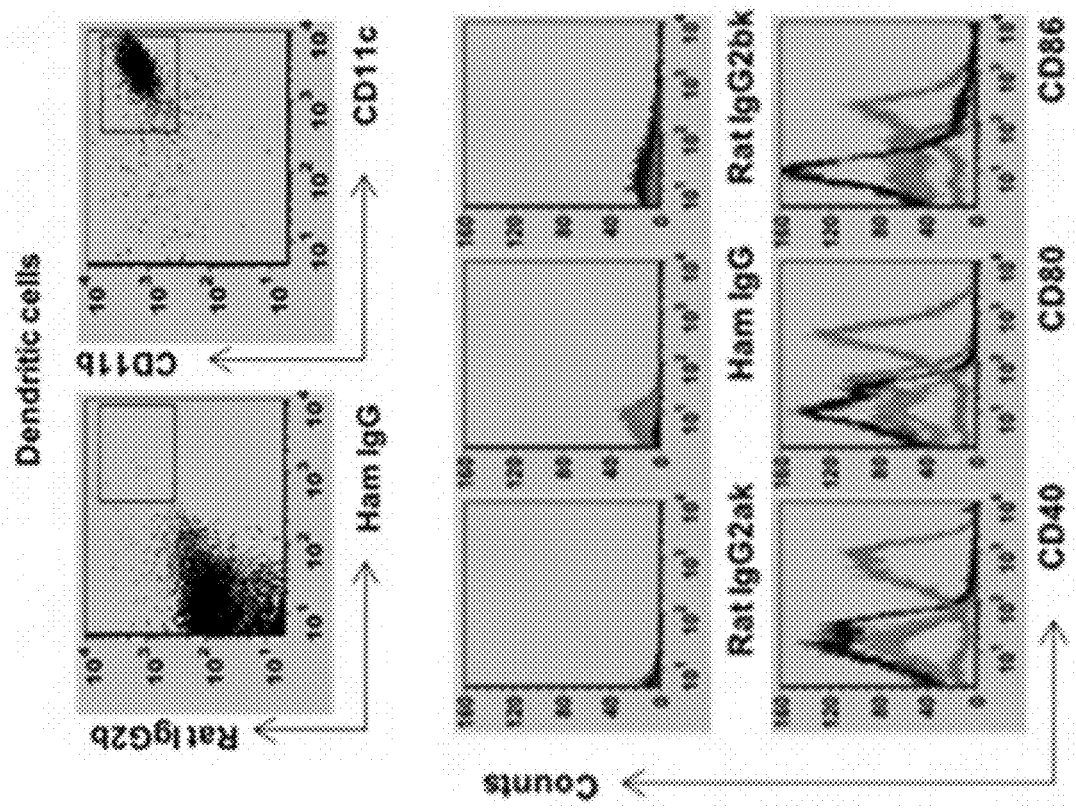
Figure 9E:
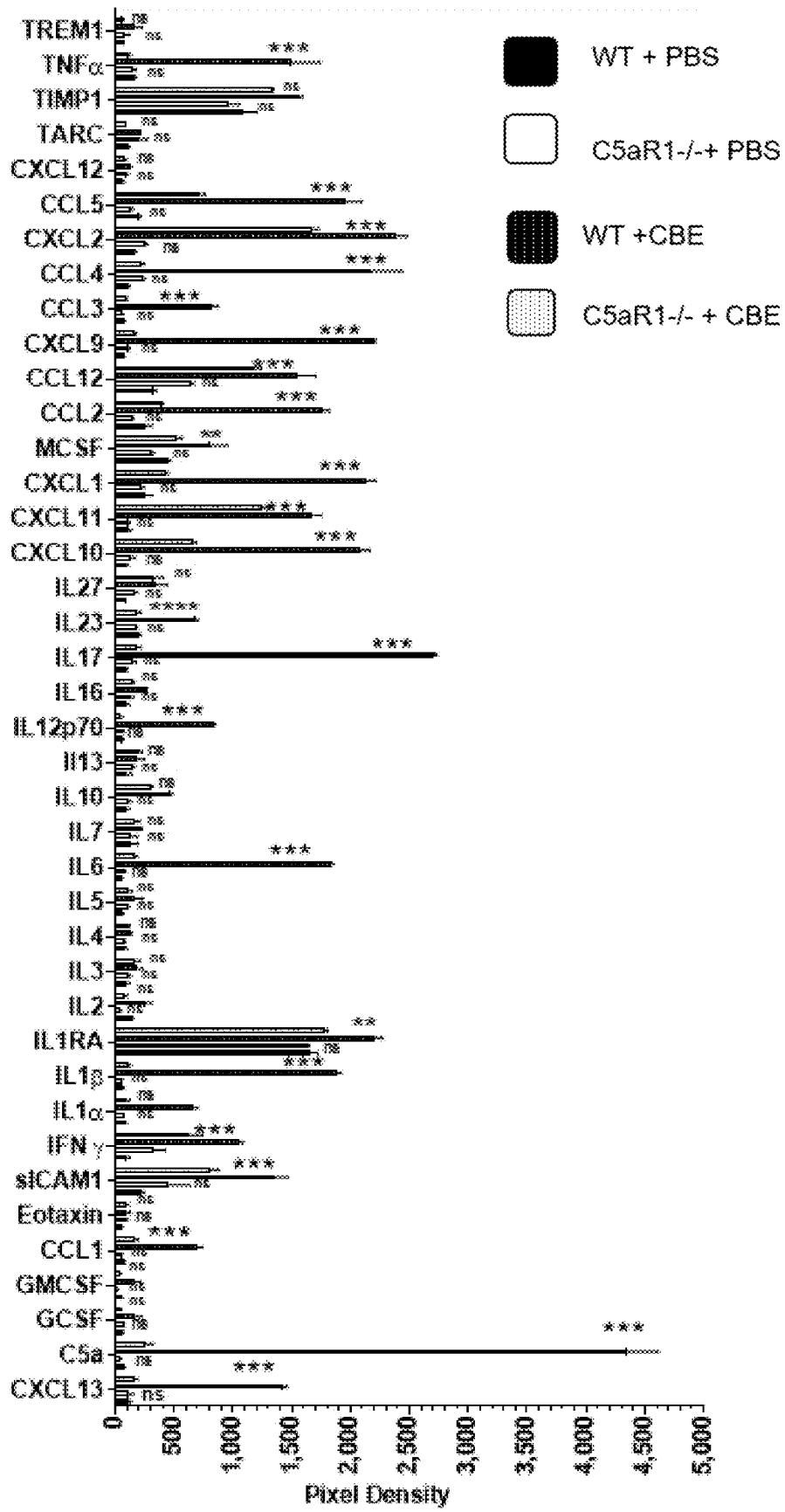
Figure 10A:
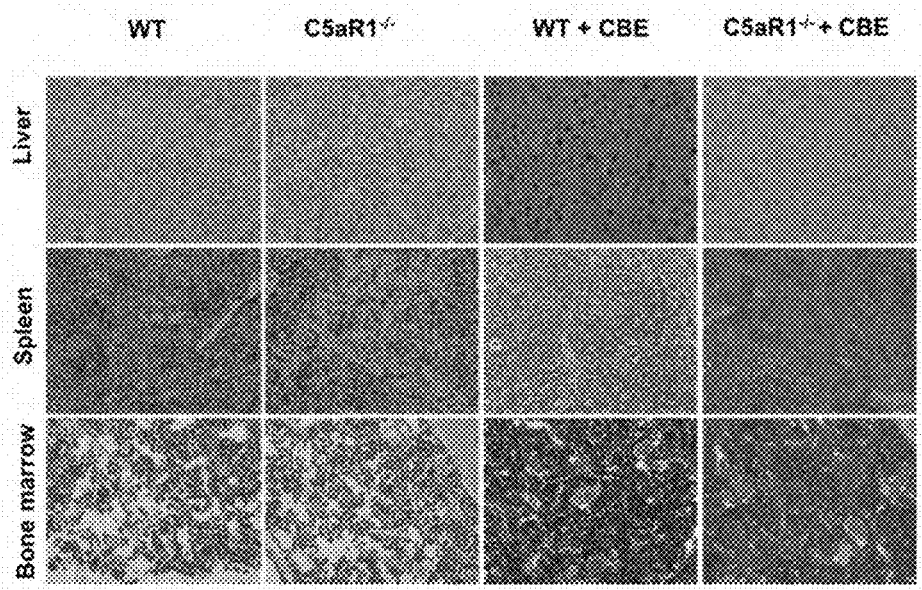
FIG. 10A-10E. CBE-treated $C5aR1^{-/-}$ mice show decreased cellularity, tissue disruption, and lower numbers of APCs and T cells.
Figure 10B:
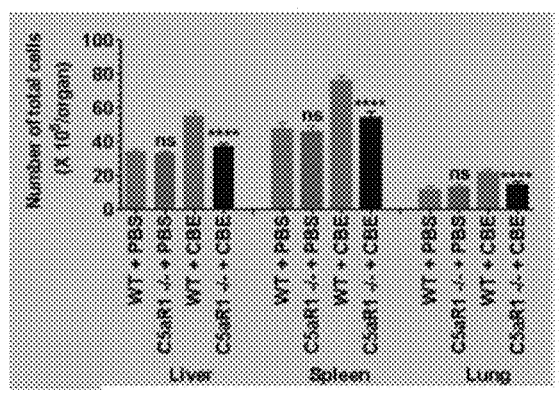
Figure 10C:
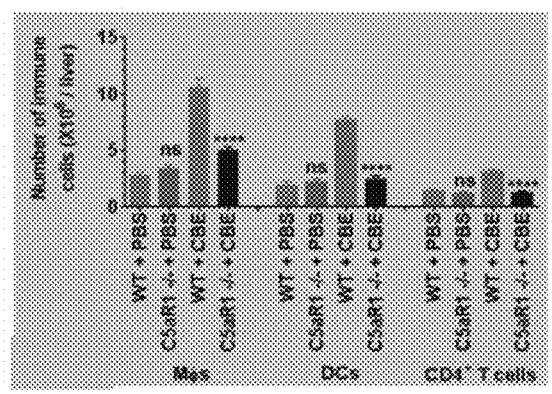
Figure 10D:
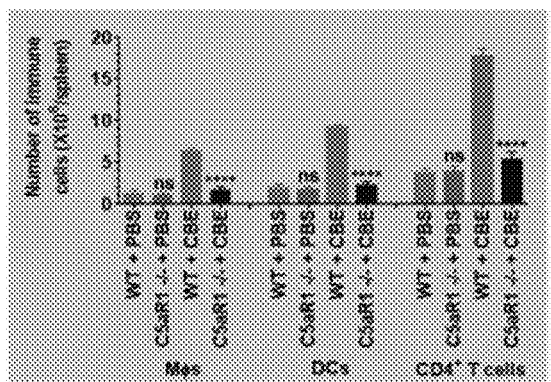
Figure 10E:
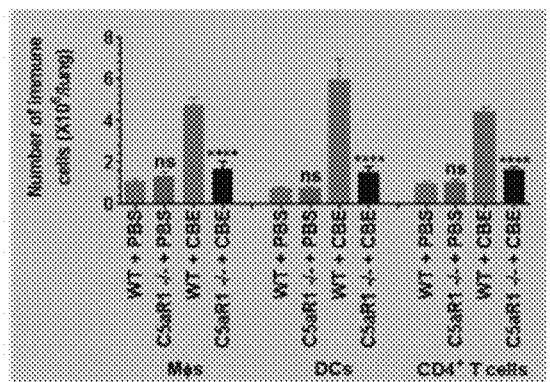

C5a binds to two distinct receptors, i.e. C5aR1 and C5aR211. Therefore, the role of C5a in vivo was ascertained by conduritol B epoxide (CBE)-induction of GCase deficiency in WT, $C5aR1^{-/-}$, and $C5aR2^{-/-}$mice. CBE is a covalent active site-directed inhibitor of GCase. All WT and $C5aR2^{-/-}$ mice showed severe signs of disease and died after 29-35 days of daily CBE injections (FIG. 4A). In WT (FIG. 4; FIG. 9) and $C5aR2^{-/-}$ (data not shown) mice, disease development was associated with a massive accumulation of several GC species in pulmonary MΦs (FIG. 2b), DCs and splenic CD4+ T cells (FIG. 9A, 9B), upregulation of costimulatory molecules on pulmonary DCs (FIG. 4C) and $CD4^+$ T cells (FIG. 4D; FIG. 9C, 9D), and high serum levels of pro-inflammatory cytokines (FIG. 4E). The massive accumulation of GC species was associated with tissue damage in liver, spleen and bone marrow (BM) as evidenced by disrupted vascular and stromal tissues (FIG. 10A) as well as increased tissue cellularity, in particular with high numbers of APCs and $CD4^+$ T cells (FIG. 10B-10E). In comparison, even after daily injections of CBE for 60 days, all $C5aR1^{-/-}$ were clinically healthy and survived (FIG. 4A). There was markedly less GC storage in pulmonary MΦs (FIG. 4B), DCs and splenic $CD4^+$ T cells (FIG. 9A, 9B), lower expression of costimulatory molecules on DCs and $CD4^+$ T cells (FIG. 4C, 4D; FIG. 9C, 9D), and only minor systemic production of pro-inflammatory cytokines (FIG. 4E). Also, tissue inflammation (FIG. 10A) and the accumulation of APCs and $CD4^+$ T cells (FIG. 10B-10E) were markedly reduced in CBE-treated $C5aR1^{-/-}$ mice.

Figure 5A:
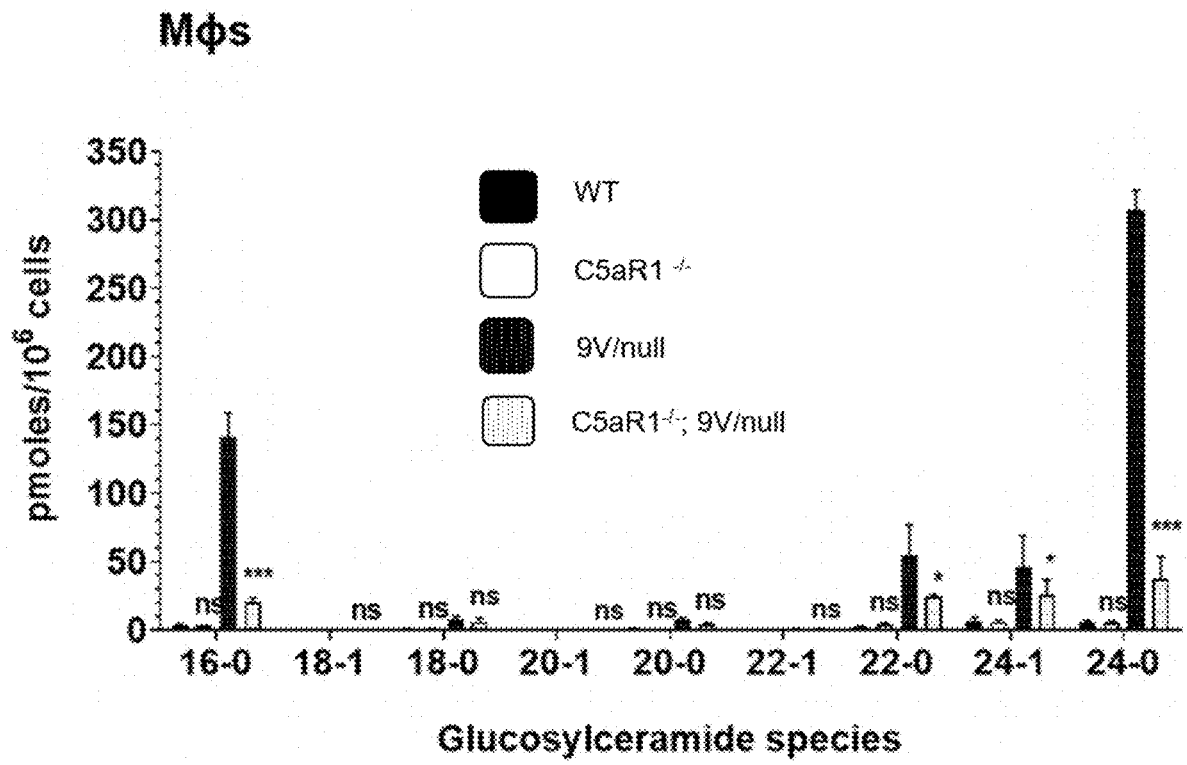
FIG. 5A-5I. C5aR-targeting in Gaucher disease-prone 9V/null mice protects from GC accumulation and inflammation.
Figure 5B:
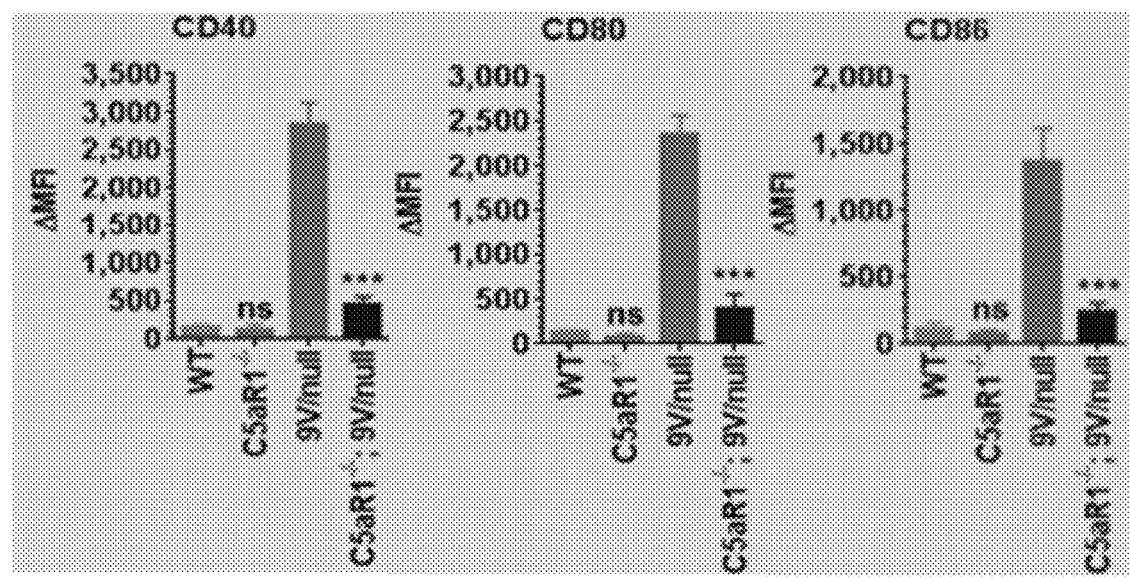
Figure 5C:
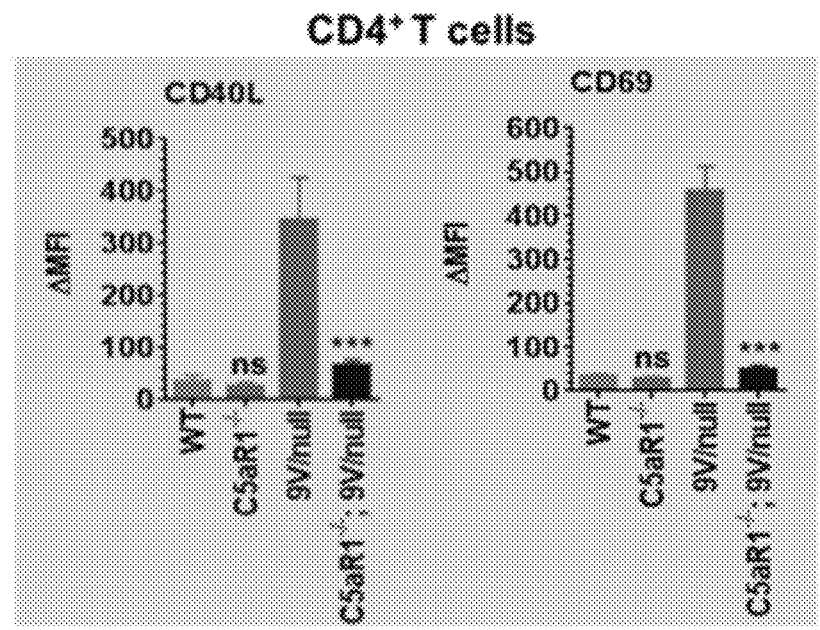
Figure 5D:
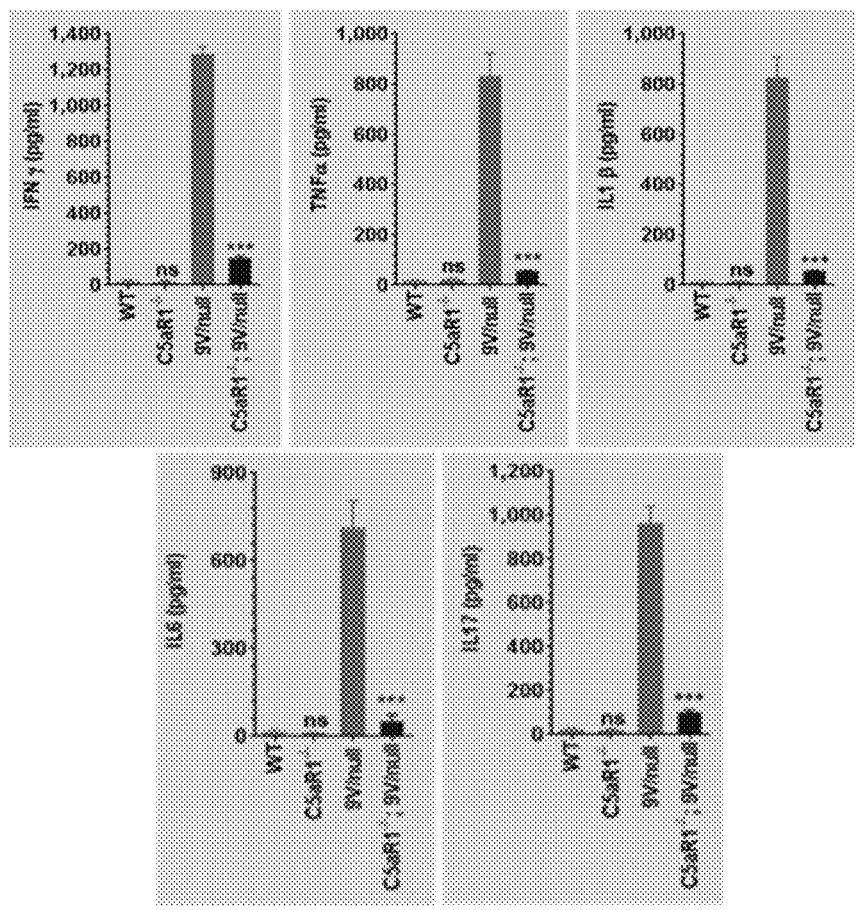
Figure 11A:
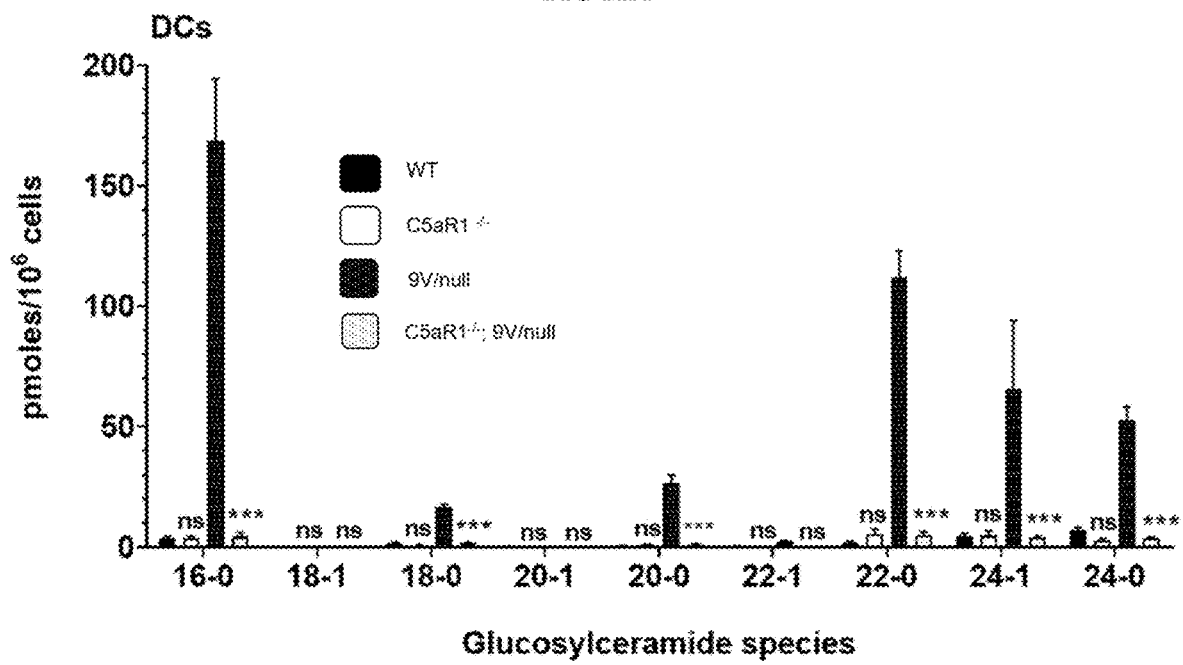
FIG. 11A-11D. 9V/null; C5Ra1$^{-/-}$ mice show decreased levels of GC and decreased costimulatory expression in pulmonary DCs and CD4$^+$ T cells. GCs were extracted and quantified from FACS-sorted lung DCs (FIG. 11A) and CD4$^+$ T cells (FIG. 11B) of WT (light gray, n=15) and C5aR1$^{-/-}$ mice (carbon black, n=15) as well as 9V/null, (dark gray, n=15) and 9V/null; C5aR1$^{-/-}$ mice (black, n=15). The total GCs in each cell types were normalized to 1×10 cells. Pulmonary CD11c$^+$CD11b$^+$ cells (FIG. 11C) were assessed for CD40, CD80 and CD86 expression and CD4$^+$ T cells (FIG. 11D) were stained for CD40L and CD69. Histogram colors for each cell type correspond to those indicated for GC analyses. Data are the means±s.d. Group comparisons were done by ANOVA with the a priori comparison being C5aR1-deficient to non-deficient. For each experiment, two different mouse strains were evaluated (WT or 9V/null), thus the Bonferroni corrected significance threshold is 0.025 (p<0.01, *p<0.001).
Figure 11B:
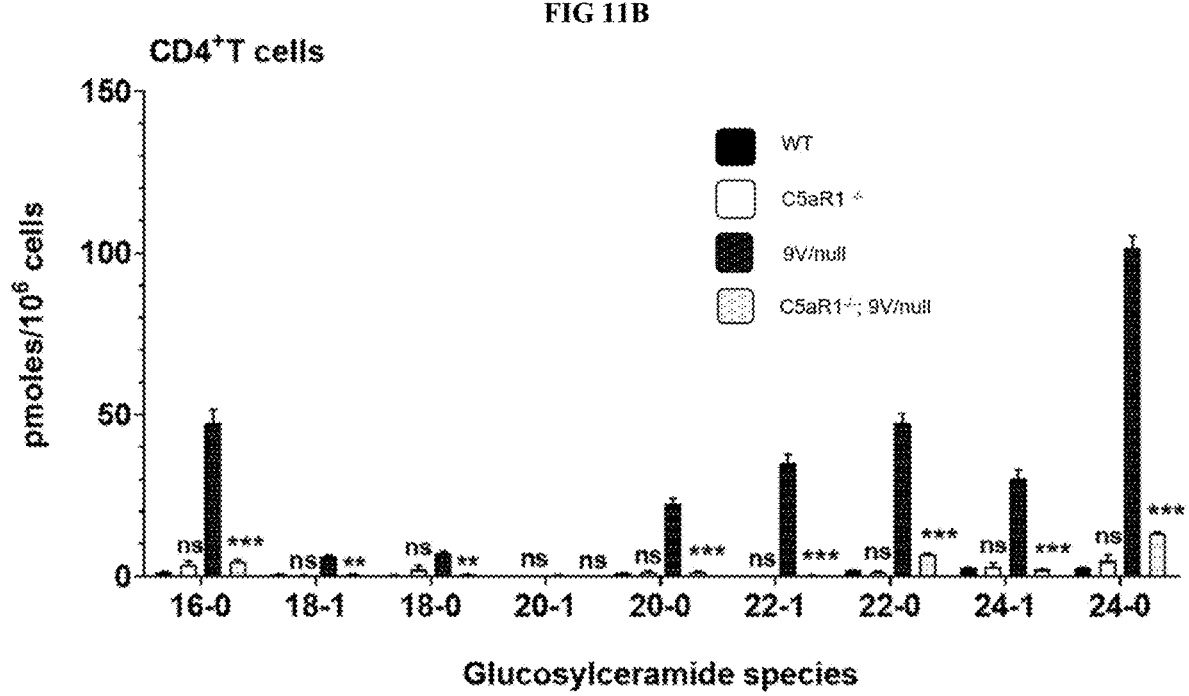
Figure 11C:
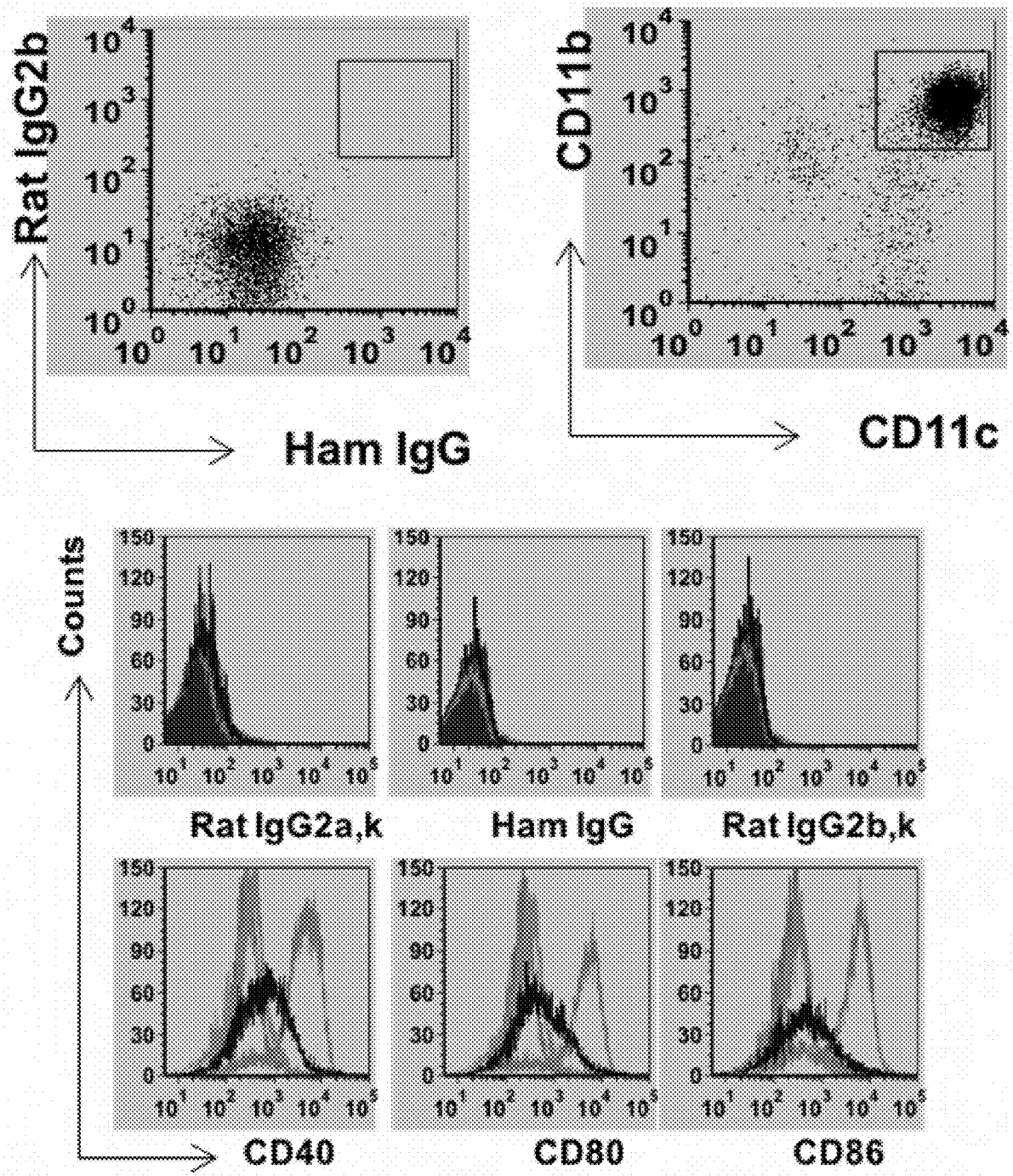
Figure 11D:
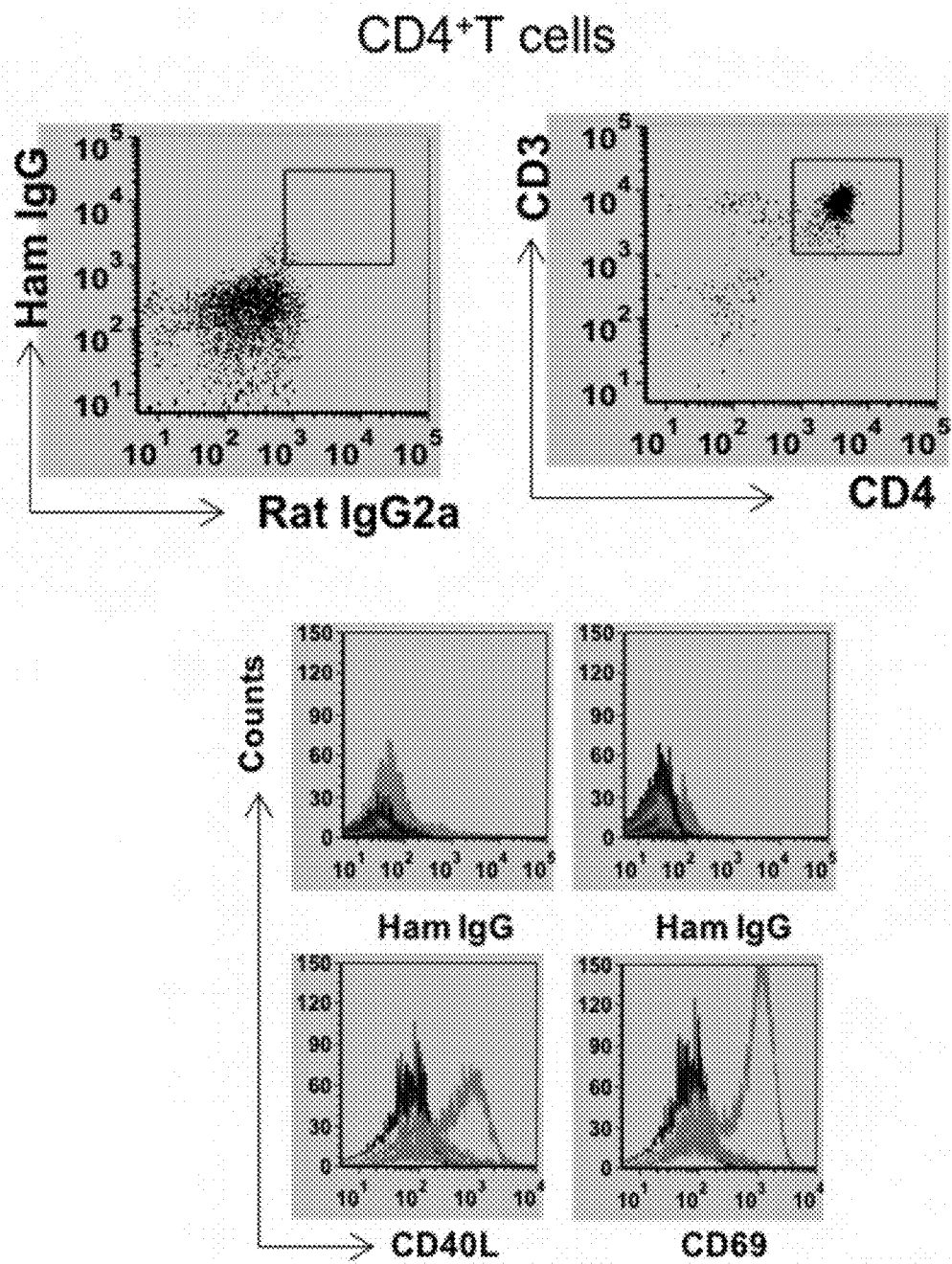

To directly assess the role of the C5a/C5aR1 axis in Gaucher disease development, 9V/null mice were back-crossed to the $C5aR1^{-/-}$ background to generate 9V/null; $C5Ra1^{-/-}$ mice. Similar to the CBE-induced GCase deficiency, 9V/null; $C5Ra1^{+/+}$ mice showed excess GC accumulation in pulmonary MΦs (FIG. 5A), DCs (FIG. 11A) and splenic $CD4^+$ T cells (FIG. 11B) as compared with 9V/null; $C5aR1^{-/-}$ mice. The expression of co-stimulatory molecules on the surface of 9V/null; $C5aR1^{-/-}$ DCs and $CD4^+$ T cells was significantly lower than that in cells from 9V/null; $C5aR1^{+/+}$ mice (FIG. 5B, 5C; FIG. 11C, 11D). Further, co-cultures of pulmonary DCs and spleen-derived $CD4^+$ T cells from 9V/null; $C5aR1^{-/-}$ mice resulted in a much lower pro-inflammatory cytokine production than observed in their $C5aR1^{+/+}$ counterparts (FIG. 5D).

Figure 5E:
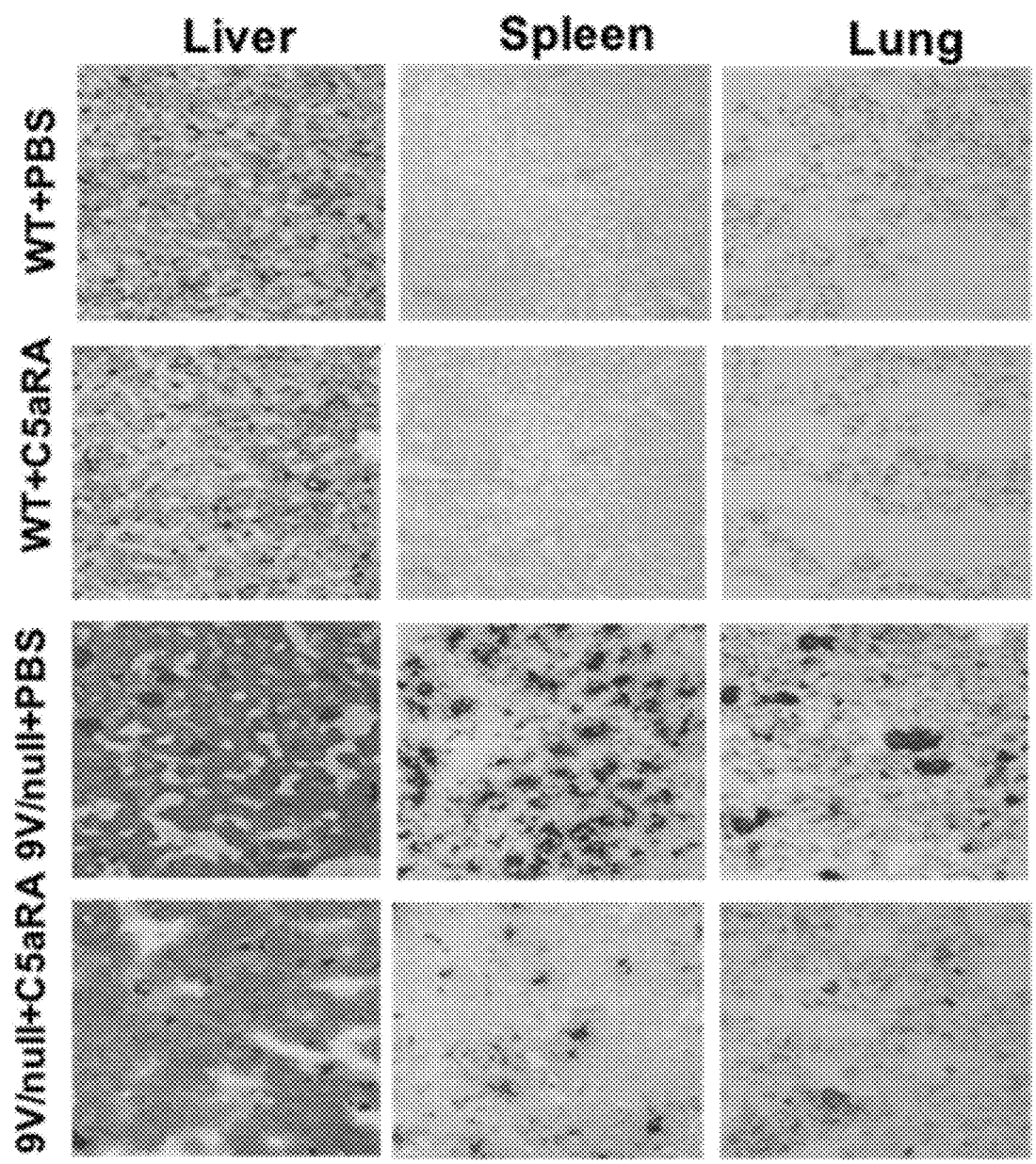
Figure 5F:
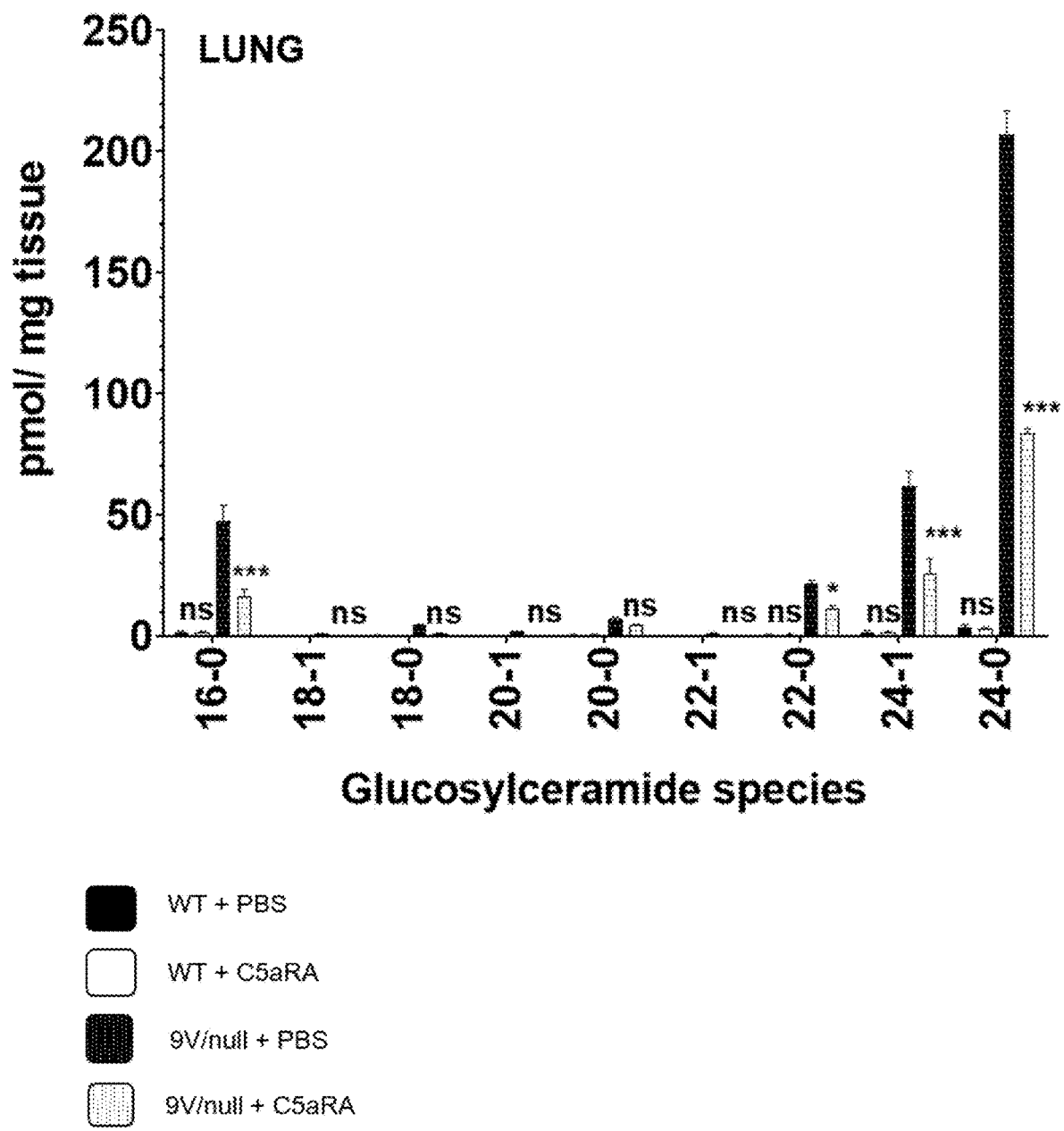
Figure 5G:
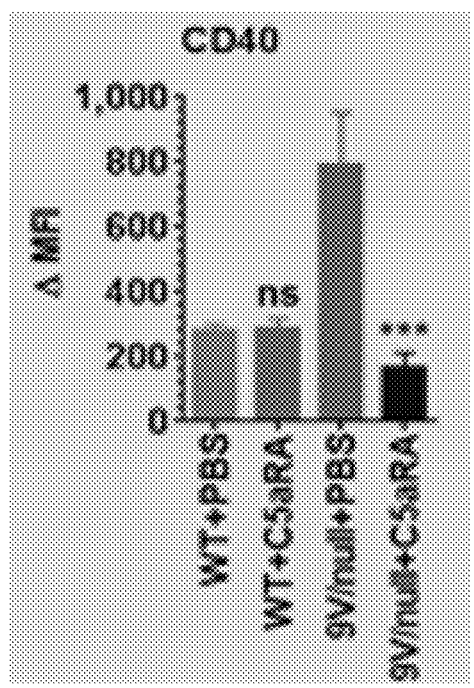
Figure 5H:
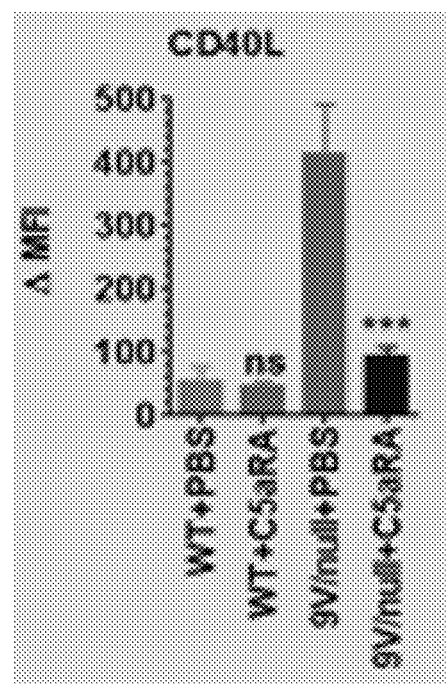
Figure 5I:
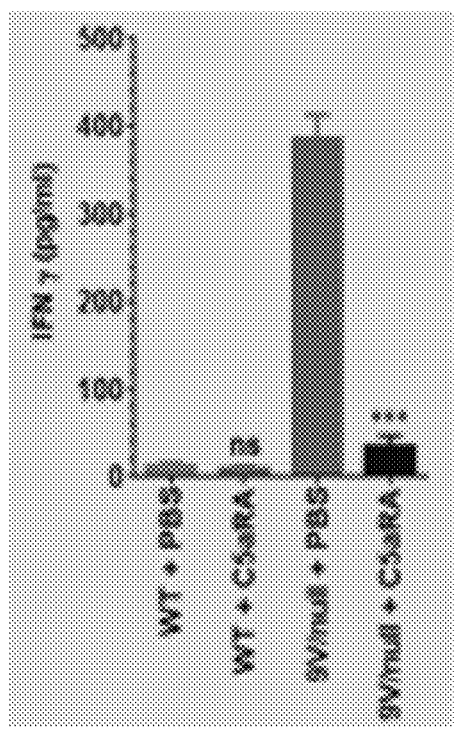
Figure 5I:
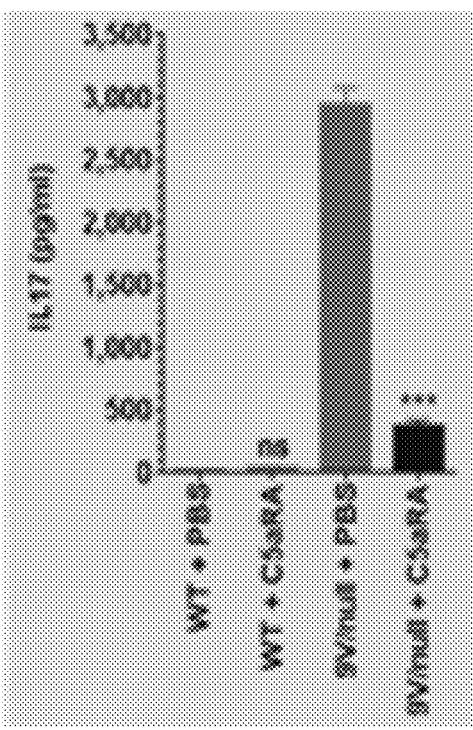
Figure 12E:
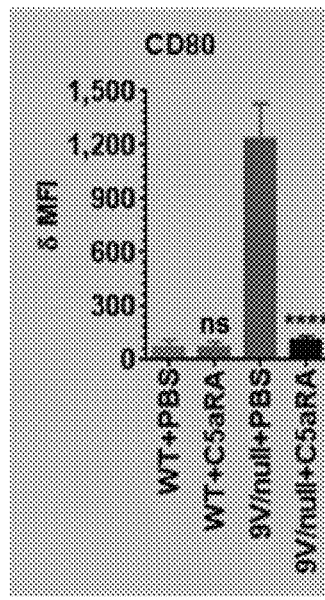
Figure 12F:
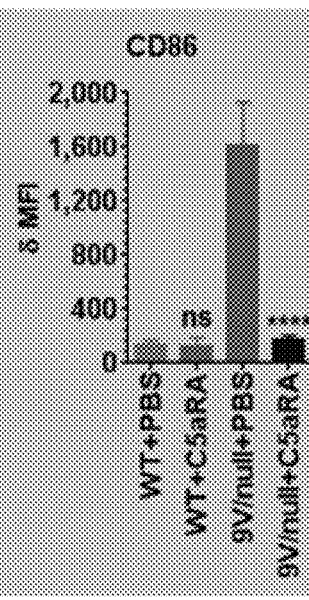
Figure 12G:
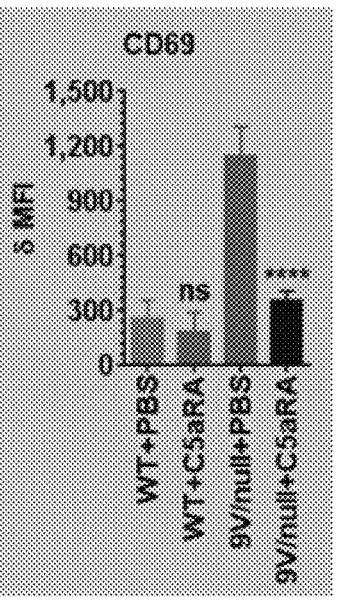
Figure 12H:
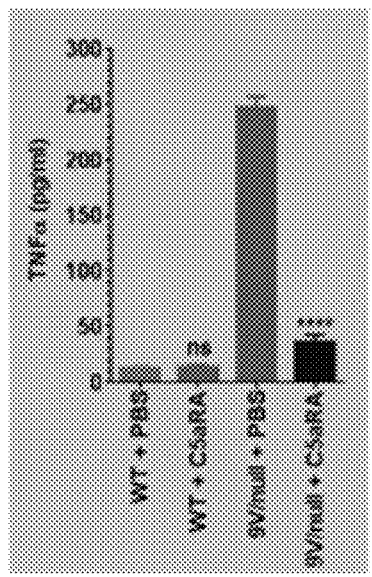
Figure 12H:
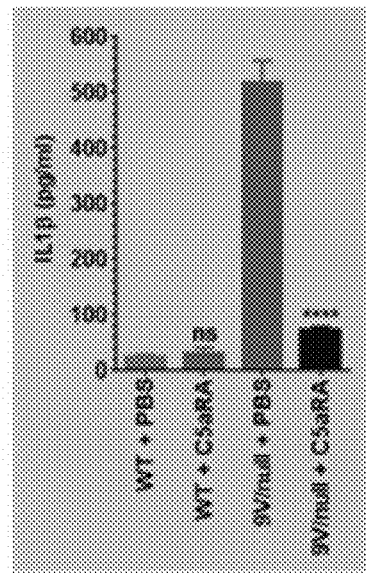
Figure 12H:
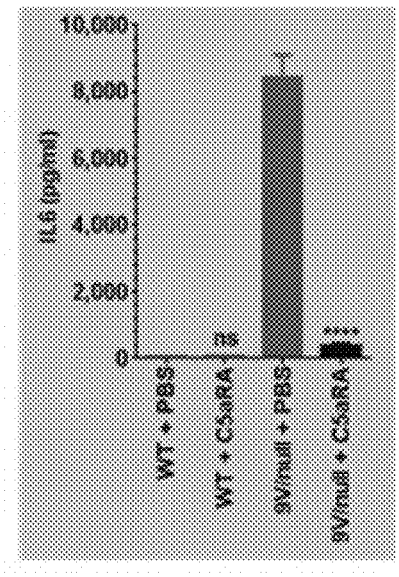

To determine the potential of pharmacological C5aR1 targeting in Gaucher disease, the C5aR antagonist $A8^{A71-73}$ (C5aRA) or vehicle (PBS) was injected i.p. into WT and 9V/null mice. In C5aRA-treated 9V/null mice, MΦ infiltration of the lung, liver and spleen was substantially reduced (FIG. 5E). Further, compared to vehicle-injected 9V/null mice, GC storage in lung (FIG. 5F), liver (FIG. 12A) and spleen (FIG. 12B) of C5aRA-treated 9V/null mice was significantly decreased. Also, in response to C5aRA treatment, CD40 (FIG. 5G), CD80 and CD86 expression in pulmonary DCs (FIG. 12C, E, F) and CD40L (FIG. 5H) and CD69 in $CD4^+$ T cells (FIG. 12D, 12G) was significantly reduced. Finally, markedly decreased IFN-γ, IL-17 (FIG. 6I), TNF-α, IL-1 and IL-6 (FIG. 12H) production was also found in response to C5aR1 targeting with C5aRA.

Figure 6A:
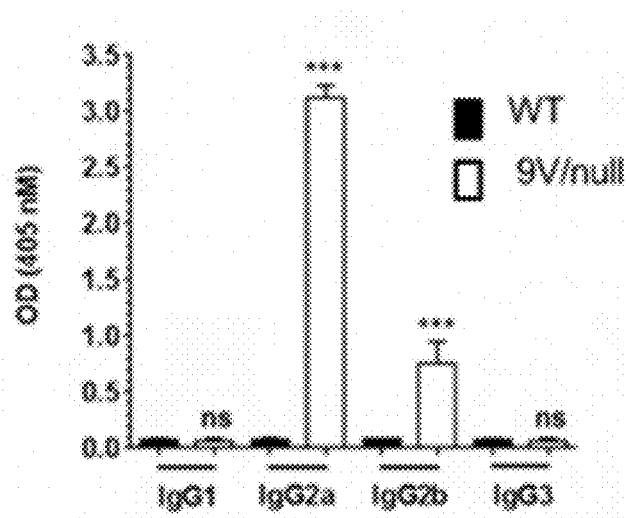
FIG. 6A-6J. Formation of GC-specific IgG autoantibodies in 9V/null mice and Gaucher disease patients that drive local and systemic C5a generation.
Figure 6B:
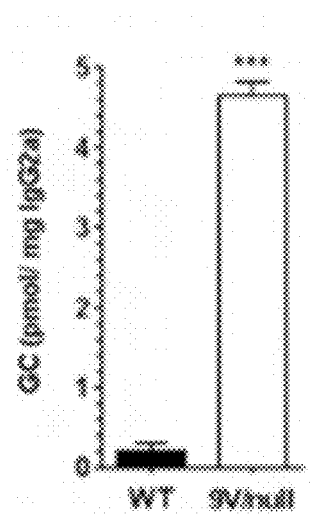
Figure 13:
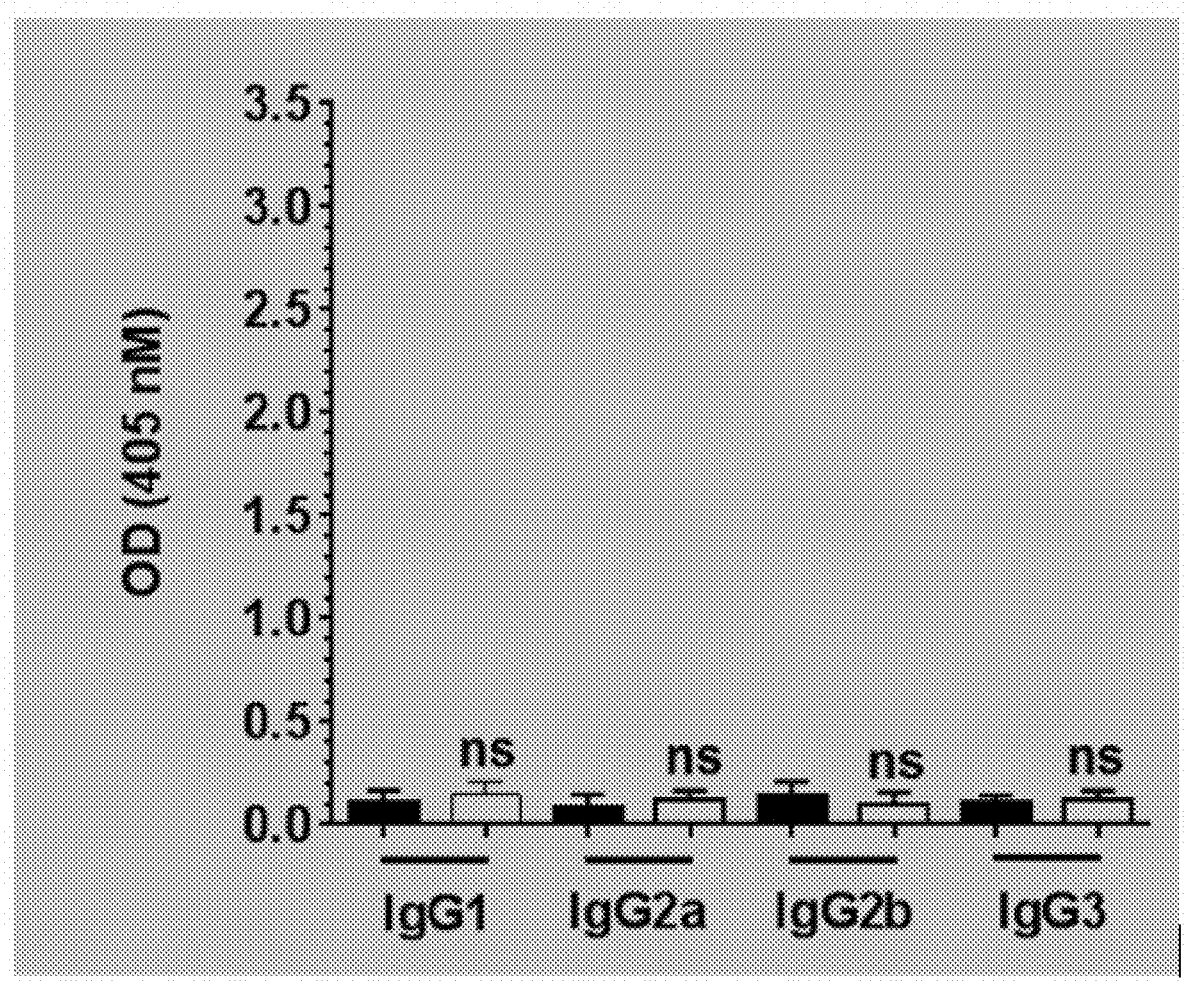
FIG. 13. 9V/null mouse IgG isotypes do not cross react with glucosyl sphingosine. Glucosyl sphingosine specific IgG1, IgG2a, IgG2b, and IgG3 antibodies in serum of WT (n=15, black column) and 9V/null mice (n=15, white column) were determined by ELISA. Values are the mean±s.d. Group comparisons were done by ANOVA FIG. 14A-14C. Increased IgG auto-antibodies to GC, strong tissue deposition of C3b and high serum levels of C5a in CBE-induced GCase deficiency. WT mice were injected i.p. with PBS (n=10, black column) or CBE (100 mg/kg/day; n=10, white colunm). Sera from both groups were assessed for IgG1, IgG2a, IgG2b, and IgG3 antibodies to GC (FIG. 14A). Several tissues, (e.g., liver, spleen, and lung) and sera of indicated mice strains were investigated for C3b deposition (FIG. 14B) and circulatory level of C5a concentrations (FIG. 14C). Values are the means±s.d.; group comparisons were done by ANOVA (FIG. 14A) or t-test (FIG. 14C) with the a priori comparison being WT to C5aR1$^{-/-}$ mice. For each experiment, two conditions were evaluated (PBS and CBE), thus the Bonferroni corrected significance threshold is 0.025. *** p<0.001.
Figure 14A:
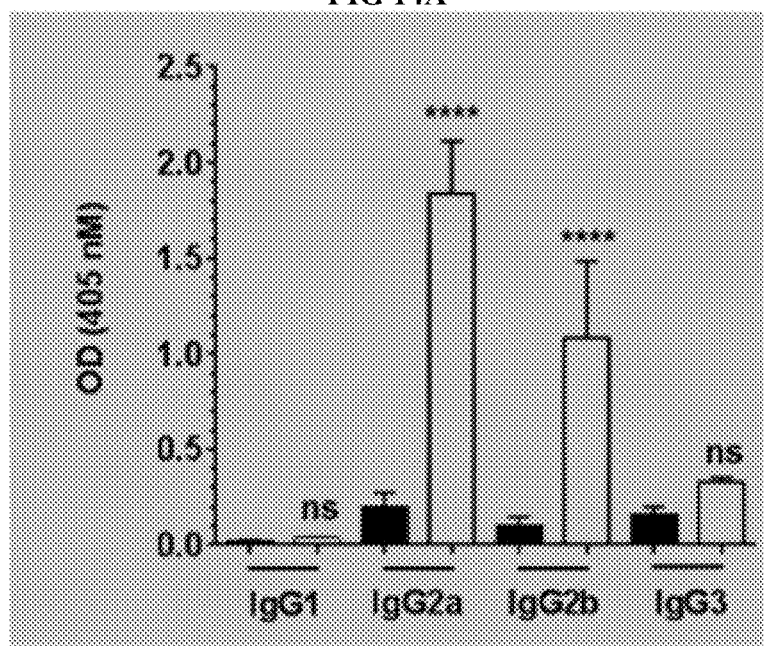
Figure 14B:
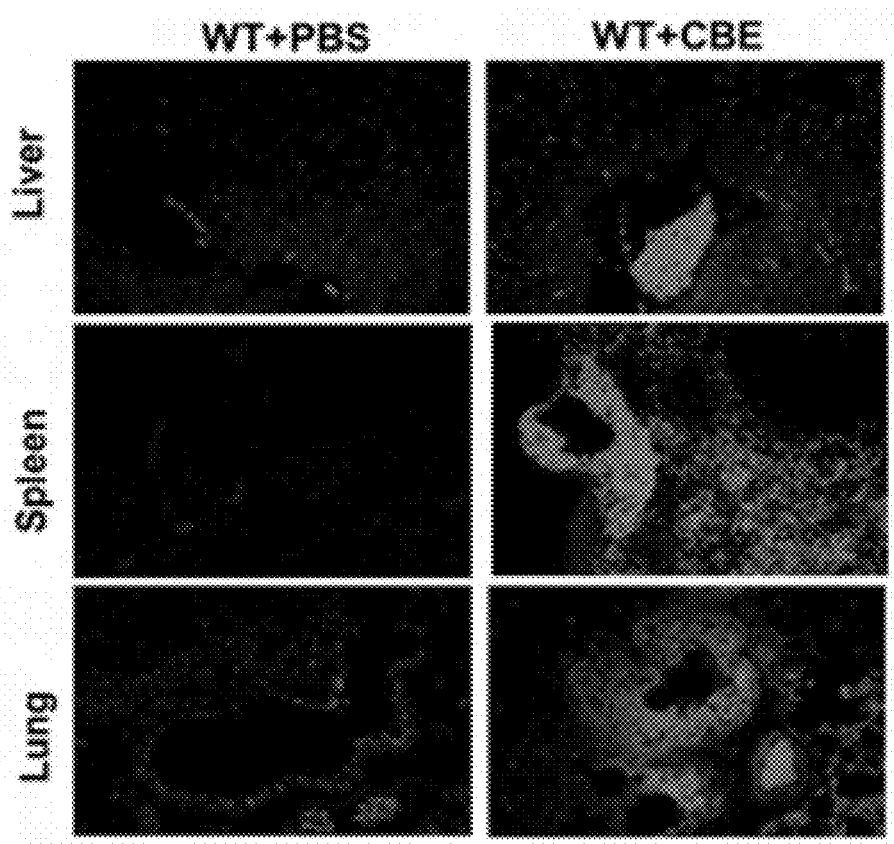
Figure 14C:
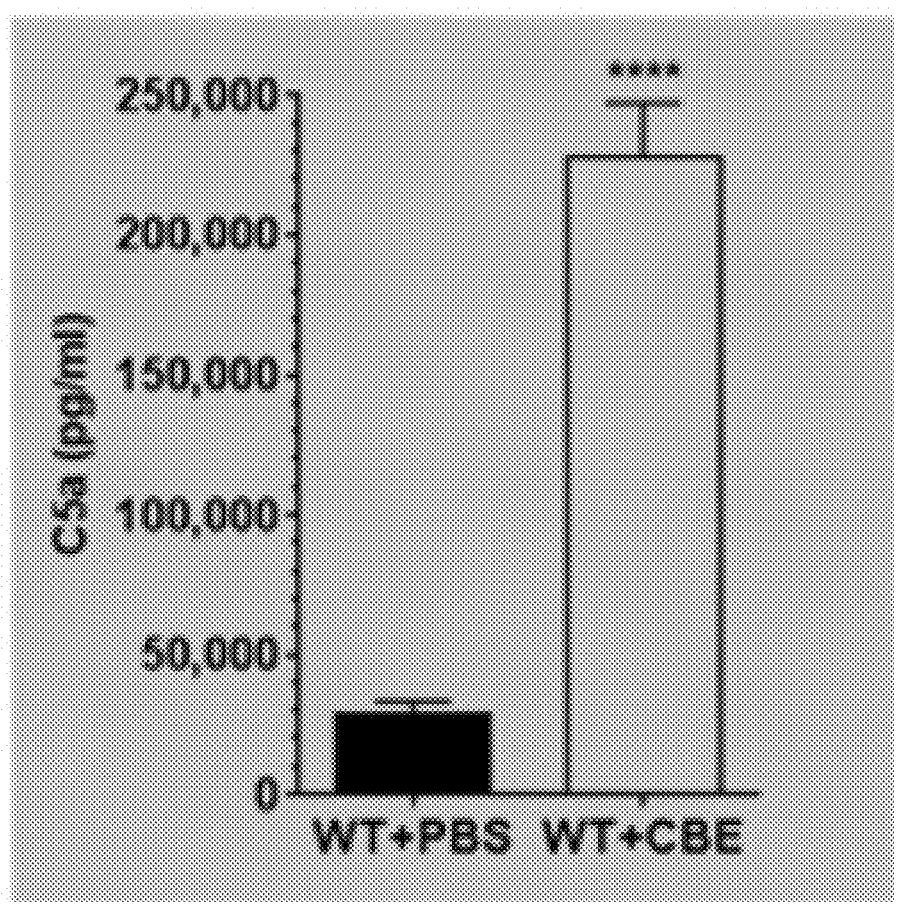
Figure 15A:
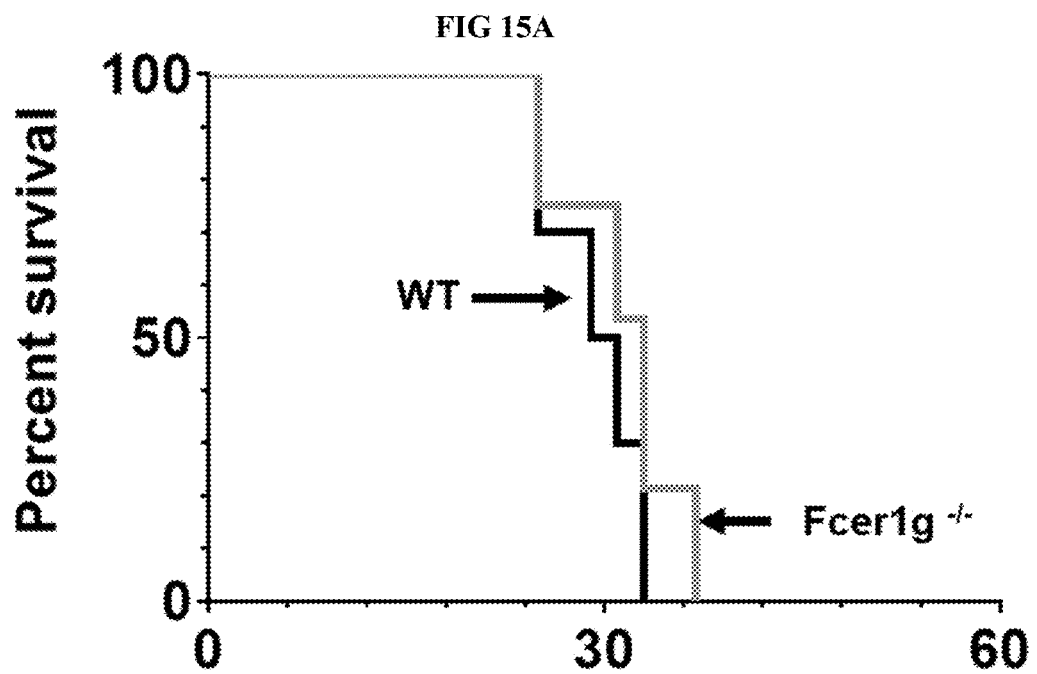
FIG. 15A-15B. Genetic deficiency of activating or inhibitory FcγRs has no impact on survival after CBE-induced GCase deficiency. WT, Fcer1g$^{-/-}$ and Fcgr2b$^{-/-}$ mice (n=10/ each group) were injected i.p. with CBE (100 mg/kg) or vehicle (PBS) daily for up to 30 days. Survival plots are shown for CBE-treated WT (FIG. 15A and FIG. 15B, dark gray lines), Fce1g$^{-/-}$ (FIG. 15A, light gray line), and Fcgr2b$^{-/-}$ (FIG. 15B, light gray line) mice.
Figure 15B:
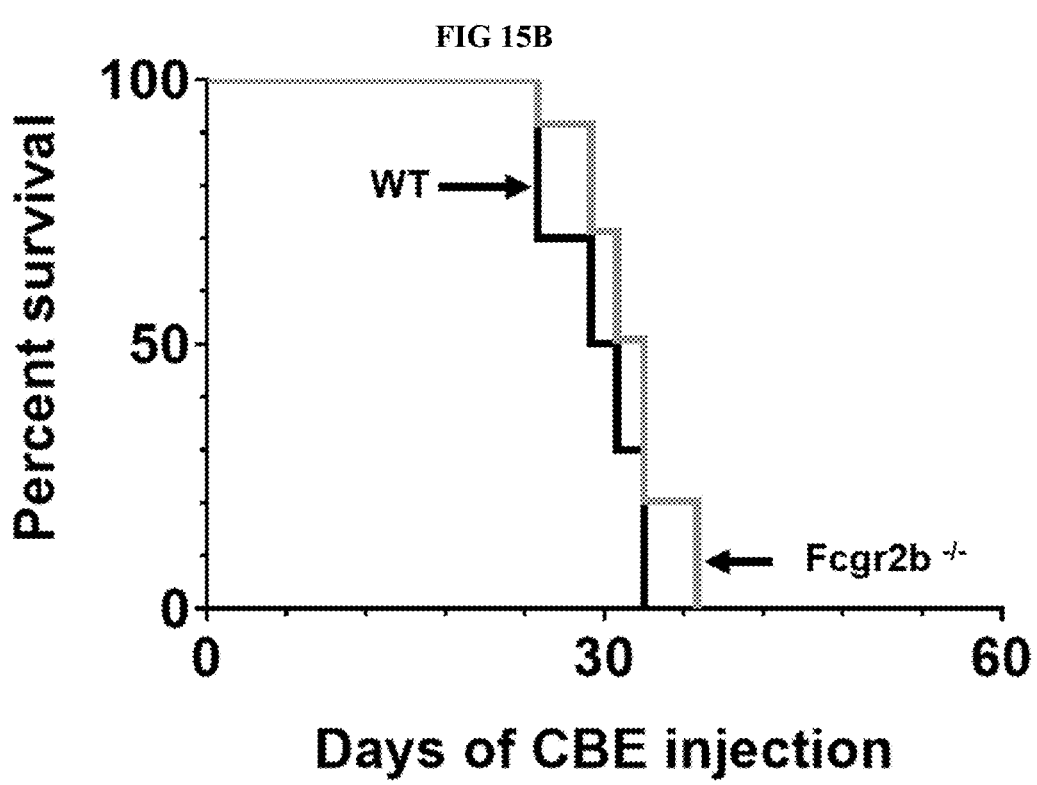

Applicant hypothesized that the strong complement activation was based on the massive GC tissue accumulation resulting in the break of tolerance and subsequent induction of GC-specific IgG auto-antibodies. Indeed, significant levels of GC-specific IgG2a and IgG2b auto antibodies were present only in sera of 9V/null mice. The presence of GC-specific IgG3 antibodies was minor. No GC-specific IgG1 antibodies were detected. (FIG. 4a). Further, the different IgG auto-antibodies showed no cross reactivity toward glucosyl-sphingosine (FIG. 13). To formally assess the presence of complement-activating immune complexes in the serum of 9V/null mice, IgG2a was purified from sera of WT and 9V/null mice as this TgG isotype is a strong activator of complement in mice.[18, 19] The GC fraction bound to this purified IgG2a of WT and 9V/null mice was quantified by ESI-LC-MS/MS. Applicant found that significant amounts of GC were bound to IgG2a from 9V/null, but not from WT (FIG. 6B). To further test the induction of GC-specific IgG auto-antibodies, WT mice were treated for 30 days with CBE. Serum levels of GC-specific IgG1, IgG2a IgG2b, and IgG3 auto-antibodies were assessed as was tissue expression of C3 and serum levels of C5a. Only the CBE-treated group showed significantly elevated serum levels of IgG2a and IgG2b antibodies to GC (FIG. 14A), liver, spleen, and lung deposition of C3b (FIG. 14B), and elevated serum levels of C5a (FIG. 14C). These data implicate a mechanism of excessive release GC from tissues that drives the formation of IgG autoantibodies leading to activation of the complement system.

Figure 6C:
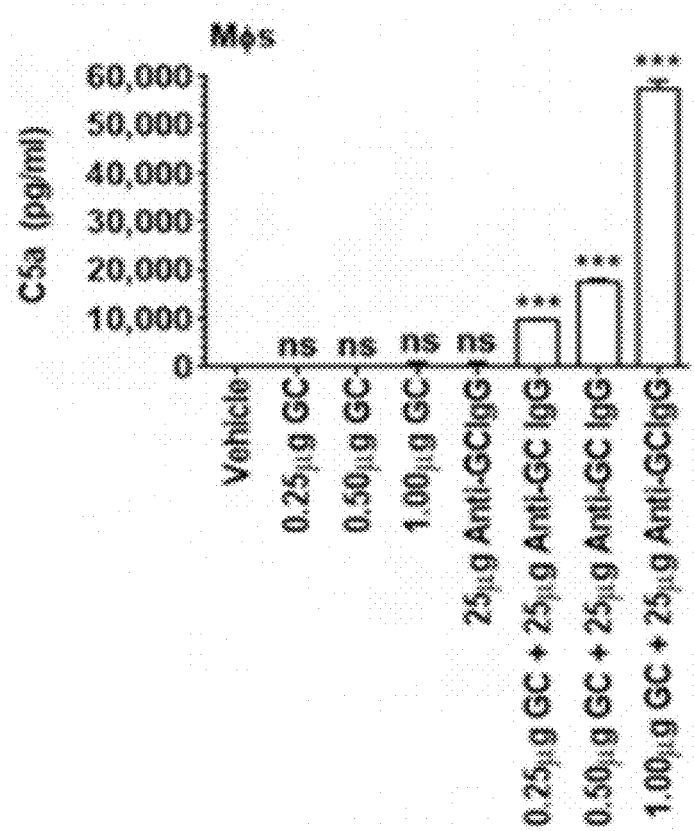
Figure 6D:
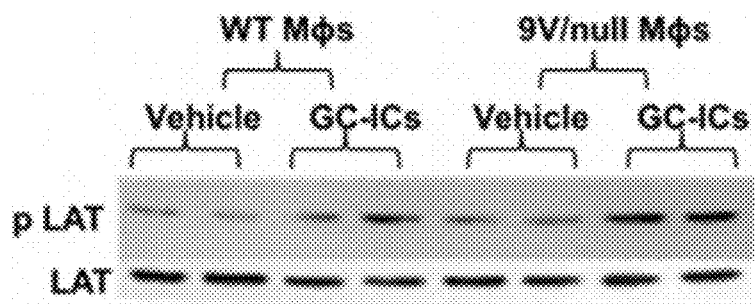
Figure 6E:
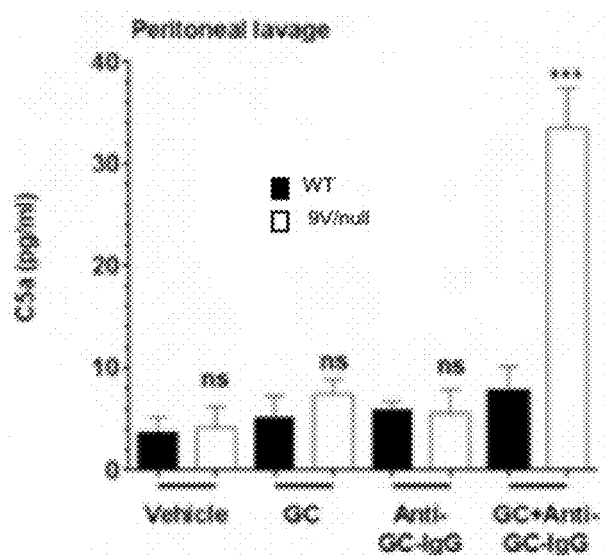
Figure 6F:
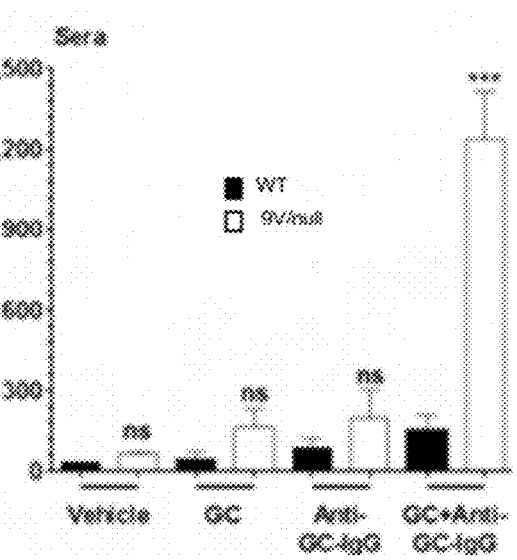

IgG-immune complexes (IgG-ICs) can activate phagocytes through IgG Fc receptors (FcγR) and drive tissue inflammation.[20] The role of FcγRs for IgG-IC-mediated inflammation was evaluated by CBE administration to WT mice and those lacking activating FcγRs (Fcγr1g$^{-/-}$) or the inhibitory FcγRIIB (Fcgr2b$^{-/-}$). Like CBE-injected WT mice, CBE-treated Fcer1g$^{-/-}$ and Fcgr2b$^{-/-}$ mice died by 29-36 days of daily injections (FIG. 14A, 14B). IgG-ICs can promote local C5 production and C5a generation from macrophages through an Fc©R-dependent mechanism that involves LAT phosphorylation 21. Thus, the stimulatory effects on MΦs from 9V/null mice were evaluated in the presence or absence of GC, anti-GC IgG or GC-ICs. A strong and dose-dependent C5a production was found only with GC-IC treatment (FIG. 6C). Also, GC-ICs mediated LAT phosphorylation in MΦs from WT and 9V/null mice. Importantly, the LAT phosphorylation was much stronger in 9V/null MΦs (FIG. 6D). Finally, WT and 9V/null mice were injected i.p. with vehicle, GC, anti-GC or GC-ICs. Within two hours after i.p. injection of GC-ICs, significant peritoneal C5a production was observed as was C5a presence in serum of 9V/null mice (FIG. 6E, 6F). Together, these findings suggest that FcγR-driven cell activation can drive local C5a production from MΦs, but plays no significant role for the inflammatory response in GCase deficiency.

Figure 6G:
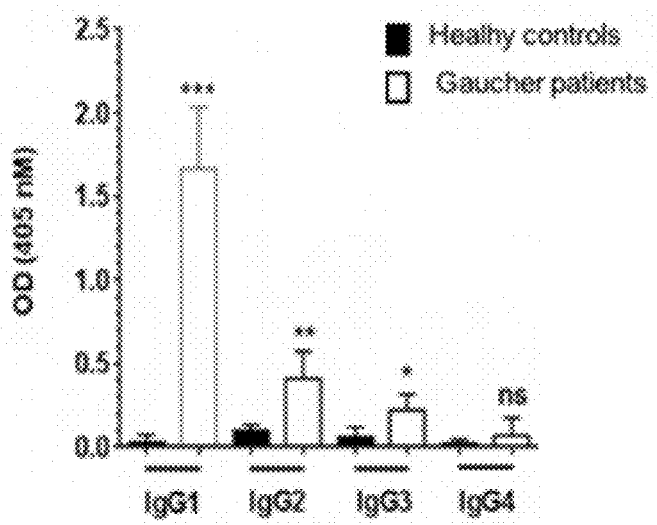
Figure 6H:
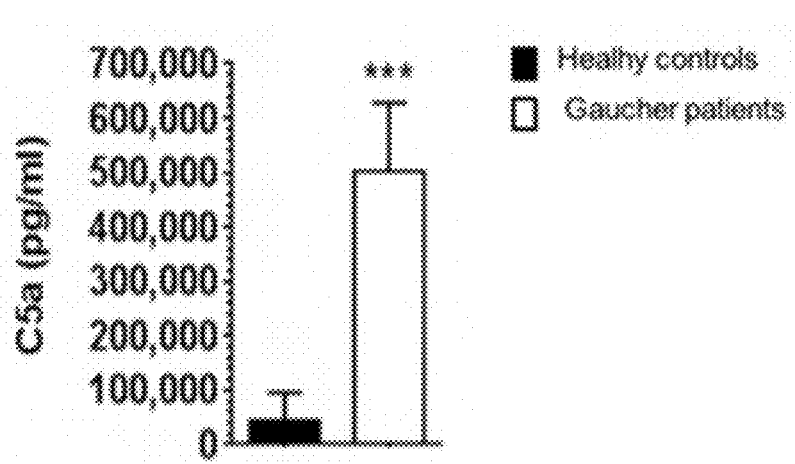
Figure 6I:
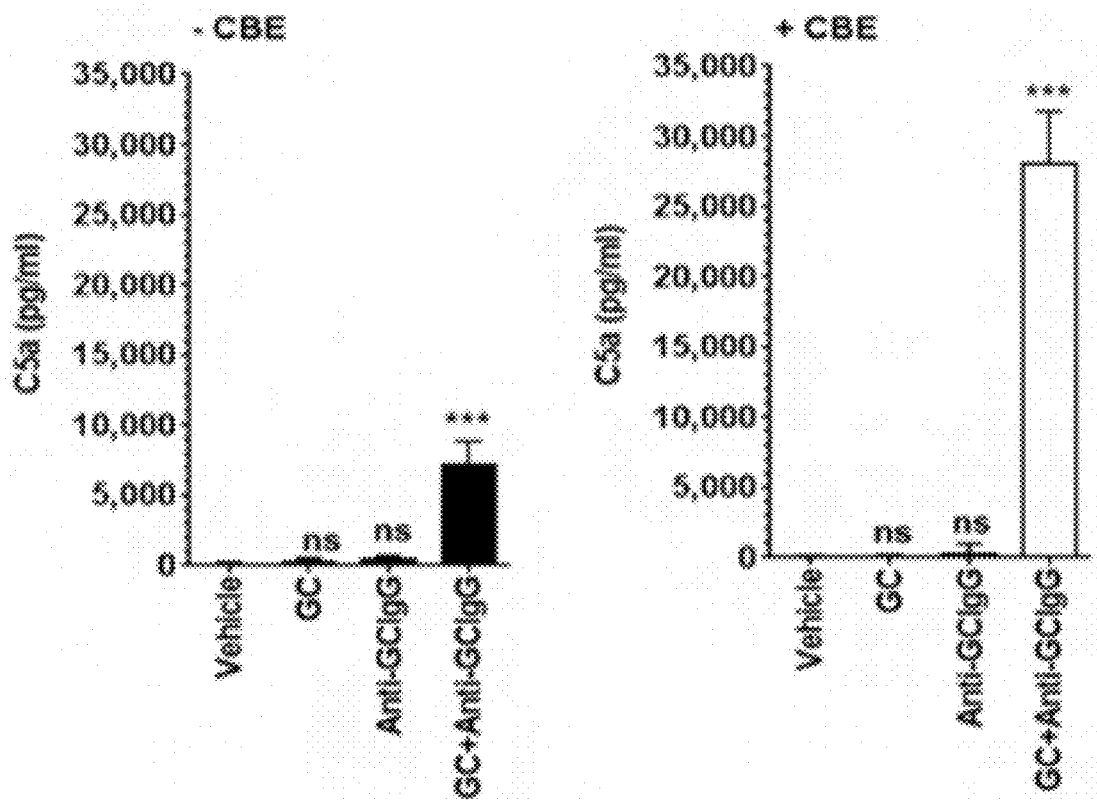
Figure 6J:
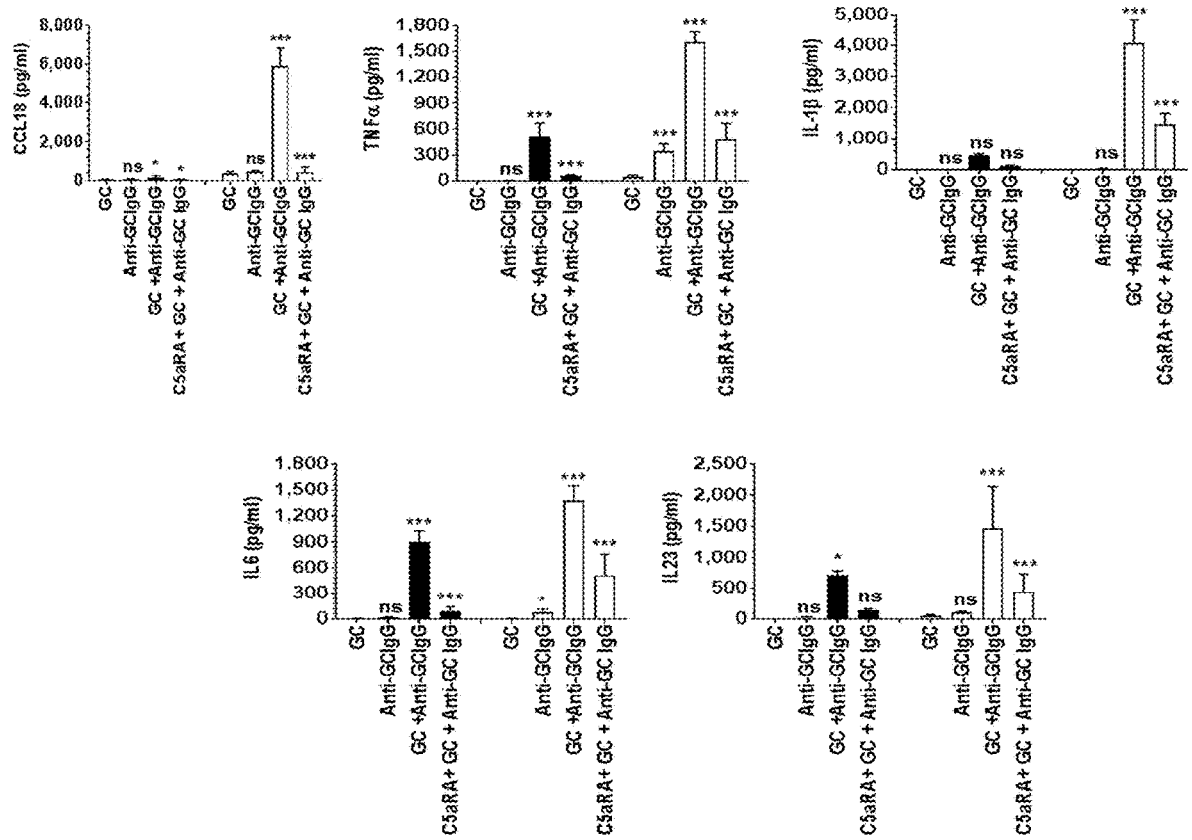

To assess the translational relevance of these findings, Applicant determined the serum levels of GC-specific IgG1, TgG2, IgG3, and IgG4 antibodies and C5a in normal healthy volunteers and in untreated patients with Gaucher disease. High serum levels of GC-specific IgG1, IgG2 and IgG3 (FIG. 6G) and markedly elevated C5a concentrations were found in the sera from these Gaucher disease patients (FIG. 6H). Further, the impact of GC-ICs on complement activation and the generation of C5a was evaluated using the human MΦ-like cell line U937. These cells were treated with CBE or vehicle (PBS) in the presence or absence of GC, anti-GC IgG or GC-ICs. High level production of C5a was evident in GC-IC-stimulated and CBE-treated cells (FIG. 6I). Finally, C5aR1 was inhibited with C5aRA and the impact was evaluated on GC-IC-induced production of CCL18, and other pro-inflammatory cytokines, (e.g., TNFα, IL1β, IL6, and IL23) which are all high in Gaucher disease patients. CBE treatment induced strong production of these inflammatory mediators in U937 cells in response to GC-IC stimulation. This was abolished by C5aRA (FIG. 6J). These data support C5aR1 activation playing an important role in GC-IC driven propagation of immune inflammation.

Figure 16:
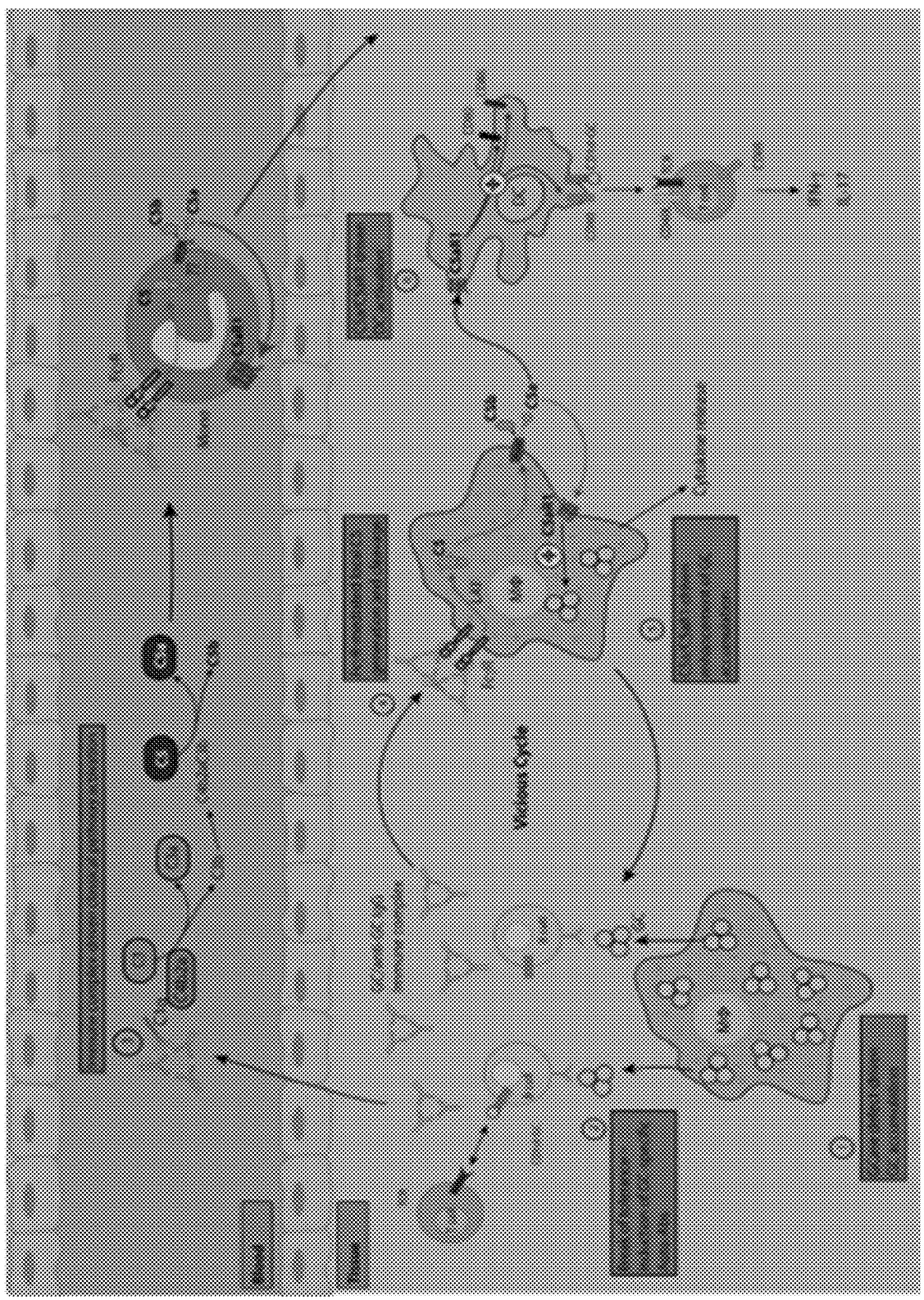
FIG. 16. Model detailing the role of the C5a/C5aR1 axis in Gaucher disease. (1) Mutations in GBA1, encoding defective GCase, result in the accumulation of glucosylceramide (GC) preferentially in visceral macrophages. (2) Continuous release of GC from macrophages, uptake and processing by B cells and Cd1d-restricted activation of T cells results in the differentiation of B cells into plasma cells and the production of GC-specific IgG2a/b auto-antibodies (Abs). (3) Such IgG auto-Abs form immune complexes with GC that activate the classical pathway of complement, eventually leading to systemic C5 cleavage and C5a generation. (4) GC-anti-GC IgG immune complexes bind to activating FcγRs present on macrophages and induce local C5 production by a linker for activation of T cell (LAT)-dependent mechanism. Further, FcγR activated macrophages cleave C5 into C5a by a cell-specific protease. This local C5 production and C5a may also occur in circulating, inflammatory monocytes, which express IgG2c/b-binding FcγRIV (Biburger, M. et al. Monocyte subsets responsible for immunoglobulin G-dependent effector functions in vivo. Immunity 35, 932-944 (2011). (5) The binding of systemically or locally-generated C5a to C5aR1 enhances the accumulation of GC within macrophages driving a vicious cycle that fuels the autoimmune response against GC. Importantly, the abrogation of this vicious cycle is sufficient to massively, but not completely, reduces cellular GC accumulation and protect from death in genetic and pharmacologically-induced Gaucher disease models. (6) Activation of the C5a/C5aR1 axis in dendritic cells upregulates costimulatory molecules (CD80/CD86/CD40) and drives the activation of T cells (CD40L/CD69) eventually resulting in the induction of a pro-inflammatory environment (IFN-γ and IL-17A/F) that promotes the tissue destruction in Gaucher disease.

In sum, Applicant has identified a novel role for complement as a co-factor for or driver of pro-inflammation in Gaucher disease. Based on these findings, a dual role model for the C5a/C5aR1 axis in Gaucher disease is proposed. First, it serves as a critical pathway that promotes the excessive cellular accumulation and release of GC as the basis for the formation of GC-specific IgG-ICs. Such ICs then drive massive complement activation leading to excessive systemic and tissue C5a generation. Secondly, this excess C5a activates APCs and drives Th1/Th17 cell differentiation resulting in undesired production of pro-inflammatory cytokines and chemokines eventually causing increased tissue recruitment of activated immune cells that lead to and/or propagate the molecular mechanisms of tissue damage and resultant Gaucher disease manifestations (FIG. 16). Analogously, IgG ICs toward substrates in other LSDs remains to be explored as a basis of their pro-inflammatory states and disease processes.

REFERENCES

1. Weinreb, N. J., Charrow, J., Andersson, H. C., Kaplan, P., Kolodny, E. H., Mistry, P., Pastores, G., Rosenbloom, B. E., Scott, C. R., Wappner, R. S., and Zimran, A. (2002) Effectiveness of enzyme replacement therapy in 1028 patients with type 1 Gaucher disease after 2 to 5 years of treatment: a report from the Gaucher Registry. *The American journal of medicine* 113, 112-119
2. Britain, B. M. A. a. R. P. S. o. G. (2013) British National Formulary BNF 65 Vol., BMJ Group and RPS Publishing, London
3. Pandey, M. K., and Grabowski, G. A. (2013) Immunological cells and functions in Gaucher disease. *Crit Rev Oncog* 18, 197-220
4. (9 in updated manuscript) Xu, Y. H., Quinn, B., Witte, D., and Grabowski, G. A. (2003) Viable mouse models of acid betaglucosidase deficiency: the defect in Gaucher disease. *Am J Pathol* 163, 2093-2101
5. (1 in updated manuscript) Grabowski, G. A., Petsko, G. A., and Kolodny, E. H. (2010) Gaucher Disease. In *The Online Metabolic and Molecular Bases of Inherited disease* (Valle, D., Beaudet, A. L., Vogelstein, B., Kinzler, K. W., Antonarakis, S. E., and Ballabio, A., eds), New York: Mc Graw Hill
6. (25 in revised manuscript) Pandey, M. K., Rani, R., Zhang, W., Setchell, K., and Grabowski, G. A. (2012) Immunological cell type characterization and Th1-Th17 cytokine production in a mouse model of Gaucher disease. *Mol Genet Metab* 106, 310-322
7. Pandey, M. K., and Grabowski, G. A. (2013) Cytology of Gaucher disease. In *Advances in Gaucher Disease: Basic and Clinical Perspectives* pp. 78-93, Future Medicine Ltd
8. (2 in updated manuscript) Pandey, M. K., Jabre, N. A., Xu, Y. H., Zhang, W., Setchell, K. D., and Grabowski, G. A. (2014) Gaucher disease: Chemotactic factors and immunological cell invasion in a mouse model. *Mol Genet Metab* 111, 163-171
9. Kanfer, J. N., Legler, G., Sullivan, J., Raghavan, S. S., and Mumford, R. A. (1975) The Gaucher mouse. Biochem Biophys Res Commun 67, 85-90
10. Kaloterakis, A., Filiotou, A., Koskinas, J., Raptis, I., Zouboulis, C., Michelakakis, H., and Hadziyannis, S. (1999) Systemic AL amyloidosis in Gaucher disease. A case report and review of the literature. *J Intern Med* 246, 587-590
11. Marie, J. P., Tulliez, M., Tricottet-Paczinski, V., Reynes, M., and Diebold, J. (1982) Gaucher's disease with monoclonal gammopathy. Significance of splenic plasmacytosis. *Scand J Haematol* 28, 54-58
12. Marti, G. E., Ryan, E. T., Papadopoulos, N. M., Filling-Katz, M., Barton, N., Fleischer, T. A., Rick, M., and Gralnick, H. R. (1988) Polyclonal B-cell lymphocytosis and hypergammaglobulinemia in patients with Gaucher disease. *Am J Hematol* 29, 189-194

13. Shoenfeld, Y., Gallant, L. A., Shaklai, M., Livni, E., Djaldetti, M., and Pinkhas, J. (1982) Gaucher's disease: a disease with chronic stimulation of the immune system. *Arch Pathol Lab Med* 106, 388-391
14. Airo, R., Gabusi, G., and Guindani, M. (1993) Gaucher's disease associated with monoclonal gammapathy of undetermined significance: a case report. *Haenatologica* 78, 129-131
15. Arikan-Ayyildiz, Z., Yuce, A., Uslu-Kizilkan, N., Demir, H., and Gurakan, F. (2011) Immunoglobulin abnormalities and effects of enzyme replacement therapy in children with Gaucher disease. *Pediatr Blood Cancer* 56, 664-666
16. Wine, E., Yaniv, I., and Cohen, I. J. (2007) Hyperimmunoglobulinemia in pediatric-onset type 1 Gaucher disease and effects of enzyme replacement therapy. *J Pediatr Hematol Oncol* 29, 451-457
17. Brautbar, A., Elstein, D., Pines, G., Abrahamov, A., and Zimran, A. (2004) Effect of enzyme replacement therapy on gammopathies in Gaucher disease. *Blood Cells Mol Dis* 32, 214-217
18. Pratt, P. W., Kochwa, S., and Estren, S. (1968) Immunoglobulin abnormalities in Gaucher's disease. Report of 16 cases. *Blood* 31, 633-640
19. de Fost, M., Out, T. A., de Wilde, F. A., Tjin, E. P., Pals, S. T., van Oers, M. H., Boot, R. G., Aerts, J. F., Maas, M., Vom Dahl, S., and Hollak, C. E. (2008) Immunoglobulin and free light chain abnormalities in Gaucher disease type I: data from an adult cohort of 63 patients and review of the literature. *Ann Hematol* 87, 439-449
20. Rodic, P., Pavlovic, S., Kostic, T., Suvajdzic Vukovic, N., Djordjevic, M., Sumarac, Z., Dajak, M., Bonaci Nikolic, B., and Janic, D. (2013) Gammopathy and B lymphocyte clonality in patients with Gaucher type I disease. *Blood Cells Mol Dis* 50, 222-225
21. Vairo, F., Alegra, T., Dornelles, A., Mittelstadt, S., Netto, C. B., and Schwartz, L V. (2012) Hyperimmunoglobulinemia in pediatric Gaucher patients in Southern Brazil. *Pediatr Blood Cancer* 59, 339
22. Arikan-Ayyildiz, Z., Yuce, A., Uslu-Kizilkan, N., Demir, H., and Gurakan, F. (2012) Hyperimmunoglobulinemia in pediatric patients with Gaucher disease in Southern Brazil. *Pediatr Blood Cancer* 59, 340
23. Shoenfeld, Y., Beresovski, A., Zharhary, D., Tomer, Y., Swissa, M., Sela, E., Zimran, A., Zevin, S., Gilburd, B., and Blank, M. (1995) Natural autoantibodies in sera of patients with Gaucher's disease. J Clin Immunol 15, 363-372
24. McAlarney, T., Pastores, G. M., Hays, A. P., and Latov, N. (1995) Antisulfatide antibody and neuropathy in a patient with Gaucher's disease. Neurology 45, 1622-1623
25. Brisca, G., Di Rocco, M., Picco, P., Damasio, M. B., and Martini, A. (2011) Coxarthritis as the presenting symptom of Gaucher disease type 1. Arthritis 2011, 361279.
26. (20 in updated manuscript) Nimmerjahn, F. & Ravetch, J. V. Fcgamma receptors as regulators of immune responses. *Nat Rev Immunol* 8, 34-47, doi:10.1038/nri2206 (2008).
27. Williams, J. W., Tjota, M. Y., and Sperling, A. I. (2012) The contribution of allergen-specific IgG to the development of th2-mediated airway inflammation. Journal of allergy 2012, 236075
28. (19 in updated manuscript) Karsten, C. M., and Kohl, J. (2012) The immunoglobulin, IgG Fc receptor and complement triangle in autoimmune diseases. Immunobiology 217, 1067-1079
29. Nimmerjahn, F., Bruhns, P., Horiuchi, K., and Ravetch, J. V. (2005) FcgammaRIV: a novel FcR with distinct IgG subclass specificity. Immunity 23, 41-51
30. Nimmerjahn, F., and Ravetch, J. V. (2006) Fcgamma receptors: old friends and new family members. Immunity 24, 19-28
31. Seino, J., Eveleigh, P., Warnaar, S., van Haarlem, L. J., van Es, L. A., and Daha, M. R. (1993) Activation of human complement by mouse and mouse/human chimeric monoclonal antibodies. Clinical and experimental immunology 94, 291-296
32. (21 in updated manuscript) Syed, S. N. et al. Both FcgammaRIV and FcgammaRIII are essential receptors mediating type TT and type III autoimmune responses via FcRgamma-LAT-dependent generation of C5a. *Eur J Immunol* 39, 3343-3356, doi:10.1002/eji.200939884 (2009).
33. (18 in updated manuscript) Pandey, M. K. (2013) Molecular basis for downregulation of C5a-mediated inflammation by IgG1 immune complexes in allergy and asthma. Curr Allergy Asthma Rep 13, 596-606
34. Skokowa, J., Ali, S. R., Felda, 0., Kumar, V., Konrad, S., Shushakova, N., Schmidt, R. E., Piekorz, R. P., Nurnberg, B., Spicher, K., Birnbaumer, L., Zwirner, J., Claassens, J. W., Verbeek, J. S., van Rooijen, N., Kohl, J., and Gessner, J. E. (2005) Macrophages induce the inflammatory response in the pulmonary Arthus reaction through G alpha i2 activation that controls C5aR and Fc receptor cooperation. J Immunol 174, 3041-3050
35. Kumar, V., Ali, S. R., Konrad, S., Zwirner, J., Verbeek, J. S., Schmidt, R. E., and Gessner, J. E. (2006) Cell-derived anaphylatoxins as key mediators of antibody-dependent type 11 autoimmunity in mice. The Journal of clinical investigation 116, 512-520
36. Lukacs, N. W., Glovsky, M. M., and Ward, P. A. (2001) Complement-dependent immune complex induced bronchial inflammation and hyperreactivity. Am J Physiol Lung Cell Mol Physiol 280, L512-518
37. Ghazizadeh, S., Bolen, J. B., and Fleit, H. B. (1994) Physical and functional association of Src-related protein tyrosine kinases with Fc gamma RII in monocytic THP-1 cells. The Journal of biological chemistry 269, 8878-8884
38. Wang, A. V., Scholl, P. R., and Geha, R. S. (1994) Physical and functional association of the high affinity immunoglobulin G receptor (Fc gamma RI) with the kinases Hck and Lyn. J Exp Med 180, 1165-1170
20. Rodic, P., Pavlovic, S., Kostic, T., Suvajdzic Vukovic, N., Djordjevic, M., Sumarac, Z., Dajak, M., Bonaci Nikolic, B., and Janic, D. (2013) Gammopathy and B lymphocyte clonality in patients with Gaucher type I disease. *Blood Cells Mol Dis* 50, 222-225
21. Vairo, F., Alegra, T., Dornelles, A., Mittelstadt, S., Netto, C. B., and Schwartz, I. V. (2012) Hyperimmunoglobulinemia in pediatric Gaucher patients in Southern Brazil. *Pediatr Blood Cancer* 59, 339
22. Arikan-Ayyildiz, Z., Yuce, A., Uslu-Kizilkan, N., Demir, H., and Gurakan, F. (2012) Hyperimmunoglobulinemia in pediatric patients with Gaucher disease in Southern Brazil. *Pediatr Blood Cancer* 59, 340
23. Shoenfeld, Y., Beresovski, A., Zharhary, D., Tomer, Y., Swissa, M., Sela, E., Zimran, A., Zevin, S., Gilburd, B., and Blank, M. (1995) Natural autoantibodies in sera of patients with Gaucher's disease. *J Clin Immunol* 15, 363-372
24. McAlarney, T., Pastores, G. M., Hays, A. P., and Latov, N. (1995) Antisulfatide antibody and neuropathy in a patient with Gaucher's disease. *Neurology* 45, 1622-1623

25. Brisca, G., Di Rocco, M., Picco, P., Damasio, M. B., and Martini, A. (2011) Coxarthritis as the presenting symptom of Gaucher disease type 1. Arthritis 2011, 361279
26. Nimmerjahn, F., and Ravetch, J. V. (2008) Fcgamma receptors as regulators of immune responses. Nature reviews. Immunology 8, 34-47
27. Williams, J. W., Tjota, M. Y., and Sperling, A. I. (2012) The contribution of allergen-specific IgG to the development of th2-mediated airway inflammation. *Journal of allergy* 2012, 236075
28. Karsten, C. M., and Kohl, J. (2012) The immunoglobulin, IgG Fc receptor and complement triangle in autoimmune diseases. *Immunobiology* 217, 1067-1079
29. Nimmerjahn, F., Bruhns, P., Horiuchi, K., and Ravetch, J. V. (2005) FcgammaRIV: a novel FcR with distinct IgG subclass specificity. *Immunity* 23, 41-51
30. Nimmerjahn, F., and Ravetch, J. V. (2006) Fcgamma receptors: old friends and new family members. *Immunity* 24, 19-28
31. Seino, J., Eveleigh, P., Warnaar, S., van Haarlem, L. J., van Es, L. A., and Daha, M. R. (1993) Activation of human complement by mouse and mouse/human chimeric monoclonal antibodies. *Clinical and experimental immunology* 94, 291-296
32. Syed, S. N., Konrad, S., Wiege, K., Nieswandt, B., Nimmerjahn, F., Schmidt, R. E., and Gessner, J. E. (2009) Both FcgammaRIV and FcgammaRIII are essential receptors mediating type II and type III autoimmune responses via FcRgamma-LAT-dependent generation of C5a. *Eur J Immunol* 39, 3343-3356
33. Pandey, M. K. (2013) Molecular basis for downregulation of C5a-mediated inflammation by IgG1 immune complexes in allergy and asthma. *Curr Allergy Asthma Rep* 13, 596-606
34. Skokowa, J., Ali, S. R., Felda, O., Kumar, V., Konrad, S., Shushakova, N., Schmidt, R. E., Piekorz, R. P., Nurnberg, B., Spicher, K., Birnbaumer, L., Zwirner, J., Claassens, J. W., Verbeek, J. S., van Rooijen, N., Kohl, J., and Gessner, J. E. (2005) Macrophages induce the inflammatory response in the pulmonary Arthus reaction through G alpha i2 activation that controls C5aR and Fc receptor cooperation. *J Immunol* 174, 3041-3050
35. Kumar, V., Ali, S. R., Konrad, S., Zwirner, J., Verbeek, J. S., Schmidt, R. E., and Gessner, J. E. (2006) Cell-derived anaphylatoxins as key mediators of antibody-dependent type II autoimmunity in mice. *The Journal of clinical investigation* 116, 512-520
36. Lukacs, N. W., Glovsky, M. M., and Ward, P. A. (2001) Complement-dependent immune complexinduced bronchial inflammation and hyperreactivity. *Am J Physiol Lung Cell Mol Physiol* 280, L512-518
37. Ghazizadeh, S., Bolen, J. B., and Fleit, H. B. (1994) Physical and functional association of Src-related protein tyrosine kinases with Fc gamma RII in monocytic THP-1 cells. *The Journal of biological chemistry* 269, 8878-8884
38. Wang, A. V., Scholl, P. R., and Geha, R. S. (1994) Physical and functional association of the high affinity immunoglobulin G receptor (Fc gamma RI) with the kinases Hck and Lyn. *J Exp Med* 180, 1165-1170
39. Matsubara, S., Koya, T., Takeda, K., Joetham, A., Miyahara, N., Pine, P., Masuda, E. S., Swasey, C. H., and Gelfand, E. W. (2006) Syk activation in dendritic cells is essential for airway hyperresponsiveness and inflammation. American journal of respiratory cell and molecular biology 34, 426-433
40. Nakashima, K., Kokubo, T., Shichijo, M., Li, Y. F., Yura, T., and Yamamoto, N. (2004) A novel Syk kinase-selective inhibitor blocks antigen presentation of immune complexes in dendritic cells. European journal of pharmacology 505, 223-228
41. Rafiq, K., Bergtold, A., and Clynes, R. (2002) Immune complex-mediated antigen presentation induces tumor immunity. The Journal of clinical investigation 110, 71-79
42. Braun, A., Gessner, J. E., Varga-Szabo, D., Syed, S. N., Konrad, S., Stegner, D., Vogtle, T., Schmidt, R. E., and Nieswandt, B. (2009) STIM1 is essential for Fcgamma receptor activation and autoimmune inflammation. Blood 113, 1097-1104
43. Tridandapani, S., Lyden, T. W., Smith, J. L., Carter, J. E., Coggeshall, K. M., and Anderson, C. L. (2000) The adapter protein LAT enhances fcgamna receptor-mediated signal transduction in myeloid cells. The Journal of biological chemistry 275, 20480-20487
44. Zhang, W., Sommers, C. L., Burshtyn, D. N., Stebbins, C. C., DeJarnette, J. B., Trible, R. P., Grinberg, A., Tsay, H. C., Jacobs, H. M., Kessler, C. M., Long, E. O., Love, P. E., and Samelson, L. E. (1999) Essential role of LAT in T cell development. Immunity 10, 323-332
45. Saitoh, S., Arudchandran, R., Manetz, T. S., Zhang, W., Sommers, C. L., Love, P. E., Rivera, J., and Samelson, L. E. (2000) LAT is essential for Fc(epsilon)RI-mediated mast cell activation. Immunity 12, 525-535
46. Liszewski, M. K., Kolev, M., Le Friec, G., Leung, M., Bertram, P. G., Fara, A. F., Subias, M., Pickering, M. C., Drouet, C., Meri, S., Arstila, T. P., Pekkarinen, P. T., Ma, M., Cope, A., Reinheckel, T., Rodriguez de Cordoba, S., Afzali, B., Atkinson, J. P., and Kemper, C. (2013) Intracellular complement activation sustains T cell homeostasis and mediates effector differentiation. Immunity 39, 1143-1157
47. Liu, J., Halene, S., Yang, M., Iqbal, J., Yang, R., Mehal, W. Z., Chuang, W. L., Jain, D., Yuen, T., Sun, L., Zaidi, M., and Mistry, P. K. (2012) Gaucher disease gene GBA functions in immune regulation. Proc Nall Acad Sci USA 109, 10018-10023
48. Xu, Y. H., Jia, L., Quinn, B., Zamzow, M., Stringer, K., Aronow, B., Sun, Y., Zhang, W., Setchell, K. D., and Grabowski, G. A. (2011) Global gene expression profile progression in Gaucher disease mouse models. BMC Genonics 12, 20
49. Hong, Y. B., Kim, E Y., and Jung, S. C. (2006) Upregulation of proinflammatory cytokines in the fetal brain of the Gaucher mouse. J Korean Med Sci 21, 733-738
50. Boven, L. A., van Meurs, M., Boot, R. G., Mehta, A., Boon, L., Aerts, J. M., and Laman, J. D. (2004) Gaucher cells demonstrate a distinct macrophage phenotype and resemble alternatively activated macrophages. Am J Clin Pathol 122, 359-369
51. Arikan-Ayyildiz, Z., Yuce, A., Uslu-Kizilkan, N., Demir, H., and Gurakan, F. (2010) Immunoglobulin abnormalities and effects of enzyme replacement therapy in children with Gaucher disease. Pediatr Blood Cancer
52. Fujita, T., Matai, K., Kohno, S., and Itsubo, K. (1996) Impact of splenectomy on circulating immunoglobulin levels and the development of postoperative infection following total gastrectomy for gastric cancer. Br J Surg 83, 1776-1778
53. Camou, F., and Viallard, J. F. (2012) Extended remission of B-cell lymphoma with monoclonal gammopathy in a patient with type 1 Gaucher disease treated with enzyme replacement therapy. Blood Cells Mol Dis 48, 51-52

54. Pavlova, E. V., Wang, S. Z., Archer, J., Dekker, N., Aerts, J. M., Karlsson, S., and Cox, T. M. (2013) B cell lymphoma and myeloma in murine Gaucher's disease. *J Pathol* 231, 88-97
55. Balreira, A., Cavallari, M., Sa Miranda, M. C., and Arosa, F. A. (2010) Uncoupling between CD1d upregulation induced by retinoic acid and conduritol-B-epoxide and iNKT cell responsiveness. *Immunobiology* 215, 505-513
56. Mistry, P. K., Liu, J., Yang, M., Nottoli, T., McGrath, J., Jain, D., Zhang, K., Keutzer, J., Chuang, W. L., Mehal, W. Z., Zhao, H., Lin, A., Mane, S., Liu, X., Peng, Y. Z., Li, J. H., Agrawal, M., Zhu, L. L., Blair H. C, Robinson L. J, Iqbal J., Sun L., Zaidi, M. Glucocerebrosidase gene-deficient mouse recapitulates Gaucher disease displaying cellular and molecular dysregulation beyond the macrophage. *PNAS* 2010 Nov. 9; 107(45): 19473-8. doi: 10.1073/pnas.1003308107. Epub 2010 Oct. 20.
39. Matsubara, S., Koya, T., Takeda, K., Joetham, A., Miyahara, N., Pine, P., Masuda, E. S., Swasey, C. H., and Gelfand, E. W. (2006) Syk activation in dendritic cells is essential for airway hyperresponsiveness and inflammation. *American journal of respiratory cell and molecular biology* 34, 426-433
40. Nakashima, K., Kokubo, T., Shichijo, M., Li, Y. F., Yura, T., and Yamamoto, N. (2004) A novel Syk kinase-selective inhibitor blocks antigen presentation of immune complexes in dendritic cells. *European journal of pharmacology* 505, 223-228
41. Rafiq, K., Bergtold, A., and Clynes, R. (2002) Immune complex-mediated antigen presentation induces tumor immunity. *The Journal of clinical investigation* 110, 71-79
42. Braun, A., Gessner, J. E., Varga-Szabo, D., Syed, S. N., Konrad, S., Stegner, D., Vogtle, T., Schmidt, R. E., and Nieswandt, B. (2009) STIM1 is essential for Fcgamma receptor activation and autoimmune inflammation. *Blood* 113, 1097-1104
43. Tridandapani, S., Lyden, T. W., Smith, J. L., Carter, J. E., Coggeshall, K. M., and Anderson, C. L. (2000) The adapter protein LAT enhances fcgamma receptor-mediated signal transduction in myeloid cells. *The Journal of biological chemistry* 275, 20480-20487
44. Zhang, W., Sommers, C. L., Burshtyn, D. N., Stebbins, C. C., DeJarnette, J. B., Trible, R. P., Grinberg, A., Tsay, H. C., Jacobs, H. M., Kessler, C. M., Long, E. O., Love, P. E., and Samelson, L. E. (1999) Essential role of LAT in T cell development. *Immunity* 10, 323-332
45. Saitoh, S., Arudchandran, R., Manetz, T. S., Zhang, W., Sonmiers, C. L., Love, P. E., Rivera, J., and Samelson, L. E. (2000) LAT is essential for Fc(epsilon)RI-mediated mast cell activation. *Immunity* 12, 525-535
46. Liszewski, M. K., Kolev, M., Le Friec, G., Leung, M., Bertram, P. G., Fara, A. F., Subias, M., Pickering, M. C., Drouet, C., Meri, S., Arstila, T. P., Pekkarinen, P. T., Ma, M., Cope, A., Reinheckel, T., Rodriguez de Cordoba, S., Afzali, B., Atkinson, J. P., and Kemper, C. (2013) Intracellular complement activation sustains T cell homeostasis and mediates effector differentiation. *Immunity* 39, 1143-1157
47. Liu, J., Halene, S., Yang, M., Iqbal, J., Yang, R., Mehal, W. Z., Chuang, W. L., Jain, D., Yuen, T., Sun, L., Zaidi, M., and Mistry, P. K. (2012) Gaucher disease gene GBA functions in immune regulation. *Proc Nat Acad Sci USA* 109, 10018-10023
48. Xu, Y. H., Jia, L., Quinn, B., Zamzow, M., Stringer, K., Aronow, B., Sun, Y., Zhang, W., Setchell, K. D., and Grabowski, G. A. (2011) Global gene expression profile progression in Gaucher disease mouse models. *BMC Genomics* 12, 20
49. Hong, Y. B., Kim, E. Y., and Jung, S. C. (2006) Upregulation of proinflammatory cytokines in the fetal brain of the Gaucher mouse. *J Korean Med Sci* 21, 733-738
50. Boven, L. A., van Meurs, M., Boot, R. G., Mehta, A., Boon, L., Aerts, J. M., and Laman, J. D. (2004) Gaucher cells demonstrate a distinct macrophage phenotype and resemble alternatively activated macrophages. *Am J Clin Pathol* 122, 359-369
51. Arikan-Ayyildiz, Z., Yuce, A., Uslu-Kizilkan, N., Demir, H., and Gurakan, F. (2010) Immunoglobulin abnormalities and effects of enzyme replacement therapy in children with Gaucher disease. *Pediatr Blood Cancer*
52. Fujita, T., Matai, K., Kohno, S., and Itsubo, K. (1996) Impact of splenectomy on circulating immunoglobulin levels and the development of postoperative infection following total gastrectomy for gastric cancer. *Br J Surg* 83, 1776-1778
53. Camou, F., and Viallard, J. F. (2012) Extended remission of B-cell lymphoma with monoclonal gammopathy in a patient with type 1 Gaucher disease treated with enzyme replacement therapy. *Blood Cells Mol Dis* 48, 51-52
54. Pavlova, E. V., Wang, S. Z., Archer, J., Dekker, N., Aerts, J. M., Karlsson, S., and Cox, T. M. (2013) B cell lymphoma and myeloma in murine Gaucher's disease. *J Pathol* 231, 88-97
55. Balreira, A., Cavallari, M., Sa Miranda, M. C., and Arosa, F. A. (2010) Uncoupling between CD1d upregulation induced by retinoic acid and conduritol-B-epoxide and iNKT cell responsiveness. *Immunobiology* 215, 505-513
56. Mistry, P. K., Liu, J., Yang, M., Nottoli, T., McGrath, J., Jain, D., Zhang, K., Keutzer, J., Chuang, W. L., Mehal, W. Z., Zhao, H., Lin, A., Mane, S., Liu, X., Peng, Y. Z., Li, J. H., Agrawal, M., Zhu, L. L., Blair, H. C., Robinson, L. J., Iqbal, J., Sun, L., and Zaidi, M. (2010) Glucocerebrosidase gene-deficient mouse recapitulates Gaucher disease displaying cellular and molecular dysregulation beyond the macrophage. *Proc Natl Acad Sci USA* 107, 19473-19478
57. Yan, C., and Gao, H. (2012) New insights for C5a and C5a receptors in sepsis. *Front Immunol* 3, 368
58. Ricklin, D., Hajishengallis, G., Yang, K., and Lambris, J. D. (2010) Complement: a key system for immune surveillance and homeostasis. *Nat Immunol* 11, 785-797
59. Guo, R. F., and Ward, P. A. (2005) Role of C5a in inflammatory responses. *Annual review of immunology* 23, 821-852
60. Zhang, X., and Kohl, J. (2010) A complex role for complement in allergic asthma. *Expert review of clinical immunology* 6, 269-277
61. Kohl, J., Baelder, R., Lewkowich, I. P., Pandey, M. K., Hawlisch, H., Wang, L., Best, J., Herman, N. S., Sproles, A. A., Zwirner, J., Whitsett, J. A., Gerard, C., Sfyroera, G., Lambris, J. D., and Wills-Karp, M. (2006) A regulatory role for the C5a anaphylatoxin in type 2 immunity in asthma. *J Clin Invest* 116, 783-796
62. Koyasu, S. (2003) The role of PI3K in immune cells. *Nature immunology* 4, 313-319
63. Davignon, I., Catalina, M. D., Smith, D., Montgomery, J., Swantek, J., Croy, J., Siegelman, M., and Wilkie, T. M. (2000) Normal hematopoiesis and inflammatory responses despite discrete signaling defects in Galpha15 knockout mice. *Molecular and cellular biology* 20, 797-804
64. Haas, P. J., and van Strijp, J. (2007) Anaphylatoxins: their role in bacterial infection and inflammation. *Immunol Res* 37, 161-175
65. van Lookeren Campagne, M., Wiesmann, C., and Brown, E. J. (2007) Macrophage complement receptors and pathogen clearance. *Cell Microbiol* 9, 2095-2102
66. Karsten, C. M., Pandey, M. K., Figge, J., Kilchenstein, R., Taylor, P. R., Rosas, M., McDonald, J. U., Orr, S. J., Berger, M., Petzold, D., Blanchard, V., Winkler, A., Hess, C., Reid, D. M., Majoul, I. V., Strait, R. T., Harris, N. L., Kohl, G., Wex, E., Ludwig, R., Zillikens, D., Nimmerjahn, F., Finkelman, F. D., Brown, G. D., Ehlers, M., and Kohl, J. (2012) Anti-inflammatory activity of IgG1 mediated by Fc galactosylation and association of FcgammaRllB and dectin-1. *Nat Med* 18, 1401-1406
67. (22 in updated manuscript) Boot, R. G., Verhoek, M., de Fost, M., Hollak, C. E., Maas, M., Bleijlevens, B., van Breemen, M. J., van Meurs, M., Boven, L. A., Laman, J. D., Moran, M. T., Cox, T. M., and Aerts, J. M. (2004) Marked elevation of the chemokine CCL18/PARC in Gaucher disease: a novel surrogate marker for assessing therapeutic intervention. *Blood* 103, 33-39
68. (23 in revised manuscript) Atamas, S. P., Luzina, I. G., Choi, J., Tsymbalyuk, N., Carbonetti, N. H., Singh, I. S., Trojanowska, M., Jimenez, S. A., and White, B. (2003) Pulmonary and activation-regulated chemokine stimulates collagen production in lung fibroblasts. *Am J Respir Cell Mol Biol* 29, 743-749
69. (12 in updated manuscript) Karsten, C. M., Laumonnier, Y., Eurich, B., Ender, F., Broker, K., Roy, S., Czabanska, A., Vollbrandt, T., Figge, J., and Kohl, J. (2015) Monitoring and Cell-Specific Deletion of C5aR1 Using a Novel Floxed GFP-05aR1 Reporter Knock-in Mouse. *J Immunol* 194, 1841-1855
70. Gillis, S., Hyam, E., Abrahamov, A., Elstein, D., and Zimran, A. (1999) Platelet function abnormalities in Gaucher disease patients. *Am J Hematol* 61, 103-106
71. Givol, N., Goldstein, G., Peleg, 0., Shenkman, B., Zimran, A., Elstein, D., and Kenet, G. (2012) Thrombocytopenia and bleeding in dental procedures of patients with Gaucher disease. *Haemophilia* 18, 117-121
72. Giona, F., Palumbo, G., Amendola, A., Santoro, C., and Mazzuconi, M. G. (2006) Platelet function and coagulation abnormalities in type 1 Gaucher disease patients: effects of enzyme replacement therapy (ERT). *J Thromb Haemost* 4, 1831-1833
73. Bratosin, D., Tissier, J. P., Lapillonne, H., Hermine, 0., de Villemeur, T. B., Cotoraci, C., Montreuil, J., and Mignot, C. (2011) A cytometric study of the red blood cells in Gaucher disease reveals their abnormal shape that may be involved in increased erythrophagocytosis. *Cytometry B Clin Cytom* 80, 28-37
74. Saroha, V., Gupta, P., Singh, M., and Singh, T. (2009) Pseudogaucher cells obscuring multiple myeloma: a case report. *Cases J* 2, 9147 Blair, H. C., Robinson, L. J., Iqbal, J., Sun, L., and Zaidi, M. (2010) Glucocerebrosidase gene-deficient mouse recapitulates Gaucher disease displaying cellular and molecular dysregulation beyond the macrophage. *Proc Natl Acad Sci USA* 107, 19473-19478
57. Yan, C., and Gao, H. (2012) New insights for C5a and C5a receptors in sepsis. *Front Immunol* 3, 368
58. Ricklin, D., Hajishengallis, G., Yang, K., and Lambris, J. D. (2010) Complement: a key system for immune surveillance and homeostasis. *Nat Immunol* 11, 785-797
59. Guo, R. F., and Ward, P. A. (2005) Role of C5a in inflammatory responses. *Annual review of immunology* 23, 821-852
60. Zhang, X., and Kohl, J. (2010) A complex role for complement in allergic asthma. *Evpert review of clinical immunology* 6, 269-277
61. Kohl, J., Baelder, R., Lewkowich, T. P., Pandey, M. K., Hawlisch, H., Wang, L., Best, J., Herman, N. S., Sproles, A. A., Zwirner, J., Whitsett, J. A., Gerard, C., Sfyroera, G., Lambris, J. D., and Wills-Karp, M. (2006) A regulatory role for the C5a anaphylatoxin in type 2 immunity in asthma. *J Clin Invest* 116, 783-796
62. Koyasu, S. (2003) The role of PI3K in immune cells. *Nature immunology* 4, 313-319
63. Davignon, I., Catalina, M. D., Smith, D., Montgomery, J., Swantek, J., Croy, J., Siegelman, M., and Wilkie, T. M. (2000) Normal hematopoiesis and inflammatory responses despite discrete signaling defects in Galpha15 knockout mice. *Molecular and cellular biology* 20, 797-804
64. Haas, P. J., and van Strijp, J. (2007) Anaphylatoxins: their role in bacterial infection and inflammation. *Immunol Res* 37, 161-175
65. van Lookeren Campagne, M., Wiesmann, C., and Brown, E. J. (2007) Macrophage complement receptors and pathogen clearance. *Cell Microbiol* 9, 2095-2102
66. Karsten, C. M., Pandey, M. K., Figge, J., Kilchenstein, R., Taylor, P. R., Rosas, M., McDonald, J. U., Orr, S. J., Berger, M., Petzold, D., Blanchard, V., Winkler, A., Hess, C., Reid, D. M., Majoul, I. V., Strait, R. T., Harris, N. L., Kohl, G., Wex, E., Ludwig, R., Zillikens, D., Nimmerjahn, F., Finkelman, F. D., Brown, G. D., Ehlers, M., and Kohl, J. (2012) Anti-inflammatory activity of IgG1 mediated by Fc galactosylation and association of FcgammaRIIB and dectin-1. *Nat Med* 18, 1401-1406
67. Boot, R. G., Verhoek, M., de Fost, M., Hollak, C. E., Maas, M., Bleijlevens, B., van Breemen, M. J., van Meurs, M., Boven, L. A., Laman, J. D., Moran, M. T., Cox, T. M., and Aerts, J. M. (2004) Marked elevation of the chemokine CCL18/PARC in Gaucher disease: a novel surrogate marker for assessing therapeutic intervention. *Blood* 103, 33-39
68. Atamas, S. P., Luzina, I. G., Choi, J., Tsymbalyuk, N., Carbonetti, N. H., Singh, L S., Trojanowska, M., Jimenez, S. A., and White, B. (2003) Pulmonary and activation-regulated chemokine stimulates collagen production in lung fibroblasts. *Am J Respir Cell Mol Biol* 29, 743-749
69. Karsten, C. M., Laumonnier, Y., Eurich, B., Ender, F., Broker, K., Roy, S., Czabanska, A., Vollbrandt, T., Figge, J., and Kohl, J. (2015) Monitoring and Cell-Specific Deletion of C5aR1 Using a Novel Floxed GFP-C5aR1 Reporter Knock-in Mouse. *JImmunol* 194, 1841-1855
70. Gillis, S., Hyam, E., Abrahamov, A., Elstein, D., and Zimran, A. (1999) Platelet function abnormalities in Gaucher disease patients. *Am J Hematol* 61, 103-106
71. Givol, N., Goldstein, G., Peleg, O., Shenkman, B., Zinran, A., Elstein, D., and Kenet, G. (2012) Thrombocytopenia and bleeding in dental procedures of patients with Gaucher disease. *Haemophilia* 18, 117-121
72. Giona, F., Palumbo, G., Amendola, A., Santoro, C., and Mazzuconi, M. G. (2006) Platelet function and coagulation abnormalities in type 1 Gaucher disease patients: effects of enzyme replacement therapy (ERT). *J Thromb Haemost* 4, 1831-1833
73. Bratosin, D., Tissier, J. P., Lapillonne, H., Hermine, O., de Villemeur, T. B., Cotoraci, C., Montreuil, J., and Mignot, C. (2011) A cytometric study of the red blood cells in Gaucher disease reveals their abnormal shape that may be involved in increased erythrophagocytosis. *Cytometry B Clin Cytom* 80, 28-37
74. Saroha, V., Gupta, P., Singh, M., and Singh, T. (2009) Pseudogaucher cells obscuring multiple myeloma: a case report. *Cases J* 2, 9147
75. Machaczka, M., Klimkowska, M., Regenthal, S., and Hagglund, H. (2011) Gaucher disease with foamy transformed macrophages and erythrophagocytic activity. *J Inherit Metab Dis* 34, 233-235
76. Gerard, C., and Gerard, N. P. (1994) C5A anaphylatoxin and its seven transmembrane-segment receptor. *Annu Rev Immunol* 12, 775-808
77. Goldstein, I., Hoffstein, S., Gallin, J., and Weissmann, G. (1973) Mechanisms of lysosomal enzyme release from human leukocytes: microtubule assembly and membrane fusion induced by a component of complement. *Proc Natl Acad Sci USA* 70, 2916-2920
78. Hara, T., Shimizu, K., Ogawa, F., Yanaba, K., Iwata, Y., Muroi, E., Takenaka, M., Komura, K., Hasegawa, M., Fujimoto, M., and Sato, S. (2010) Platelets control leukocyte recruitment in a murine model of cutaneous arthus reaction. *Am J Pathol* 176, 259-269
79. Daito, J., Harada, Y., Dai, P., Yamaoka, Y., Tamagawa-Mineoka, R., Katoh, N., and Takamatsu, T. (2014) Neutrophil Phagocytosis of Platelets in the Early Phase of 2,4,6-trinitro-1-chlorobenzene (TNCB)-induced Dermatitis in Mice. *Acta Histochem Cytochem* 47, 67-74
80. Shantsila, E., and Lip, G. Y. (2009) The role of monocytes in thrombotic disorders. Insights from tissue factor, monocyte-platelet aggregates and novel mechanisms. *Thromb Haemost* 102, 916-924
81. Alonzo, M. T., Lacuesta, T. L., Dimaano, E. M., Kurosu, T., Suarez, L. A., Mapua, C. A., Akeda, Y., Matias, R. R., Kuter, D. J., Nagata, S., Natividad, F. F., and Oishi, K. (2012) Platelet apoptosis and apoptotic platelet clearance by macrophages in secondary dengue virus infections. *J Infect Dis* 205, 1321-1329
82. Semple, J. W., Italiano, J. E., Jr., and Freedman, J. (2011) Platelets and the immune continuum. *Nat Rev Immunol* 11, 264-274
83. Weyrich, A. S., Elstad, M. R., McEver, R. P., McIntyre, T. M., Moore, K. L., Morrissey, J. H., Prescott, S. M., and Zimmerman, G. A. (1996) Activated platelets signal chemokine synthesis by human monocytes. *J Clin Invest* 97, 1525-1534
84. Basu, S., Kaufman, B., and Roseman, S. (1968) Enzymatic synthesis of ceramide-glucose and ceramidelactose by glycosyltransferases from embryonic chicken brain. *The Journal of biological chemistry* 243, 5802-5804
85. Vincent, M., Sayre, N. L., Graham, M. J., Crooke, R. M., Shealy, D. J., and Liscum, L. (2010) Evaluation of an anti-tumor necrosis factor therapeutic in a mouse model of Niemann-Pick C liver disease. *PLoS One* 5, e12941
86. Weber, C., and Noels, H. (2011) Atherosclerosis: current pathogenesis and therapeutic options. *Nat Med* 17, 1410-1422
87. Castaneda, J. A., Lim, M. J., Cooper, J. D., and Pearce, D. A. (2008) Immune system irregularities in lysosomal storage disorders. *Acta Neuropathol* 115, 159-174
88. Rimkunas, V. M., Graham, M. J., Crooke, R. M., and Liscum, L. (2009) TNF-{alpha} plays a role in hepatocyte apoptosis in Niemann-Pick type C liver disease. *J Lipid Res* 50, 327-333
89. Simonaro, C. M., Ge, Y., Eliyahu, E., He, X., Jepsen, K. J., and Schuchman, E. H. (2010) Involvement of the Toll-like receptor 4 pathway and use of TNF-alpha antagonists for treatment of the mucopolysaccharidoses. *Proc Natl Acad Sci USA* 107, 222-227
90. Nakashima, H., Ogawa, Y., Shono, S., Kinoshita, M., Nakashima, M., Sato, A., Ikarashi, M., and Seki, S. (2013) Activation of CD1 1b+ Kupffer cells/macrophages as a common cause for exacerbation of TNF/Fas-ligand-dependent hepatitis in hypercholesterolemic mice. *PLoS One* 8, e49339
91. De Francesco, P. N., Mucci, J. M., Ceci, R., Fossati, C. A., and Rozenfeld, P. A. (2013) Fabry disease peripheral blood immune cells release inflammatory cytokines: role of globotriaosylceramide. *Mol Genet Metab* 109, 93-99
92. Hayase, T., Shimizu, J., Goto, T., Nozaki, Y., Mori, M., Takahashi, N., Namba, E., Yamagata, T., and Momoi, M. Y. (2010) Unilaterally and rapidly progressing white matter lesion and elevated cytokines in a patient with Tay-Sachs disease. *Brain Dev* 32, 244-247
93. Kawashita, E., Tsuji, D., Toyoshima, M., Kanno, Y., Matsuno, H., and Itoh, K. (2011) Prostaglandin E2 reverses aberrant production of an inflammatory chemokine by microglia from Sandhoff disease model mice through the cAMP-PKA pathway. *PLoS One* 6, e16269
75. Machaczka, M., Klimkowska, M., Regenthal, S., and Hagglund, H. (2011) Gaucher disease with foamy transformed macrophages and erythrophagocytic activity. *J Inherit Metab Dis* 34, 233-235
76. Gerard, C., and Gerard, N. P. (1994) C5A anaphylatoxin and its seven transmembrane-segment receptor. *Annu Rev Immunol* 12, 775-808
77. Goldstein, I., Hoffstein, S., Gallin, J., and Weissmann, G. (1973) Mechanisms of lysosomal enzyme release from human leukocytes: microtubule assembly and membrane fusion induced by a component of complement. *Proc Natl Acad Sci USA* 70, 2916-2920
78. Hara, T., Shimizu, K., Ogawa, F., Yanaba, K., Iwata, Y., Muroi, E., Takenaka, M., Komura, K., Hasegawa, M., Fujimoto, M., and Sato, S. (2010) Platelets control leukocyte recruitment in a murine model of cutaneous arthus reaction. *Am J Pathol* 176, 259-269
79. Daito, J., Harada, Y., Dai, P., Yamaoka, Y., Tamagawa-Mineoka, R., Katoh, N., and Takamatsu, T. (2014) Neutrophil Phagocytosis of Platelets in the Early Phase of 2,4,6-trinitro-1-chlorobenzene (TNCB)-induced Dermatitis in Mice. *Acta Histochem Cytochem* 47, 67-74
80. Shantsila, E., and Lip, G. Y. (2009) The role of monocytes in thrombotic disorders. Insights from tissue factor, monocyte-platelet aggregates and novel mechanisms. *Thronb Haemost* 102, 916-924
81. Alonzo, M. T., Lacuesta, T. L., Dimaano, E. M., Kurosu, T., Suarez, L. A., Mapua, C. A., Akeda, Y., Matias, R. R., Kuter, D. J., Nagata, S., Natividad, F. F., and Oishi, K. (2012) Platelet apoptosis and apoptotic platelet clearance by macrophages in secondary dengue virus infections. *J Infect Dis* 205, 1321-1329
82. Semple, J. W., Italiano, J. E., Jr., and Freedman, J. (2011) Platelets and the immune continuum. *Nat Rev Immunol* 11, 264-274
83. Weyrich, A. S., Elstad, M. R., McEver, R. P., McIntyre, T. M., Moore, K. L., Morrissey, J. H., Prescott, S. M., and Zimmerman, G. A. (1996) Activated platelets signal chemokine synthesis by human monocytes. *J Clin Invest* 97, 1525-1534
84. Basu, S., Kaufman, B., and Roseman, S. (1968) Enzymatic synthesis of ceramide-glucose and ceramidelactose by glycosyltransferases from embryonic chicken brain. *The Journal of biological chemistry* 243, 5802-5804

85. Vincent, M., Sayre, N. L., Graham, M. J., Crooke, R. M., Shealy, D. J., and Liscum, L. (2010) Evaluation of an anti-tumor necrosis factor therapeutic in a mouse model of Niemann-Pick C liver disease. *PLoS One* 5, e12941
86. Weber, C., and Noels, H. (2011) Atherosclerosis: current pathogenesis and therapeutic options. *Nat Med* 17, 1410-1422
87. Castaneda, J. A., Lim, M. J., Cooper, J. D., and Pearce, D. A. (2008) Immune system irregularities in lysosomal storage disorders. *Acta Neuropathol* 115, 159-174
88. Rimkunas, V. M., Graham, M. J., Crooke, R. M., and Liscum, L. (2009) TNF-{alpha} plays a role in hepatocyte apoptosis in Niemann-Pick type C liver disease. *J Lipid Res* 50, 327-333
89. Simonaro, C. M., Ge, Y., Eliyahu, E., He, X., Jepsen, K. J., and Schuchman, E. H. (2010) Involvement of the Toll-like receptor 4 pathway and use of TNF-alpha antagonists for treatment of the mucopolysaccharidoses. *Proc Nat Acad Sci USA* 107, 222-227
90. Nakashima, H., Ogawa, Y., Shono, S., Kinoshita, M., Nakashima, M., Sato, A., Ikarashi, M., and Seki, S. (2013) Activation of CD11b+ Kupffer cells/macrophages as a common cause for exacerbation of TNF/Fas-ligand-dependent hepatitis in hypercholesterolemic mice. *PLoS One* 8, e49339
91. De Francesco, P. N., Mucci, J. M., Ceci, R., Fossati, C. A., and Rozenfeld, P. A. (2013) Fabry disease peripheral blood immune cells release inflammatory cytokines: role of globotriaosylceramide. *Mol Genet Metab* 109, 93-99
92. Hayase, T., Shimizu, J., Goto, T., Nozaki, Y., Mori, M., Takahashi, N., Namba, E., Yamagata, T., and Momoi, M. Y. (2010) Unilaterally and rapidly progressing white matter lesion and elevated cytokines in a patient with Tay-Sachs disease. *Brain Dev* 32, 244-247
93. Kawashita, E., Tsuji, D., Toyoshima, M., Kanno, Y., Matsuno, H., and Itoh, K. (2011) Prostaglandin E2 reverses aberrant production of an inflammatory chemokine by microglia from Sandhoff disease model mice through the cAMP-PKA pathway. *PLoS One* 6, e16269
94. Snook, E. R., Fisher-Perkins, J. M., Sansing, H. A., Lee, K. M., Alvarez, X., Maclean, A. G., Peterson, K. E., Lackner, A. A., and Bunnell, B. A. (2013) Innate Immune Activation in the Pathogenesis of a Murine Model of Globoid Cell Leukodystrophy. *Am J Pathol*
95. Rosenbloom, B. E., and Weinreb, N. J. (2013) Gaucher disease: a comprehensive review. Critical reviews in oncogenesis 18, 163-175
96. Connock, M., Burls, A., Frew, E., Fry-Smith, A., Juarez-Garcia, A., McCabe, C., Wailoo, A., Abrams, K., Cooper, N., Sutton, A., O'Hagan, A., and Moore, D. (2006) The clinical effectiveness and costeffectiveness of enzyme replacement therapy for Gaucher's disease: a systematic review. Health Technol Assess 10, iii-iv, ix-136
97. Heller, T., Hennecke, M., Baumann, U., Gessner, J. E., zu Vilsendorf, A. M., Baensch, M., Boulay, F., Kola, A., Klos, A., Bautsch, W., and Kohl, J. (1999) Selection of a C5a receptor antagonist from phage libraries attenuating the inflammatory response in immune complex disease and ischemia/reperfusion injury. J Immunol 163, 985-994
98. Baumann, U., Kohl, J., Tschernig, T., Schwerter-Strumpf, K., Verbeek, J. S., Schmidt, R. E., and Gessner, J. E. (2000) A codominant role of Fc gamma RI/III and C5aR in the reverse Arthus reaction. J Immunol 164, 1065-1070
99. Godau, J., Heller, T., Hawlisch, H., Trappe, M., Howells, E., Best, J., Zwirner, J., Verbeek, J. S., Hogarth, P. M., Gerard, C., Van Rooijen, N., Klos, A., Gessner, J. E., and Kohl, J. (2004) C5a initiates the inflammatory cascade in immune complex peritonitis. J Immunol 173, 3437-3445
100. Kohl, J., Baelder, R., Lewkowich, I. P., Pandey, M. K., Hawlisch, H., Wang, L. H., Best, J., Herman, N. S., Sproles, A. A., Zwirner, J., Whitsett, J. A., Gerard, C., Sfyroera, G., Lambris, J. D., and Wills-Karp, M. (2006) A regulatory role for the C5a anaphylatoxin in, type 2 immunity in asthma. J Clin Invest 116, 783-796
101. Xu, Y. H., Sun, Y., Barnes, S., and Grabowski, G. A. (2010) Comparative Therapeutic Effects of Velaglucerase Alfa and Imiglucerase in a Gaucher Disease Mouse Model. PloS one 5
102. (14 in updated manuscript) Weaver, D. J., Jr., Reis, E. S., Pandey, M. K., Kohl, G., Harris, N., Gerard, C., and Kohl, J. (2010) C5a receptor-deficient dendritic cells promote induction of Treg and Th17 cells. Eur J Immunol 40, 710-721
103. Jongerius, I., Kohl, J., Pandey, M. K., Ruyken, M., van Kessel, K. P., van Strijp, J. A., and Rooijakkers, S. H. (2007) Staphylococcal complement evasion by various convertase-blocking molecules. J Exp Med 204, 2461-2471
104. Stemerding, A. M., Kohl, J., Pandey, M. K., Kuipers, A., Leusen, J. H., Boross, P., Nederend, M., Vidarsson, G., Weersink, A. Y., van de Winkel, J. G., van Kessel, K. P., and van Strijp, J. A. (2013) *Staphylococcus aureus* formyl peptide receptor-like 1 inhibitor (FLIPr) and its homologue FLIPr-like are potent FcgammaR antagonists that inhibit IgG-mediated effector functions. J Immunol 191, 353-362.
105. Biburger, M. et al. Monocyte subsets responsible for immunoglobulin G-dependent effector functions in vivo. Immunity 35, 932-944 (2011).
106. (3 in updated manuscript) van Dussen, L., Biegstraaten, M., Hollak, C. E. & Dijkgraaf, M. G. Cost-effectiveness of enzyme replacement therapy for type 1 Gaucher disease. *Orphanet J Rare Dis* 9, 51, doi:10.1186/1750-1172-9-51 (2014).
107. (4 in updated manuscript) Wyatt, K. et al. The effectiveness and cost-effectiveness of enzyme and substrate replacement therapies: a longitudinal cohort study of people with lysosomal storage disorders. *Health Technol Assess* 16, 1-543, doi:10.3310/hta16390 (2012).
108. (5 in updated manuscript) Aflaki, E. et al. Lysosomal storage and impaired autophagy lead to inflammasome activation in Gaucher macrophages. *Aging Cell* 15, 77-88, doi:10.1111/acel.12409 (2016).
109. (6 in updated manuscript) Gervas-Arruga, J. et al. The Influence of Genetic Variability and Proinflammatory Status on the Development of Bone Disease in Patients with Gaucher Disease. *PLoS ONE* 10, e0126153, doi:10.1371/journal.pone.0126153 (2015).
110. (7 in updated manuscript) Mistry, P. K., Taddei, T., vom Dahl, S. & Rosenbloom, B. E. Gaucher disease and malignancy: a model for cancer pathogenesis in an inborn error of metabolism. *Crit Rev Oncog* 18, 235-246 (2013).
111. (8 in updated manuscript) Bultron, G. et al. The risk of Parkinson's disease in type 1 Gaucher disease. *J Inherit Metab Dis* 33, 167-173, doi:10.1007/s10545-010-9055-0 (2010).
10 Kolev, M., Friec, G. L. & Kemper, C. Complement [mdash] tapping into new sites and effector systems. Nat Rev Immunol 14, 811-820, doi:10.1038/nri3761 (2014).
11 Klos, A., Wende, E., Wareham, K. J. & Monk, P. N. International Union of Basic and Clinical Pharmacology. [corrected]. LXXXVII. Complement peptide C5a, C4a, and C3a receptors. Pharmacol Rev 65, 500-543 (2013).

13. Strainic, M. G. et al. Locally produced complement fragments C5a and C3a provide both costimulatory and survival signals to naive CD4+ T cells. Immunity 28, 425-435, doi:10.1016/j.immuni.2008.02.001 (2008).
15 Lajoie, S. et al. Complement-mediated regulation of the IL-17A axis is a central genetic determinant of the severity of experimental allergic asthma. Nat Immunol 11, 928-935, doi:10.1038/ni.1926 (2010).
16 Merad, M., Sathe, P., Helft, J., Miller, J. & Mortha, A. The dendritic cell lineage: ontogeny and function of dendritic cells and their subsets in the steady state and the inflamed setting. Annu Rev Immunol 31, 563-604, doi:10.1146/annurev-immunol-020711-074950 (2013).
17 Otto, M. et al. C5a mutants are potent antagonists of the C5a receptor (CD88) and of C5L2: position 69 is the locus that detennines agonism or antagonism. J Biol Chem 279, 142-151, doi:10.1074/jbc.M310078200 (2004).
24 Kanfer, J. N., Legler, G., Sullivan, J., Raghavan, S. S. & Mumford, R. A. The Gaucher mouse. Biochem Biophys Res Commun 67, 85-90 (1975).
26 Sun, Y., Quinn, B., Witte, D. P. & Grabowski, G. A. Gaucher disease mouse models: point mutations at the acid beta-glucosidase locus combined with low-level prosaposin expression lead to disease variants. J Lipid Res 46, 2102-2113, doi:10.1194/jlr.M500202-JLR200 (2005).
27 Xu, Y. H. et al. Dependence of reversibility and progression of mouse neuronopathic Gaucher disease on acid beta-glucosidase residual activity levels. Mol Genet Metab 94, 190-203, doi:S1096-7192(08)00016-4 [pii] 10.1016/j.ymgme. 2008.01.013 (2008).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited, for all purposes. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a lysosomal storage disease in an individual in need thereof, comprising administering a C5aR antagonist to said individual, said individual having one or more clinical signs selected from hepatosplenomegaly, anemia, thrombocytopenia, bone defects, or a combination thereof.

2. The method of claim 1, said lysosomal storage disease being selected from globoid cell leukodystrophy, GM2 gangliosidosis, Niemann-Pick C, mucopolysaccharidoses, Fabry, Tay-Sachs, Sandhoff, Hypercholesterolemia, Gaucher's Disease, and combinations thereof.

3. The method according to claim 1, said C5aR antagonist being administered in an amount sufficient to reduce inflammation in one or both of brain and lung tissue.

4. The method according to claim 1, said C5aR antagonist being administered in an amount sufficient to reduce complement activation.

5. The method according to claim 1, said C5aR antagonist being administered in an amount sufficient to reduce circulating levels of inflammatory cytokines and chemokines.

6. The method according, to claim 1, said administering being carried out before, after, or during a second treatment, said second treatment being selected from gene therapy, substrate reduction therapy, enzyme replacement products, or a combination thereof.

7. The method of claim 1, said lysosomal storage disease being Gaucher's disease.

8. The method of claim 6, said second treatment being substrate reduction therapy comprising administration of one or more of eligustat and miglustat.

9. The method of claim 1, said C5aR antagonist being an $A8^{\Delta 71-73}$ peptide.

10. The method of claim 9, said lysosomal storage disease being selected from globoid cell leukodystrophy, GM2 gangliosidosis, Niemann-Pick C, mucopolysaccharidoses, Fabry, Tay-Sachs, Sandhoff, Hypercholesterolemia, Gaucher's Disease, and combinations thereof.

11. The method according to claim 9, said $A8^{\Delta 71-73}$ peptide being administered in an amount sufficient to reduce complement activation.

12. The method according to claim 9, said $A8^{\Delta 71-73}$ peptide being administered in an amount sufficient to reduce circulating levels of inflammatory cytokines and chemokines.

13. The method according to claim 9, said $A8^{\Delta 71-73}$ peptide being administered in an amount sufficient to reduce inflammation in one or both of brain and lung tissue.

14. The method according to claim 9, said administering being carried out before, after, or during a second treatment, said second treatment being selected from gene therapy, substrate reduction therapy, enzyme replacement products, or a combination thereof.

15. A method of treating Gaucher's disease in an individual in need. thereof, comprising administering an $A8^{\Delta 71-73}$ peptide to said individual, said individual having one or more clinical signs selected from hepatosplenomegaly anemia, thrombocytopenia, bone defects, or a combination thereof.

16. The method according to claim 15, said $A8^{\Delta 71-73}$ peptide being administered in an amount sufficient to reduce complement activation.

17. The method according to claim 15, said $A8^{\Delta 71-73}$ peptide being administered in an amount sufficient to reduce circulating levels of inflammatory cytokines and chemokines.

18. The method of claim 15, said administering being carried out before, after, or during a second treatment, said second treatment being selected from gene therapy, substrate reduction therapy, enzyme replacement products, or a combination thereof.

19. The method according to claim 15, said $A8^{\Delta 71-73}$ peptide being administered in an amount sufficient to reduce inflammation in one or both of brain and lung tissue.

* * * * *